US007011682B2

(12) United States Patent
Lashinski et al.

(10) Patent No.: US 7,011,682 B2
(45) Date of Patent: Mar. 14, 2006

(54) METHODS AND APPARATUS FOR REMODELING AN EXTRAVASCULAR TISSUE STRUCTURE

(75) Inventors: Randall Lashinski, Santa Rosa, CA (US); David Taylor, Lake Forest, CA (US); Matthew Birdsall, Santa Rosa, CA (US); Jan Lau, Windsor, CA (US)

(73) Assignee: Edwards Lifesciences AG, Saint Prex (CH)

( * ) Notice: Subject to any disclaimer, the term of this patent is extended or adjusted under 35 U.S.C. 154(b) by 0 days.

(21) Appl. No.: 10/634,655

(22) Filed: Aug. 5, 2003

(65) Prior Publication Data

US 2004/0153146 A1    Aug. 5, 2004

Related U.S. Application Data

(63) Continuation-in-part of application No. 10/066,302, filed on Jan. 30, 2002, which is a continuation-in-part of application No. 09/774,869, filed on Jan. 30, 2001, now Pat. No. 6,537,314, which is a continuation-in-part of application No. 09/968,272, filed on Oct. 1, 2001, now Pat. No. 6,709,456, which is a continuation of application No. 09/494,233, filed on Jan. 31, 2000, now Pat. No. 6,402,781.

(60) Provisional application No. 60/265,995, filed on Feb. 1, 2001, provisional application No. 60/429,281, filed on Nov. 25, 2002, provisional application No. 60/488,334, filed on Jul. 18, 2003.

(51) Int. Cl.
A61F 2/06    (2006.01)

(52) U.S. Cl. .................... 623/2.37; 623/1.1; 623/1.11; 600/37

(58) Field of Classification Search ............... 623/2.36, 623/2.37, 1.1, 2.1, 11.11, 1.11, 12, 902, 66.1; 600/37; 128/898; 606/108, 191, 194; 604/528
See application file for complete search history.

(56) References Cited

U.S. PATENT DOCUMENTS

| 4,128,100 A | 12/1978 | Wendorff |
| 4,164,046 A | 8/1979 | Cooley |
| 4,655,771 A | 4/1987 | Wallsten |
| 4,917,698 A | 4/1990 | Carpentier et al. |
| 4,954,126 A | 9/1990 | Wallsten |
| 5,006,106 A | 4/1991 | Angelchik |
| 5,041,130 A | 8/1991 | Cosgrove et al. |

(Continued)

FOREIGN PATENT DOCUMENTS

DE     196 05 042 A1    1/1998

(Continued)

OTHER PUBLICATIONS

U.S. Appl. No. 60/213,782, Cohn et al., filed Jun. 2000.

(Continued)

*Primary Examiner*—David J. Isabella
*Assistant Examiner*—Urmi Chattopadhyay
(74) *Attorney, Agent, or Firm*—David L. Hauser

(57) ABSTRACT

A medical apparatus and method for remodeling a mitral valve annulus adjacent to the coronary sinus includes an elongate body having a proximal end and a distal end. The elongate body is movable from a first, flexible configuration for transluminal delivery to at least a portion of the coronary sinus to a second configuration for remodeling the mitral valve annulus.

23 Claims, 33 Drawing Sheets

U.S. PATENT DOCUMENTS

| | | | |
|---|---|---|---|
| 5,061,275 A | 10/1991 | Wallsten et al. |
| 5,061,277 A | 10/1991 | Carpentier et al. |
| 5,064,431 A | 11/1991 | Gilbertson et al. |
| 5,064,435 A | 11/1991 | Porter |
| 5,099,838 A | 3/1992 | Bardy |
| 5,104,404 A | 4/1992 | Wolff |
| 5,104,407 A | 4/1992 | Lam et al. |
| 5,163,955 A | 11/1992 | Love et al. |
| 5,165,403 A | 11/1992 | Mehra |
| 5,170,802 A | 12/1992 | Mehra |
| 5,201,880 A | 4/1993 | Wright et al. |
| 5,290,300 A | 3/1994 | Cosgrove et al. |
| 5,304,131 A | 4/1994 | Paskar |
| 5,350,420 A | 9/1994 | Cosgrove et al. |
| 5,383,892 A | 1/1995 | Cardon et al. |
| 5,390,661 A | 2/1995 | Griffith et al. |
| 5,450,860 A | 9/1995 | O'Connor |
| 5,476,471 A | 12/1995 | Shifrin et al. |
| 5,534,007 A | 7/1996 | St. Germain et al. |
| 5,545,209 A | 8/1996 | Roberts et al. |
| 5,562,619 A | 10/1996 | Mirarchi et al. |
| 5,571,135 A | 11/1996 | Fraser et al. |
| 5,584,879 A | 12/1996 | Reimold et al. |
| 5,593,424 A | 1/1997 | Northrup, III |
| 5,593,442 A | 1/1997 | Klein |
| 5,607,444 A | 3/1997 | Lam |
| 5,674,280 A | 10/1997 | Davidson et al. |
| 5,702,343 A | 12/1997 | Alferness |
| 5,713,949 A | 2/1998 | Jayaraman |
| 5,716,397 A | 2/1998 | Myers |
| 5,741,274 A | 4/1998 | Lenker et al. |
| 5,817,126 A | 10/1998 | Imran |
| 5,824,066 A | 10/1998 | Gross |
| 5,824,071 A | 10/1998 | Nelson et al. |
| 5,876,419 A | 3/1999 | Carpenter et al. |
| 5,891,108 A | 4/1999 | Leone et al. |
| 5,911,732 A | 6/1999 | Hojeibane |
| 5,919,233 A | 7/1999 | Knopf et al. |
| 5,935,081 A | 8/1999 | Kadhiresan |
| 5,961,440 A | 10/1999 | Schweich, Jr. et al. |
| 5,961,545 A | 10/1999 | Lentz et al. |
| 5,961,565 A | 10/1999 | Kawabe et al. |
| 5,980,552 A | 11/1999 | Pinchasik et al. |
| 6,001,127 A | 12/1999 | Schoon et al. |
| 6,019,739 A | 2/2000 | Rhee et al. |
| 6,027,525 A | 2/2000 | Suh et al. |
| 6,045,497 A | 4/2000 | Schweich, Jr. et al. |
| 6,050,936 A | 4/2000 | Schweich, Jr. et al. |
| 6,051,020 A | 4/2000 | Goicoechea et al. |
| 6,059,715 A | 5/2000 | Schweich, Jr. et al. |
| 6,071,292 A | 6/2000 | Makower et al. |
| 6,077,214 A | 6/2000 | Mortier et al. |
| 6,077,296 A | 6/2000 | Shokoohi et al. |
| 6,095,968 A | 6/2000 | Snyders |
| 6,093,203 A | 7/2000 | Uflacker |
| 6,110,100 A | 8/2000 | Talpade |
| 6,123,662 A | 9/2000 | Alferness et al. |
| 6,123,699 A * | 9/2000 | Webster, Jr. ................ 604/528 |
| 6,143,024 A | 11/2000 | Campbell et al. |
| 6,146,325 A | 11/2000 | Lewis et al. |
| 6,155,968 A | 12/2000 | Wilk |
| 6,155,972 A | 12/2000 | Nauertz et al. |
| 6,161,543 A | 12/2000 | Cox et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,122 A | 12/2000 | Alferness |
| 6,171,329 B1 | 1/2001 | Shaw et al. |
| 6,174,279 B1 | 1/2001 | Girard |
| 6,183,411 B1 | 2/2001 | Mortier et al. |
| 6,183,512 B1 | 2/2001 | Howanec, Jr. et al. |
| 6,193,648 B1 | 2/2001 | Krueger |
| 6,203,556 B1 | 3/2001 | Evans et al. |
| 6,210,432 B1 | 4/2001 | Solem et al. |
| 6,217,610 B1 | 4/2001 | Carpentier et al. |
| 6,221,103 B1 | 4/2001 | Melvin |
| 6,230,714 B1 | 5/2001 | Alferness et al. |
| 6,241,654 B1 | 6/2001 | Alferness |
| 6,248,119 B1 | 6/2001 | Solem |
| 6,250,308 B1 | 6/2001 | Cox |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,264,691 B1 | 7/2001 | Gabbay |
| 6,325,826 B1 | 12/2001 | Vardi et al. |
| 6,343,605 B1 | 2/2002 | Lafontaine |
| 6,350,277 B1 | 2/2002 | Kocur |
| 6,368,343 B1 | 4/2002 | Bonutti et al. |
| 6,402,679 B1 | 6/2002 | Mortier et al. |
| 6,402,680 B1 | 6/2002 | Mortier et al. |
| 6,402,781 B1 | 6/2002 | Langberg et al. |
| 6,409,760 B1 | 6/2002 | Melvin |
| 6,537,314 B1 | 3/2003 | Langberg et al. |
| 6,569,198 B1 | 5/2003 | Wilson et al. |
| 6,602,288 B1 | 8/2003 | Cosgrove et al. |
| 6,626,899 B1 | 9/2003 | Houser et al. |
| 6,656,221 B1 | 12/2003 | Taylor et al. |
| 6,669,687 B1 | 12/2003 | Saadat |
| 6,676,702 B1 | 1/2004 | Mathis |
| 6,706,065 B1 | 3/2004 | Langberg et al. |
| 6,709,456 B1 | 3/2004 | Langberg et al. |
| 6,764,510 B1 | 7/2004 | Vidlund et al. |
| 6,790,231 B1 | 9/2004 | Liddicoat et al. |
| 6,793,673 B1 | 9/2004 | Kowalsky et al. |
| 6,797,001 B1 | 9/2004 | Mathis et al. |
| 6,800,090 B1 | 10/2004 | Alferness et al. |
| 6,810,882 B1 | 11/2004 | Langberg et al. |
| 6,824,562 B1 | 11/2004 | Mathis et al. |
| 2001/0018611 A1 | 8/2001 | Solem et al. |
| 2001/0044568 A1 | 11/2001 | Langberg et al. |
| 2002/0016628 A1 | 2/2002 | Langberg et al. |
| 2002/0019660 A1 | 2/2002 | Gianotti et al. |
| 2002/0022880 A1 | 2/2002 | Melvin |
| 2002/0087173 A1 * | 7/2002 | Alferness et al. ............ 606/151 |
| 2002/0103533 A1 | 8/2002 | Langberg et al. |
| 2002/0111533 A1 | 8/2002 | Melvin |
| 2002/0124857 A1 | 9/2002 | Schroeppel |
| 2002/0151961 A1 | 10/2002 | Lashinski et al. |
| 2002/0169504 A1 * | 11/2002 | Alferness et al. ........... 623/2.36 |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2003/0078465 A1 | 4/2003 | Pai et al. |
| 2003/0078654 A1 | 4/2003 | Taylor et al. |
| 2003/0083538 A1 * | 5/2003 | Adams et al. ................ 600/16 |
| 2003/0088305 A1 | 5/2003 | Van Schie et al. |
| 2003/0105520 A1 * | 6/2003 | Alferness et al. ........... 623/2.36 |
| 2003/0130730 A1 | 7/2003 | Cohn et al. |
| 2003/0130731 A1 * | 7/2003 | Vidlund et al. ............. 623/2.37 |
| 2003/0135267 A1 | 7/2003 | Solem et al. |
| 2003/0144697 A1 | 7/2003 | Mathis et al. |
| 2003/0225454 A1 | 12/2003 | Mathis et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |

| | | | |
|---|---|---|---|
| 2004/0133273 | A1 | 7/2004 | Cox |
| 2004/0138744 | A1 | 7/2004 | Lashinski et al. |
| 2004/0153146 | A1 | 8/2004 | Lashinski et al. |
| 2004/0153147 | A1 | 8/2004 | Mathis |
| 2004/0158321 | A1 | 8/2004 | Reuter et al. |
| 2004/0186566 | A1 | 9/2004 | Hindrichs et al. |
| 2004/0210240 | A1 | 10/2004 | Saint |
| 2004/0220654 | A1 | 11/2004 | Mathis et al. |
| 2004/0220657 | A1 | 11/2004 | Nieminen et al. |
| 2004/0267358 | A1 | 12/2004 | Reitan |
| 2005/0004667 | A1 | 1/2005 | Swinford et al. |
| 2005/0010240 | A1 | 1/2005 | Mathis et al. |
| 2005/0021121 | A1 | 1/2005 | Reuter et al. |
| 2005/0027351 | A1 | 2/2005 | Reuter et al. |

FOREIGN PATENT DOCUMENTS

| | | |
|---|---|---|
| DE | 196 11 755 A1 | 2/1998 |
| EP | 0 727 239 A2 | 8/1996 |
| EP | 0 727 239 A3 | 4/1997 |
| WO | WO 91/19465 | 12/1991 |
| WO | WO 95/16407 | 6/1995 |
| WO | WO 96/34211 | 10/1996 |
| WO | WO 96/40356 | 12/1996 |
| WO | WO 98/18411 | 5/1998 |
| WO | WO 98/29041 | 7/1998 |
| WO | WO 99/30647 | 6/1999 |
| WO | WO 99/44534 | 9/1999 |
| WO | WO 99/53977 | 10/1999 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 00/18320 | 4/2000 |
| WO | WO 00/41649 | 7/2000 |
| WO | WO 00/44313 A1 | 8/2000 |
| WO | WO 01/00111 A1 | 1/2001 |
| WO | WO 01/00114 A1 | 1/2001 |
| WO | WO 01/28455 A1 | 4/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 2004/084746 A2 | 10/2004 |

OTHER PUBLICATIONS

U.S. Appl. No. 60/242,466, Streeter, filed Oct. 2000.
U.S. Appl. No. 60/266,766, Cohn et al., filed Feb. 2001.
U.S. Appl. No. 60/273,893, Cohn et al., filed Mar. 2001.
U.S. Appl. No. 60/278,153, Cohn et al., filed Mar. 2001.
U.S. Appl. No. 60/279,973, Taylor et al., filed Mar. 2001.
U.S. Appl. No. 60/279,974, Taylor et al., filed Mar. 2001.
U.S. Appl. No. 60/280,038, Cohn et al., filed Mar. 2001.
U.S. Appl. No. 60/283,820, Cohn et al., filed Apr. 2001.
U.S. Appl. No. 60/312,217, Taylor et al., filed Aug. 2001.
U.S. Appl. No. 60/348,424, Taylor et al., filed Jan. 2002.
U.S. Appl. No. 60/339,481, Cohn et al., filed Oct. 2001.
Boyd et al., *Tricuspid annuloplasty*, Sep. 1974, The Journal of Thoracic and Cardiovascular Surgery, p. 344, 351.
Kurlansky et al., *Adjustable Annuloplasty for Tricuspid Insufficiency*, Oct. 1987, The Annals of Thoracic Surgery, p. 404-406.
Alonso-Lej, *Adjustable Annuloplasty for Tricuspid Insufficiency*, Sep. 1988, The Annals of Thoracic Surgery, Letter to the Editor, p. 368-369.
Chachques et al., *Latissimus Dorsi Dynamic Cardiomyoplasty*, 1989, The Society of Thoracic Surgeions, p. 600-604.
McCarthy et al., *Clinical experience with the Novacor ventricular assist system*, May 1990, J Thorac Cardiovasc Surg, p. 578-587.
Farrar et al., *A New Skeletal Muscle Linear-pull Energy Convertor as a Power Source for Prosthetic Circularoty Support Devices*, Sep. 1992, The Journal of Heart and Lung Transplantation, p. S341-S349.
Bolling et al., *Early outcome of mitral valve reconstruction in patients with end-stage cardiomyophathy*, Apr. 1995, The Journal of Thoracic and Cardiovascular Surgery, p. 676-683.
Bach et al., *Early improvement in congestive heart failure after correction of secondary mitral regurgitation in end-stage cardiomyopathy*, Jun. 1995, American Heart Journal, p. 1165-1170.
Beamson et al., *Development of a Protottype Magneticallly Suspended Rotar Ventricular Assist Device*, ASAIO Journal 1996, p. 275-280.
*Thoratec Ventricular Assist Device System*, 1996 Brochure.
McCarthy et al., *Early Results with Partial Left VEntriculectomy*, May 1997, Presented at the 77th Annual Meeting of the American Association of thoracic Surgeons.
Buchanan et al., *Circumferential Suture of the Mitral Annulus for Correction of Mitral Regurgitation in Dogs*, 1998, Veterinary Surgery vol. 27, p. 182-193.
Yamani et al., *Surgical Treatment of Chronic Heart Failure*, 2000, Congestive Heart Failure Second Edition, p. 767-784.
Bristow et al., *Heart Failure Management Using Implantable Devices for Ventricular Resynchronization: Comparison of Medical Therapy, Pacing, and Defibrillation in Chronic Heart Faillure (COMPANION) Trial*, Sep. 2000, Journal of Cardiac Failure, vol. 6, No. 3, p. 276-285.
Smolens et al., *Mitral Valve Repair in Heart Failure*, 2000, European Journal of Heart Faillure 2, p. 365-371.
Copy of International Search Report from PCT/US03/37727, filed Nov. 24, 2003.
Laaksovirta et al., *Expansion and bioabsorption of the self-reinforced lactic and glycolic acid copolymer prostatic spiral stent*, PubMed, Excerpt from J Urol Sep 2001; 166 (3):919-22, one sheet.
Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.
Yoneyama et al., *Super-elastic property of Ti—Ni alloy for use in dentistry*, PubMed, Excerpt from Front Med Biol Eng 2000; 10(2):97-103, one sheet.
Kotian, *Shape memory effect and super elasticity it's dental applications*, PubMed, Excerpt from Indian J Dent Res Apr-Jun 2001; 12(2):101-4, one sheet.
Kuo et al., *The use of nickel-titanium alloy in orthopedic surgery in China*, PubMed, Excerpt from Orthopedics Jan 1989; 12(1):111-6, one sheet.
Civjan et al., *Potential applications of certain nickel-titanium (nitinol) alloys*, PubMed, Excerpt from J Dent Res Jan-Feb 1975;54(1):89-96, one sheet.

Brennan, *Suite of Shape-Memory Polymers,* http:///pubs.acs.org/cen/topstory/7906notw1.html, News of the Week Materials, Feb. 5, 2001, vol. 79, No. 6, Cenear 79 6 pp. 5, ISSN 0009-2347, three sheets.

Stikeman, *Total Recall,* An MIT Enterprise Technology Review—Innovation, Jun. 2001, two sheets.

European Patent Office Office action dated Dec. 22, 2003 for Application No. 00 946 661.6-2310, 4 sheets.

Written Opinion dated Nov. 8, 2002 for International application No. PCT/EP01/10371, 14 sheets.

International Search Report dated Apr. 23, 2002 for International application No. PCT/EP 01/10371, 4 sheets.

International Search Report dated Mar. 15, 2000 for National application No. SE 9902455-6, 3 sheets.

International Search Report dated Oct. 9, 2002 for National application No. SE 0200073-5, 5 sheets.

International Search Report dated Jun. 5, 2003 for International application No. PCT/EP 02/14655, 7 sheets.

Buchanan JW, Sammarco CD, Circumferential Suture of the Mitral Annulus for Correction of Mitral Regurgitation in Dogs, PubMed, Excerpt from Vet Surg May-Jun. 1998; 27(3): 183-93, abstract, one sheet.

* cited by examiner

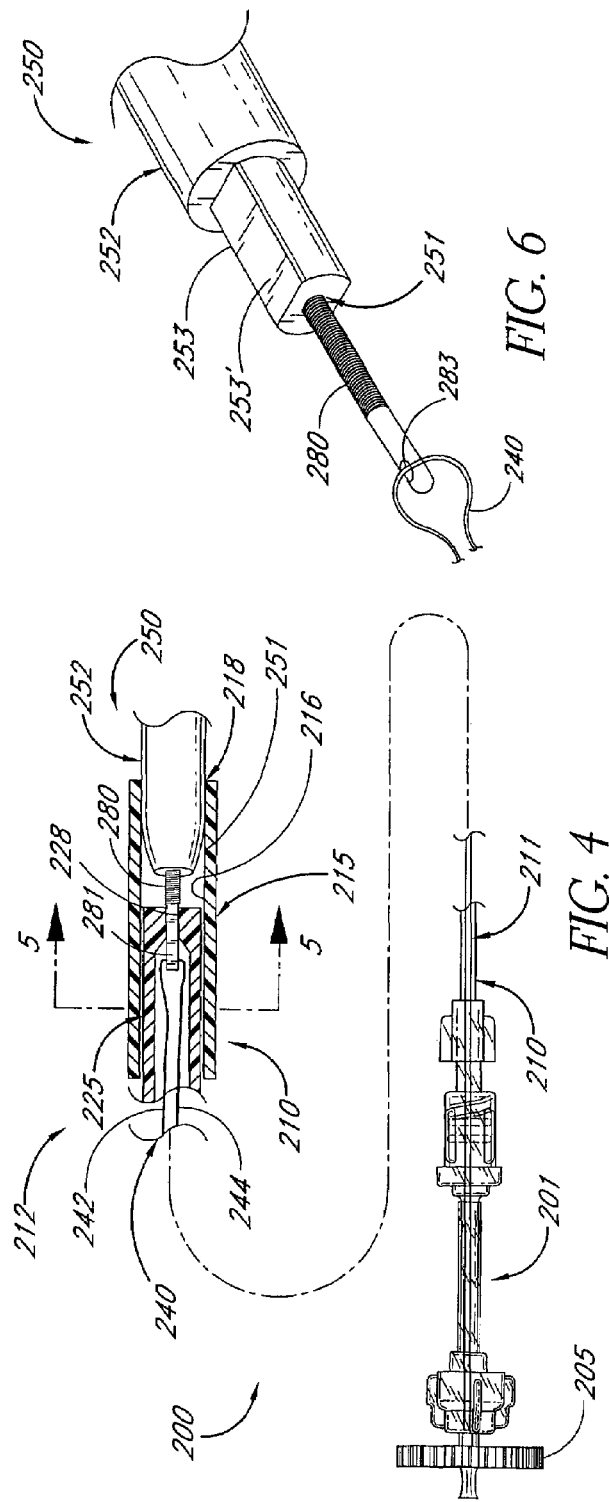
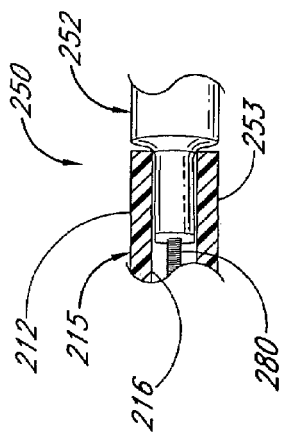
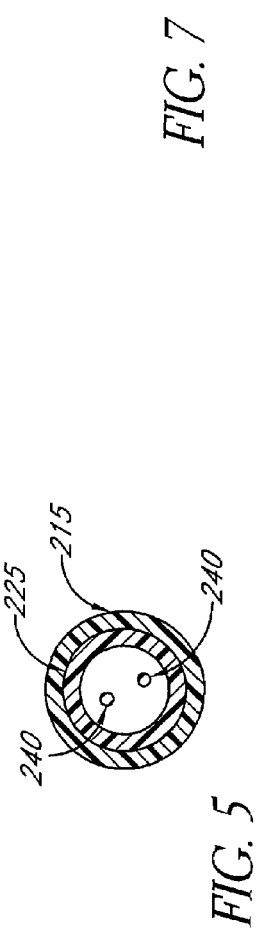

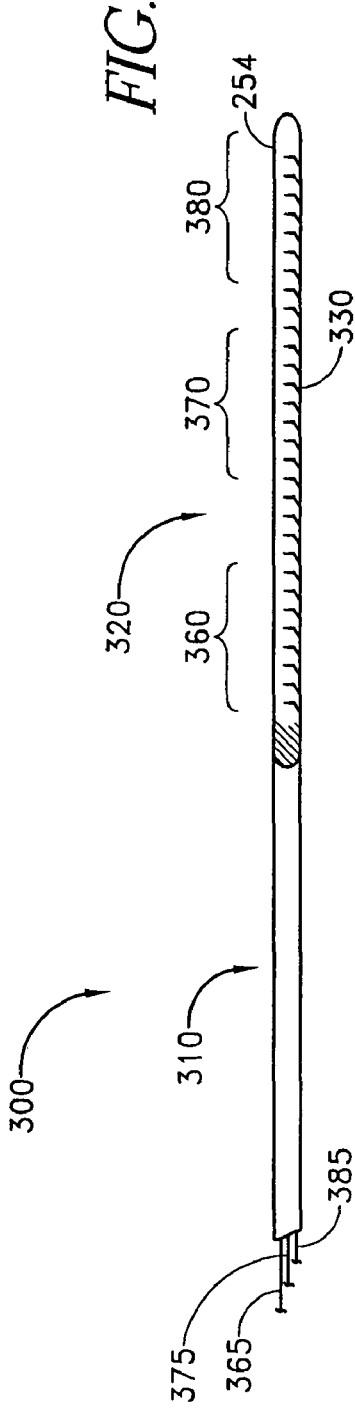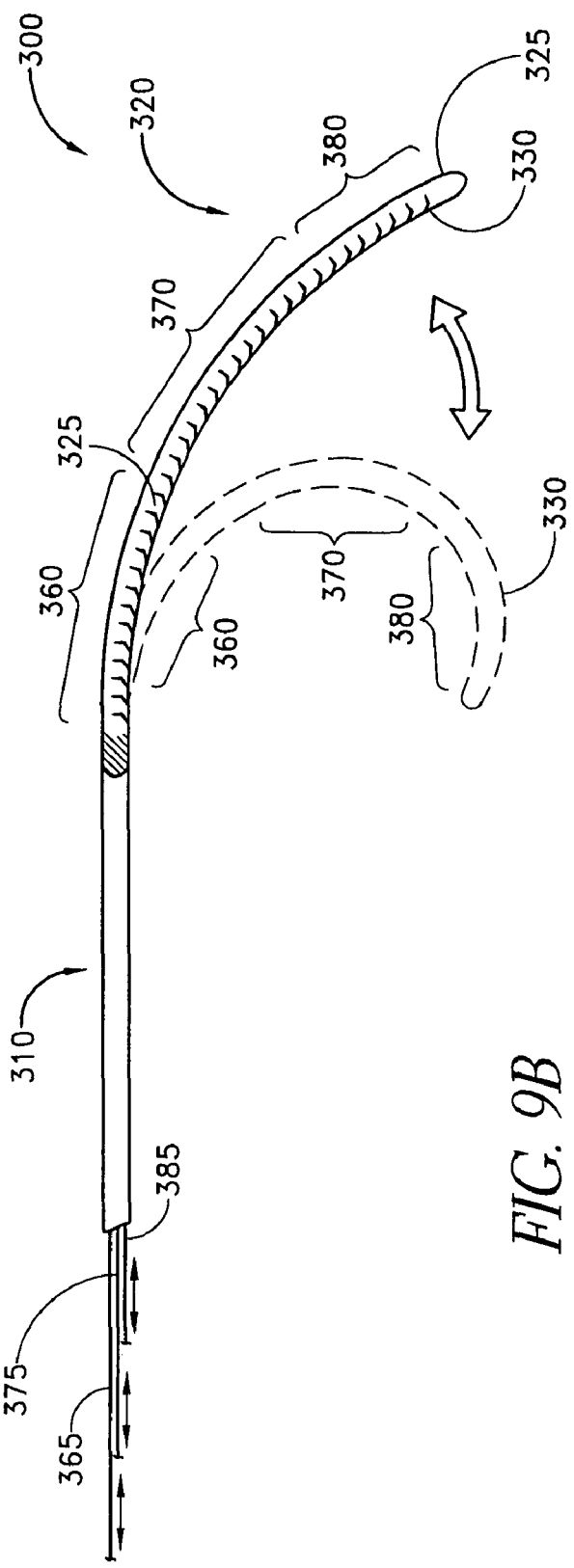

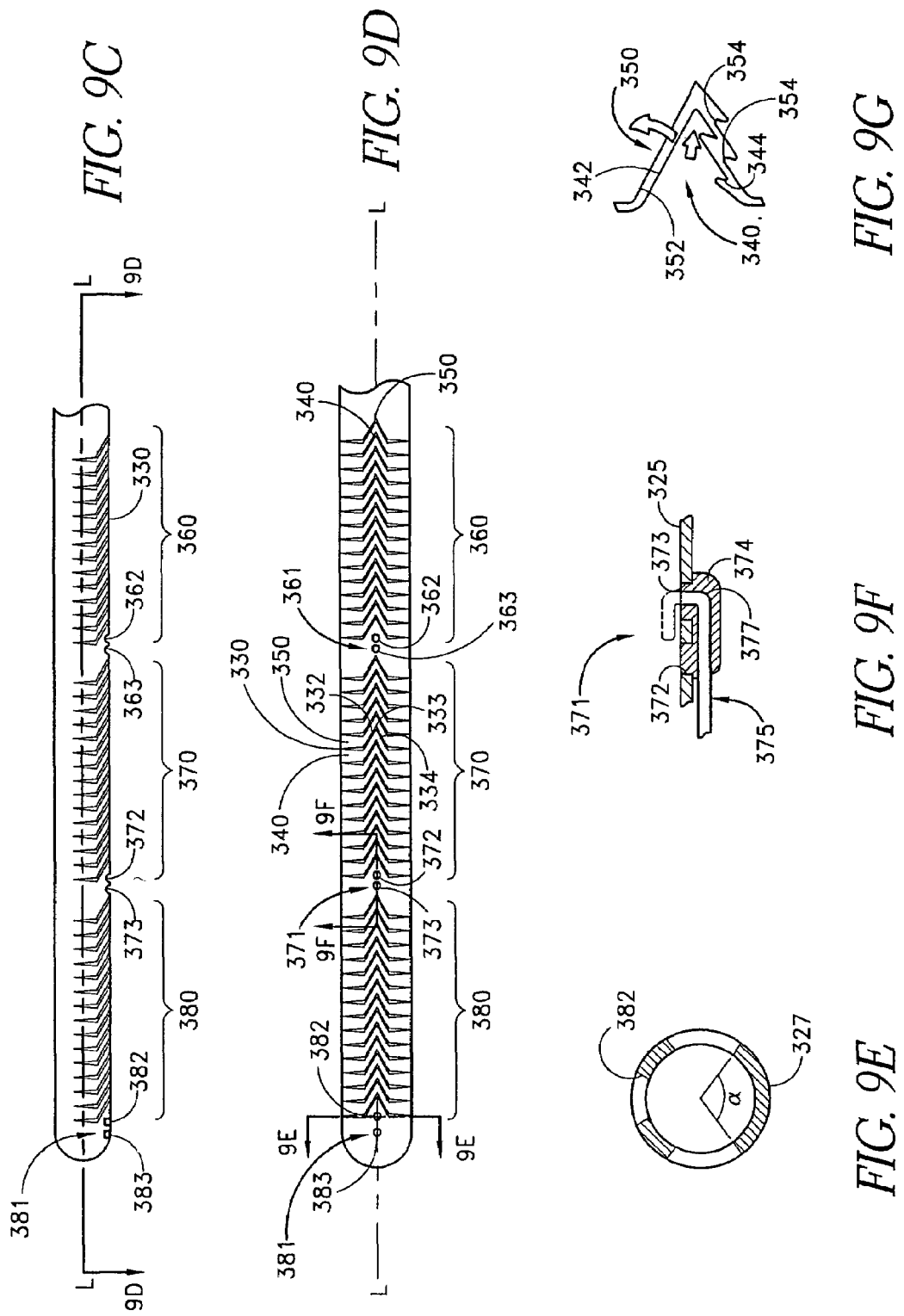

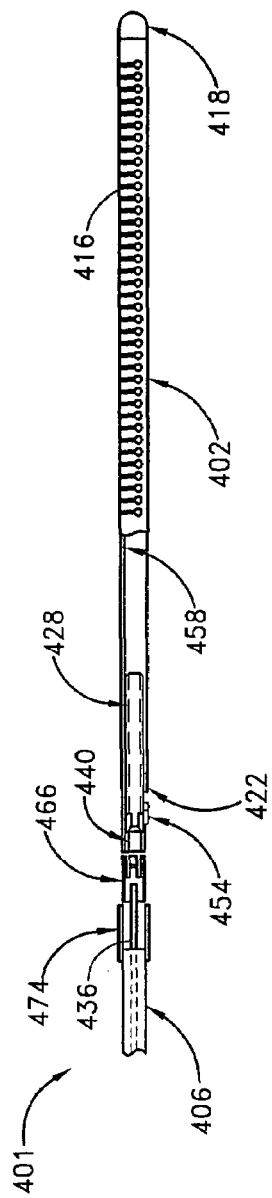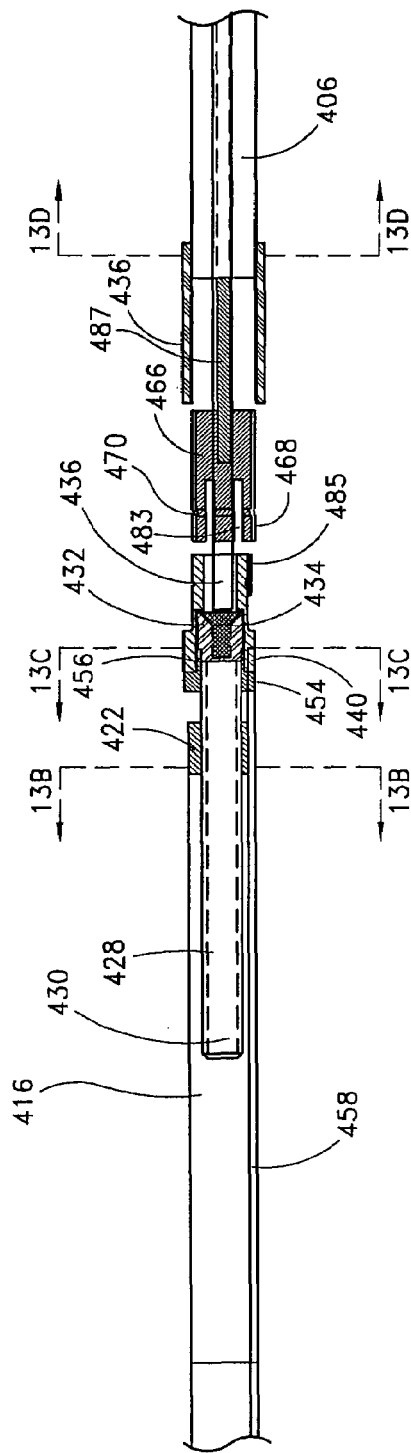
FIG. 12
FIG. 13

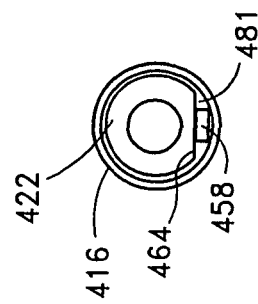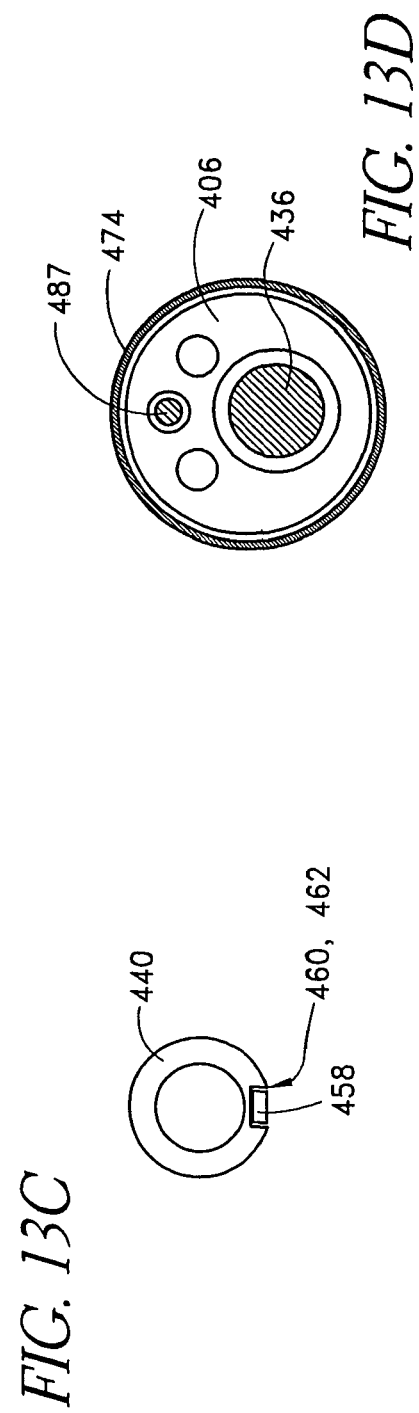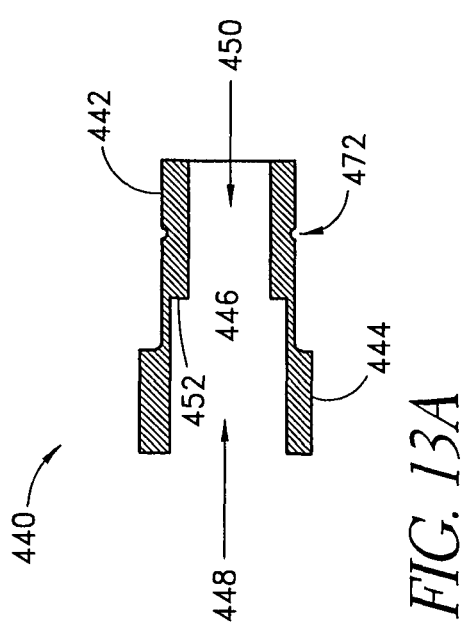

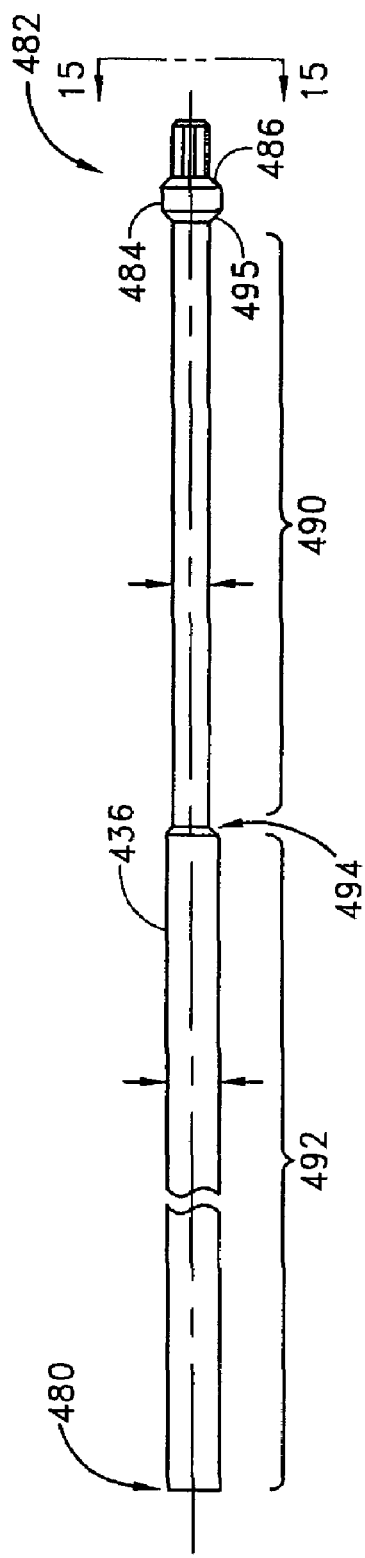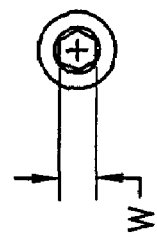
FIG. 14
FIG. 15

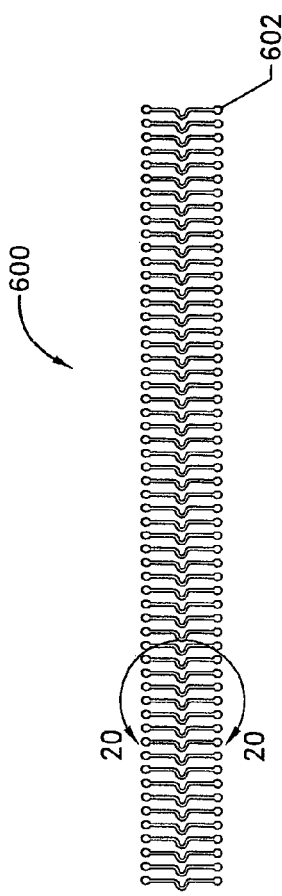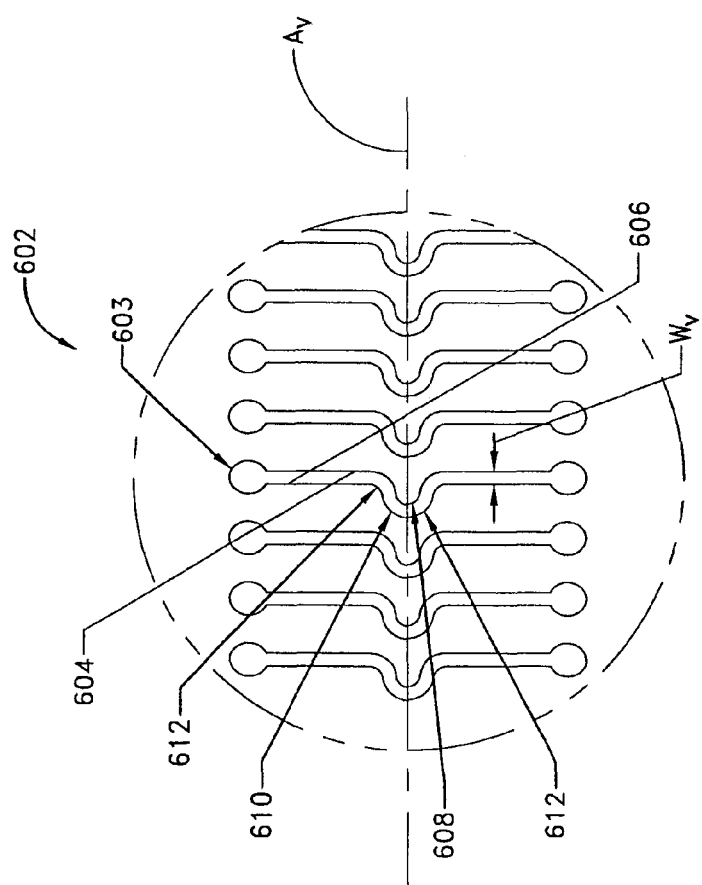

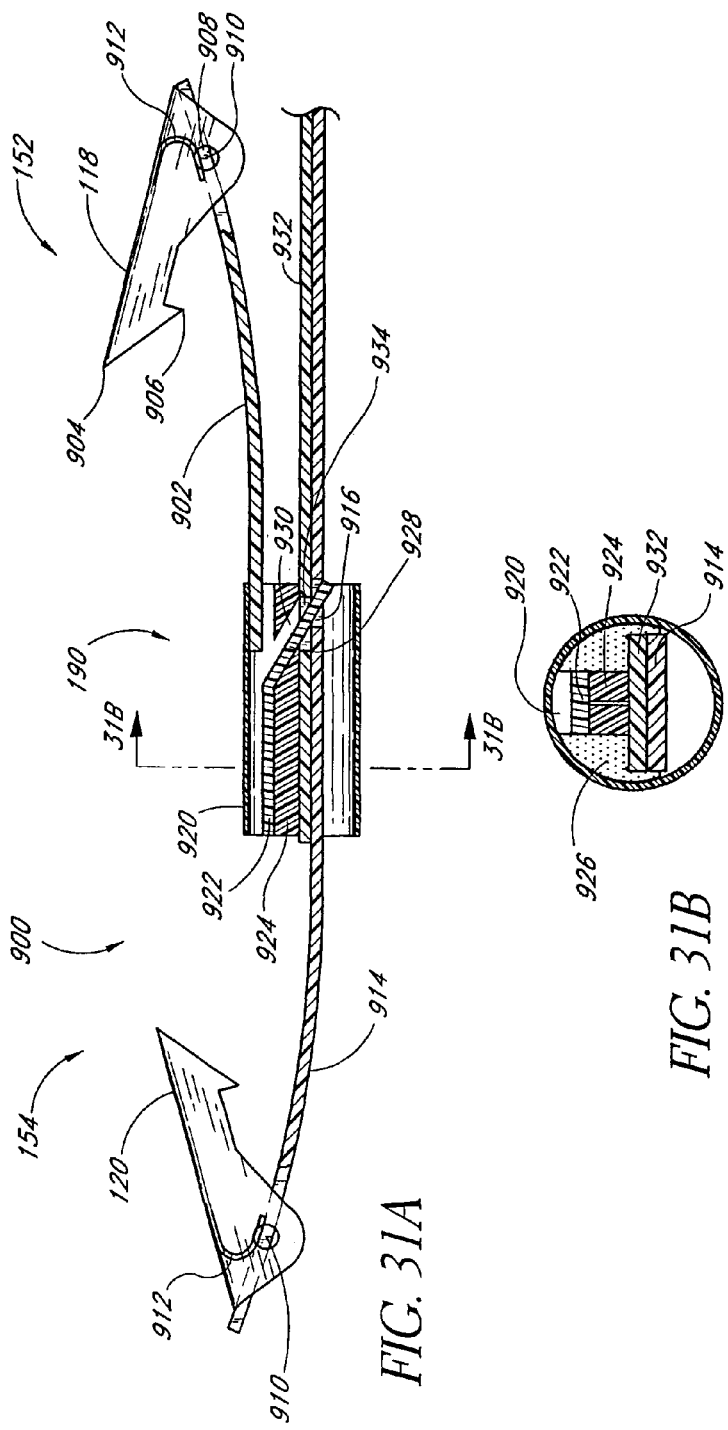
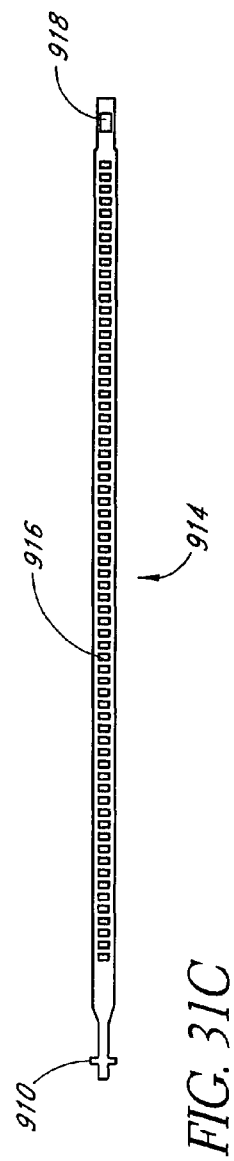
FIG. 31A
FIG. 31B
FIG. 31C

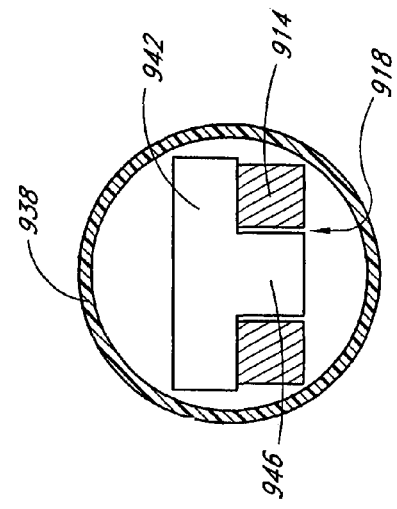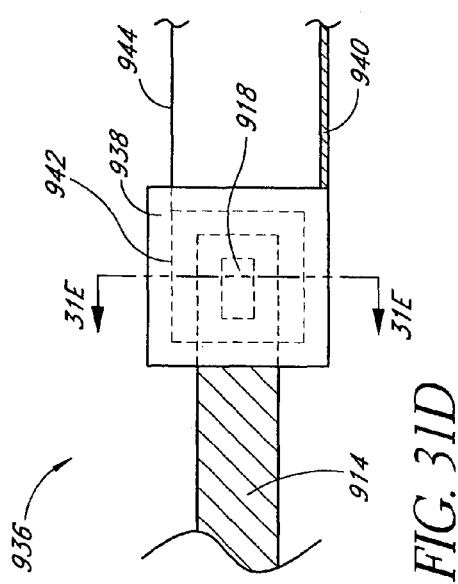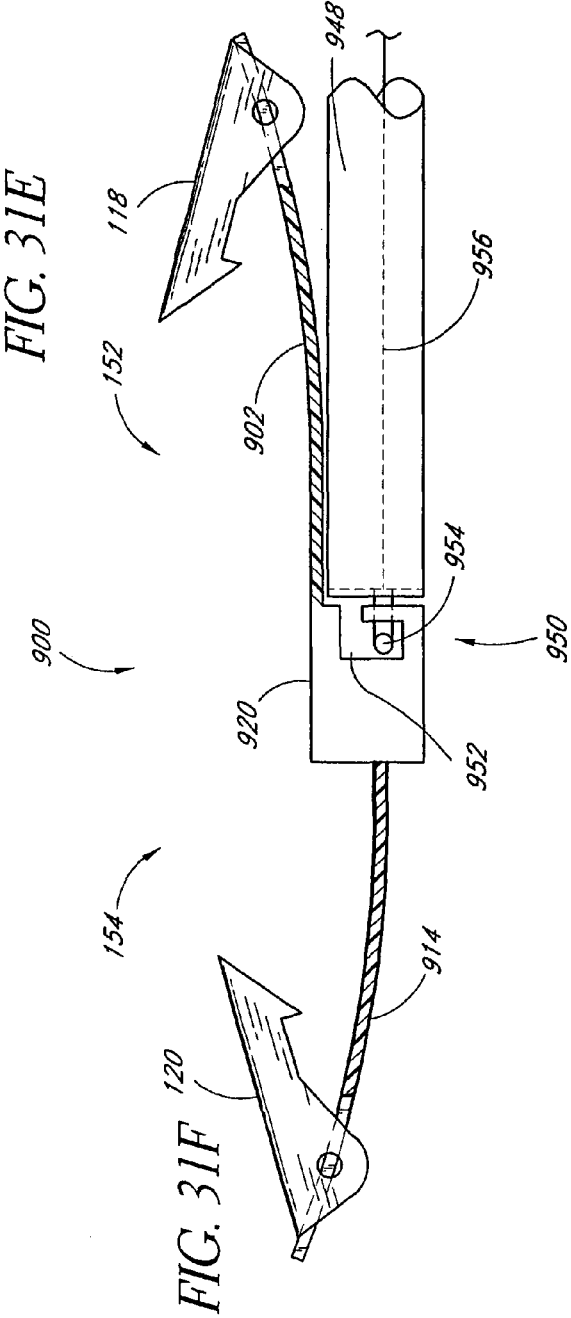

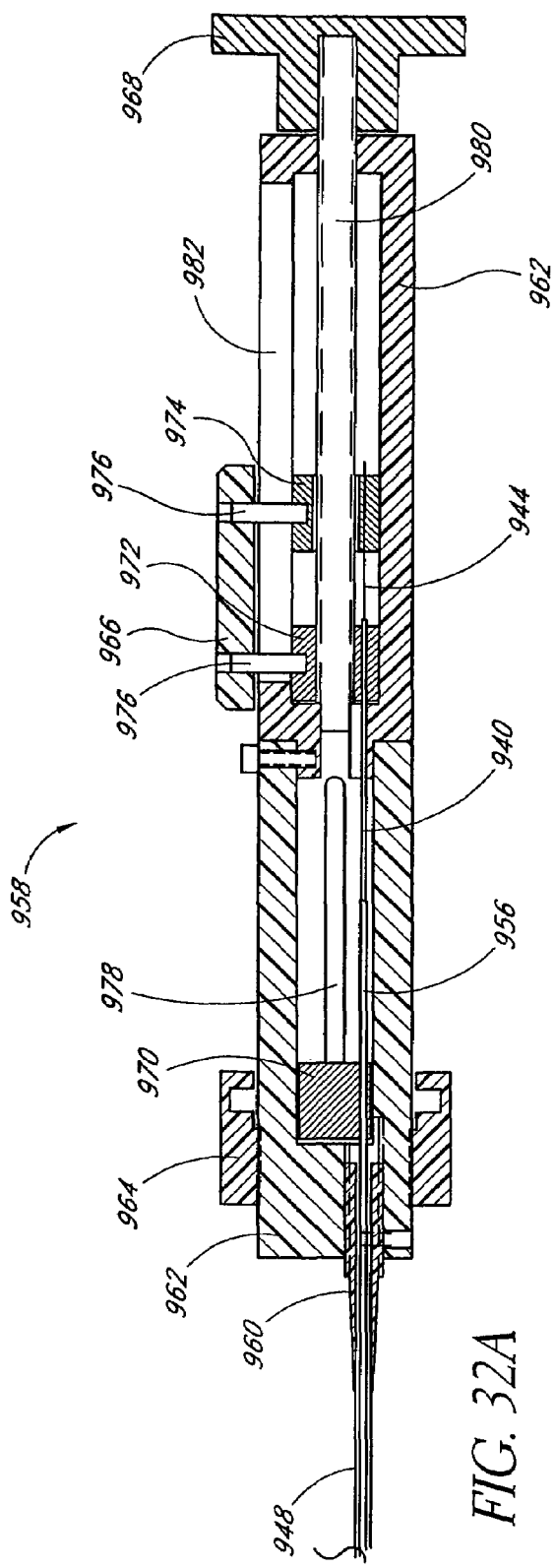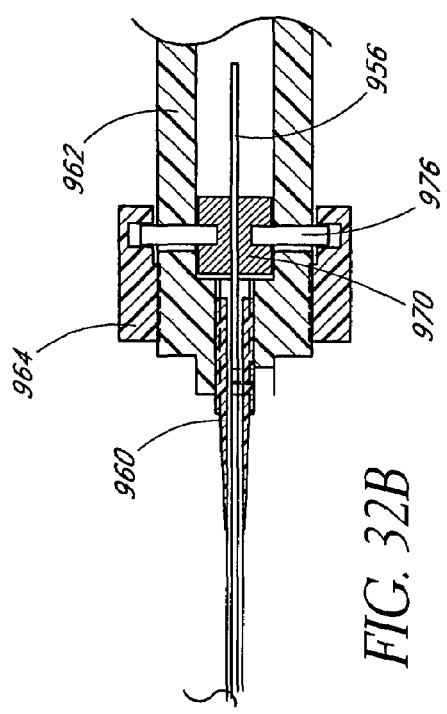
FIG. 32A
FIG. 32B

METHODS AND APPARATUS FOR REMODELING AN EXTRAVASCULAR TISSUE STRUCTURE

RELATED APPLICATIONS

This is a continuation-in-part of U.S. application Ser. No. 10/066,302, filed Jan. 30, 2002, which is a continuation-in-part of U.S. application Ser. No. 09/774,869, filed Jan. 30, 2001, mow U.S. Pat. No. 6,537,314 and which also claims the benefit under 35 U.S.C. §119 to U.S. Provisional Application No. 60/265,995, filed Feb. 1, 2001, the entire disclosures of which are incorporated by reference herein. In addition, this application is a continuation-in-part of U.S. application Ser. No. 09/968,272, filed Oct. 1, 2001, now U.S. Pat. No. 6,709,456 which is a continuation of U.S. application Ser. No. 09/494,233, filed Jan. 31, 2000, U.S. Pat. No. 6,402,781, the entireties of which are incorporated by reference herein. Finally, this application claims priority under 35 U.S.C. §119 to U.S. Provisional Application No. 60/429,281, filed on Nov. 25, 2002, and U.S. Provisional Application No. 60/488,334, filed Jul. 18, 2003, entitled, "REMOTELY ACTIVATED MITRAL ANNULOPLASTY SYSTEM AND METHODS," the entire disclosures of which are expressly incorporated by reference herein.

BACKGROUND OF THE INVENTION

1. Field of the Invention

The present invention relates to intravascular prostheses for remodeling an extravascular anatomical structure.

2. Description of the Related Art

Dilated cardiomyopathy occurs as a consequence of many different disease processes that impair myocardial function, such as coronary artery disease and hypertension. The left ventricle enlarges and the ejection fraction is reduced. The resulting increase in pulmonary venous pressure and reduction in cardiac output cause congestive heart failure. Enlargement of the mitral annulus and left ventricular cavity produce mitral valvular insufficiency. This in turn, causes volume overload that exacerbates the myopathy, leading to a vicious cycle of progressive enlargement and worsening mitral regurgitation.

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques have been developed to repair a diseased or damaged valve. One repair technique which has been shown to be effective in treating incompetence, particularly of the mitral and tricuspid valves, is annuloplasty, in which the effective size of the valve annulus is contracted by attaching a prosthetic annuloplasty ring to the endocardial surface of the heart around the valve annulus. The annuloplasty ring comprises an inner substrate of a metal such as stainless steel or titanium, or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Annuloplasty rings may also be utilized in combination with other repair techniques such as resection, in which a portion of a valve leaflet is excised, the remaining portions of the leaflet are sewn back together, and a prosthetic annuloplasty ring is then attached to the valve annulus to maintain the contracted size of the valve. Other valve repair techniques in current use include commissurotomy (cutting the valve commissures to separate fused valve leaflets), shortening mitral or tricuspid valve chordae tendonae, reattachment of severed mitral or tricuspid valve chordae tendonae or papillary muscle tissue, and decalcification of the valve leaflets or annulus. Annuloplasty rings may be used in conjunction with any repair procedures where contracting or stabilizing the valve annulus might be desirable.

Although mitral valve repair and replacement can successfully treat many patients with mitral valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Of particular interest in the present application are techniques for the repair and replacement of the mitral valve. The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position. An opening, or atriotomy, is then made in the right side of the left atrium, anterior to the right pulmonary veins. The atriotomy is retracted by means of sutures or a retraction device, exposing the mitral valve adjacent to the atriotomy. One of the previously identified techniques may then be used to repair or replace the valve.

An alternative technique for mitral valve access has been used when a median sternotomy and/or rotational manipulation of the heart are inappropriate. In this technique, a thoracotomy is made in the right lateral side of the chest, usually in the region of the fourth or fifth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve through atriotomy for attachment within the heart.

Mitral valve surgery, including mitral annuloplasty, is usually applied to patients with intrinsic disease of the mitral apparatus. As described, above, these patients may have scarring, retraction, tears or fusion of valve leaflets as well as disorders of the subvalvular apparatus. Definitive repair requires direct visualization of the valve.

Patients who develop mitral regurgitation as a result of dilated cardiomyopathy do not always have intrinsic mitral valve disease. Regurgitation occurs as the result of the leaflets being moved back from each other by the dilated annulus. The ventricle enlarges and becomes spherical, pulling the papillary muscles and chordae away from the plane of the valve and further enlarging the regurgitant orifice. In these patients, correction of the regurgitation does not require repair of the valve leaflets themselves, but simply a reduction in the size of the annulus and the sphericity of the left ventricle.

Mitral annuloplasty without repair of the leaflets or chordae has been shown to be effective in patients with dilated cardiomyopathy who are refractory to conventional medical therapy. Dr. Steve Bolling, at The University of Michigan and coworkers have operated on a cohort of such patients with New York Heart Association Class III and IV symptoms. Average symptom severity decreased from 3.9 preoperatively to 2.0 after surgery. Hemodynamics and ejection fraction improved significantly. Other investigators have achieved similar results as well. However, the morbidity, risks and expense of surgical annuloplasty are very high in patients with cardiomyopathy and congestive heart failure. Thus, a variety of new techniques for the treatment of congestive heart failure are being explored as adjuncts to drug therapy.

Several cardiac restraint devices have been described. U.S. Pat. No. 5,702,343 to Alferness discloses a cardiac reinforcement device that is applied as a jacket over the epicardium in order to limit diastolic expansion. However, this requires an open chest operation to implant and does not directly affect the diameter of the mitral annulus. Another approach is disclosed in U.S. Pat. No. 5,961,440 to Schweich, et al., in which tension members are placed through opposite walls of the heart such that they span the ventricle. Less invasive and "minimally" invasive techniques for valve repair and replacement continue to evolve, both on a stopped heart and on a beating heart. These techniques may provide some benefits over open chest procedures, but they are still attended by significant morbidity and mortality risks.

A need therefore remains for methods and devices for treating mitral valvular insufficiency, which are attended by significantly lower morbidity and mortality rates than are the current techniques, and therefore would be well suited to treat patients with dilated cardiomyopathy. Optimally, the procedure can be accomplished through a percutaneous, transluminal approach, using simple, implantable devices which do not depend upon prosthetic valve leaflets or other moving parts.

SUMMARY OF THE INVENTION

There is provided in accordance with one aspect of the present invention a medical apparatus for remodeling a mitral valve annulus adjacent to the coronary sinus. The apparatus comprises an elongate body that includes a proximal end and a distal end. The elongate body is movable from a first, flexible configuration for transluminal delivery to at least a portion of the coronary sinus to a second configuration for remodeling the mitral valve annulus. The medical apparatus also comprises a forming element attached to the elongate body for manipulating the elongate body from the first delivery configuration to the second remodeling configuration. The elongate body in the second, remodeling configuration includes at least a first curve which is concave in a first direction and a second curve which is concave in a second direction.

In one embodiment, the body when in the second configuration comprises a third curve which is concave in the second direction. The elongate body may comprise a tube having a plurality of transverse slots therein. In one embodiment, the medical apparatus further comprises a lock for retaining the body in the second configuration. The apparatus may be movable from the delivery configuration to the remodeling configuration in response to proximal retraction of at least a portion of the forming element. In one embodiment, the apparatus is movable from the implantation configuration to the remodeling configuration in response to distal advancement of at least a portion of the forming element. In one embodiment, at least a first portion of the forming element extends within the body and a second portion of the forming element extends along the outside of the body.

In one embodiment, the medical apparatus further comprises at least one anchor for engaging a site within a vessel. The anchor may comprise at least one barb for piercing the wall of the vessel. In one embodiment, the medical apparatus comprises a first tissue anchor at the proximal end and a second tissue anchor at the distal end. In one embodiment, the apparatus has an axial length of no more than about 10 cm, and in one embodiment, the maximum cross sectional dimension through the apparatus is no more than about 10 mm.

There is provided in accordance with another aspect of the present invention an implant for positioning within a patient. The implant comprises an elongate flexible body having a proximal section, a central section and a distal section. The implant also comprises a forming element extending through at least the proximal and distal sections of the body, and a detachable coupling on the body for removably attaching the body to a deployment catheter. Manipulation of the forming element deflects the central section laterally with respect to at least a portion of the proximal and distal section.

In one embodiment, the body comprises a tubular wall. In another embodiment, the tubular wall is substantially non-compressible along a first side of the central section. The implant may comprise a plurality of voids in the wall along a second side of the central section, thereby permitting axial shortening or elongation of the second side. In one embodiment, at least some of the voids comprise slots through the wall, extending generally transverse to a longitudinal axis. In one embodiment, the implant comprises at least 10 transverse slots in the wall of the second side, and may comprises at least 20 transverse slots in the wall of the second side. The forming element may comprise an axially movable element. In another embodiment, the forming element comprises a pull wire. In one embodiment, manipulation of the forming element introduces a first curve in the central section of the body which is concave in a first direction, and at least a second curve in one of the proximal and distal sections of the body concave in a second direction. In one embodiment, manipulation of the forming element reshapes the body into a "w" configuration.

There is provided in accordance with another aspect of the present invention a method of manipulating the mitral valve comprising the steps of providing a catheter having a prosthesis thereon, the prosthesis having a first tissue anchor and a second tissue anchor, inserting the catheter into the venous system, transluminally advancing the prosthesis into the coronary sinus, attaching the first and second tissue anchors to the wall of the coronary sinus, and manipulating the prosthesis to exert a lateral force on the wall of the coronary sinus in between the first and second tissue anchors.

In one embodiment, the method further comprises the step of percutaneously accessing the venous system prior to the transluminally advancing step. In one embodiment, the accessing step is accomplished by accessing one of the internal jugular, subclavian and femoral veins. In one embodiment, the method further comprises the steps of first measuring the coronary sinus and then selecting an appropriately sized prosthesis prior to the inserting step. In another embodiment, the method further comprises the step of measuring hemodynamic function following the manipulating step. In another embodiment, the method further comprises the step of determining an ongoing drug therapy taking into account the post implantation hemodynamic function.

There is provided in accordance with another aspect of the present invention a method of providing a therapeutic compressive force against a tissue structure which is adjacent to a vessel wall. The method comprises the steps of positioning a device in the vessel; rotating at least a part of a forming element within the device to cause a central portion of the device to travel laterally with respect to a proximal and a distal portion of the device, thereby exerting a force against the adjacent tissue structure; and deploying the device within the vessel.

In one embodiment, the positioning step is accomplished percutaneously. In another embodiment, the tissue structure comprises the mitral valve annulus. In another embodiment, the tissue structure comprises the left ventricle. In yet another embodiment, the vessel comprises a vein.

There is provided in accordance with another aspect of the present invention a method of performing annuloplasty of the mitral valve. The method comprises positioning a prosthesis in a curved portion of the coronary sinus; engaging a proximal tissue anchor and a distal tissue anchor on the device into tissue on an inside radius of the curve; manipulating a first portion of the device with respect to a second portion of the device to provide a compressive force on the inside radius of the curve in between the first and second anchors; and securing the device to maintain the compressive force within the coronary sinus.

In one embodiment, the method further comprises the step of percutaneously accessing the venous system prior to the positioning step. In another embodiment, the accessing step is accomplished by accessing one of the internal jugular, subclavian and femoral veins. In another embodiment, the securing step comprises engaging a first threaded surface with a second threaded surface. In another embodiment, the securing step comprises providing an interference fit. In another embodiment, the securing step comprises providing an adhesive bond. In another embodiment, the securing step comprises providing a knot. In yet another embodiment, the securing step comprises providing a compression fit.

In one embodiment, the method further comprises the steps of first measuring the coronary sinus and then selecting an appropriately sized prosthesis prior to the positioning step. In one embodiment, the method further comprises the step of measuring hemodynamic function following the manipulating step. In yet another embodiment, the method further comprises the step of determining an ongoing drug therapy taking into account the post implantation hemodynamic function.

There is provided in accordance with one aspect of the present invention a method of performing transluminal mitral annuloplasty. The method includes the steps of: providing a catheter, having a prosthesis thereon; inserting the catheter into the venous system; transluminally advancing the prosthesis into the coronary sinus; advancing at least one tissue anchor from a retracted position to an extended position; and manipulating a component of the prosthesis to cause the prosthesis to exert force on the mitral valve annulus.

In one embodiment, the method further comprises the step of percutaneously accessing the venous system prior to the transluminally advancing step. In one embodiment, the accessing step is accomplished by accessing one of the internal jugular, subclavian and femoral veins. In one embodiment, the method further comprises the steps of first measuring the coronary sinus and then selecting an appropriately sized prosthesis prior to the inserting step. The method may further comprise the step of measuring hemodynamic function following the manipulating a component of the prosthesis step. In another embodiment, the method further comprises the step of determining an ongoing drug therapy taking into account the post implantation hemodynamic function. In another embodiment, the advancing at least one tissue anchor step comprises advancing the anchor from an axial orientation to an inclined orientation. In another embodiment, the tissue anchor has a proximal end for piercing tissue and a distal point of attachment to the prosthesis, and the advancing at least one tissue anchor step comprises rotating the anchor about the point of attachment.

In one embodiment, the method comprises advancing at least one tissue anchor to an extended position. The method may also comprise advancing at least two tissue anchors to an extended position. In one embodiment, the manipulating a component of the prosthesis step causes the prosthesis to transform into a curved configuration having a first side facing towards the mitral valve annulus and a second side facing away from the mitral valve annulus. In one embodiment, the method additionally comprises the step of advancing at least two tissue anchors in the direction of the mitral valve annulus. In another embodiment, a first tissue anchor inclines outwardly from the prosthesis in a distal direction and a second tissue anchor inclines outwardly from the prosthesis in a proximal direction.

In another embodiment, the manipulating step comprises axially moving a forming element with respect to the prosthesis, to bend the prosthesis. In another embodiment, the method further comprises the step of locking the prosthesis to retain a force on the annulus following the manipulating step. In one embodiment, the locking step comprises moving an engagement surface from a disengaged configuration to an engaged configuration. In another embodiment, the locking step comprises providing an interference fit. In another embodiment, the locking step is accomplished with a threaded engagement.

In one embodiment, the step of monitoring hemodynamic function is accomplished using transesophageal echo cardiography. In another embodiment, the step of monitoring hemodynamic function is accomplished using surface echo cardiographic imaging. The step of monitoring hemodynamic function may be accomplished using intracardiac echo cardiographic imaging, fluoroscopy with radiocontrast media, or left atrial or pulmonary capillary wedge pressure measurements.

There is provided in accordance with another aspect of the present invention a method of providing a therapeutic compressive force against a tissue structure which is adjacent to a vessel wall, the vessel wall having a first side and a second side. The method comprises the steps of positioning a device in the vessel; advancing a proximal tissue anchor from the device into the first side; advancing a distal tissue anchor from the device into the first side; and manipulating a forming element within the device to cause the device to exert a force against the first side of the wall of the vessel in between the proximal anchor and the distal anchor.

In one embodiment, the positioning step is accomplished percutaneously. In another embodiment, the tissue structure comprises the mitral valve annulus, or the left ventricle. In one embodiment, the vessel comprises a vein.

There is provided in accordance with another aspect of the present invention a method of performing annuloplasty of the mitral valve. The method comprises positioning a prosthesis in the coronary sinus; rotating a first portion of the device with respect to a second portion of the device to cause the device to bend into an arcuate configuration having a proximal concavity and a distal concavity both concave toward the mitral valve and a central concavity concave away from the mitral valve, to provide a compressive force on the mitral valve annulus; and securing the device in the arcuate configuration within the coronary sinus.

In one embodiment, the method further comprises the step of percutaneously accessing the venous system prior to the positioning step. In one embodiment, the accessing step is accomplished by accessing one of the internal jugular, subclavian and femoral veins. In one embodiment, the securing step comprises engaging a first threaded surface with a second threaded surface. In another embodiment, the method further comprises the step of measuring hemodynamic function following the rotating step. In one embodiment, the method further comprises the step of determining an ongoing drug therapy taking into account the post implantation hemodynamic function.

There is provided in accordance with another aspect of the present invention a medical apparatus for remodeling a mitral valve annulus adjacent to the coronary sinus. The apparatus comprises an elongate body, having a proximal end region and a distal end region, each of the proximal and distal end regions configured to move between a first, flexible configuration for transluminal delivery to at least a portion of the coronary sinus and a second remodeling configuration in which each of the proximal and distal end regions forms a curve which is open in the direction of the mitral valve; and a forming element for manipulating the elongate body between the first transluminal configuration and the second remodeling configuration.

In one embodiment, the elongate body comprises a tube having a plurality of transverse slots therein. In another embodiment, the elongate body transforms into the remodeling configuration by changing the width of the slots. In another embodiment, the medical apparatus further comprises a coating on the body. In yet another embodiment, the apparatus is movable from the implantation configuration to the remodeling configuration in response to proximal retraction of the forming element.

In one embodiment, the apparatus is movable from the implantation configuration to the remodeling configuration in response to distal advancement of the forming element. In another embodiment, the apparatus is movable from the implantation configuration to the remodeling configuration in response to rotation of a threaded shaft. In another embodiment, the medical apparatus further comprises an anchor for retaining the apparatus at a deployment site within a vessel. In yet another embodiment, the anchor comprises a distal extension of the apparatus, a surface structure for engaging the wall of the vessel, or at least one barb for piercing the wall of the vessel. In one embodiment, the medical apparatus comprises a first barb on the proximal end region and a second barb on the distal end region.

There is provided in accordance with another aspect of the present invention an implant for positioning within a patient. In one embodiment, the implant comprises an elongate flexible body having a proximal end and a distal end, and a longitudinal axis extending therebetween, and first and second opposing sides extending along the implant body; the first side having at least one fixed axial length section, and the second side having at least one fixed axial length section, axially offset from the fixed axial length section on the first side; at least a first forming element extending through the body to a distal point of attachment to the body; and a detachable coupling on a proximal portion of the body, for removably attaching the body to a deployment catheter; wherein manipulation of the first forming element deflects at least a first portion of the body away from the longitudinal axis.

In one embodiment, the body comprises a tubular wall. In another embodiment, the implant includes a plurality of voids in the wall along the second side, opposing the fixed axial length section on the first side, thereby permitting adjustment of the axial length of the second side. In another embodiment, at least some of the voids comprise slots through the wall, extending generally transverse to the longitudinal axis. In another embodiment, the implant comprises at least 10 transverse slots in the wall of the second side, or at least 20 transverse slots in the wall of the second side. In one embodiment, the first forming element comprises an axially movable element or a pull wire.

There is provided in accordance with one aspect of the present invention a system for remodeling a mitral valve annulus. The system includes a delivery catheter, an implant and a control on the catheter. The implant is detachably carried by the delivery catheter. The implant is reversibly movable between a first, flexible configuration for delivery to a site adjacent the annulus of the mitral valve and a second, rigid configuration for remodeling the mitral valve annulus. The control on the catheter is for reversibly transforming the implant between the first flexible configuration and the second remodeling configuration.

In one embodiment, the implant comprises an arc when in the remodeling configuration. In another embodiment, a best fit constant radius curve corresponding to the arc has a radius within the range of from about 10 mm to about 20 mm. In another embodiment, the implant comprises a compound curve when in the remodeling configuration. In one embodiment, the compound curve comprises a "w" configuration.

In one embodiment, the system further comprises a coating on the implant. In another embodiment, the system further comprises an anchor for retaining the implant at a deployment site. In one embodiment, the anchor comprises a distal extension of the implant, a friction enhancing surface structure for engaging adjacent tissue, or at least one barb for piercing the wall of the vessel. In one embodiment, the barb is moveable between an axial orientation and an inclined orientation.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 4 is a segmented view of the assembly shown in FIG. 3, and shows an enlarged fragmentary view of an implant attachment region of the assembly.

FIG. 5 shows a transverse cross-sectional view taken along 5—5 in FIG. 4.

FIG. 6 shows a perspective view of a proximal region of an implant according to the invention.

FIG. 7 shows a partially cross-sectioned side view of a region of a device assembly similar to that shown in FIG. 6.

FIGS. 9A–B show side elevational schematic views of a distal end portion of a delivery assembly coupled to an elongate body, and show the elongate body during two modes of operation, respectively.

FIG. 9C shows a side elevational view of a portion of the implant shown in FIG. 9A.

FIG. 9D shows a cross sectional view taken along line 9D—9D in FIG. 9C, showing an interlocking transverse slot pattern.

FIG. 9E shows a cross-sectional view through the line 9E—9E of FIG. 9D.

FIG. 9F is a fragmentary cross sectional view of a connection between a forming or deflection element and an elongate body.

FIG. 9G shows a fragmentary schematic view of two interlocking segments according to one specific mode for the elongate body shown in FIGS. 9A–F.

FIG. 12 is an enlarged view of a portion of the medical device of FIG. 10, including the implant and a connection assembly for removably connecting the implant to the delivery assembly.

FIG. 13 is an enlarged view of the connection assembly of the medical device of FIG. 12.

FIG. 13A is a cross section view of the male connector of FIG. 13.

FIG. 13B is a cross section view taken along view line 13B—13B of FIG. 13.

FIG. 13C is a partial cross section view taken along view line 13C—13C of FIG. 13.

FIG. 13D is a cross section view taken along view line 13D—13D of FIG. 13.

FIG. 14 is a plan view of a rotational driver of the delivery assembly of the medical device of FIG. 10, viewed apart from the medical device.

FIG. 15 is an end elevational view of a hex-shaped distal end of the driver of FIG. 14, taken along the view line 15—15 of FIG. 14.

FIG. 19 is a plan view of a slot pattern for an implant such as that of FIG. 10.

FIG. 20 is an enlarged view of the slot arrangement of FIG. 19.

FIG. 31A is a side elevational view of an alternative implant in accordance with the present invention.

FIG. 31B is a cross-sectional view taken along line 31B—31B of FIG. 31A.

FIG. 31C is a plan view of a ratchet strip for use with the implant of FIGS. 31A and 31B.

FIG. 31D is a plan view of a disconnect sub-assembly for use with the ratchet strip of FIGS. 31A–C.

FIG. 31E is a cross-sectional view taken along line 31E—31E in FIG. 31D.

FIG. 31F is a plan view showing the catheter coupling of the implant of FIGS. 31A–B FIG. 32A is a cross-sectional view of a proximal deployment handpiece.

FIG. 32B is a partial cross-sectional view of the proximal deployment handpiece of FIG. 32A rotated 90 degrees.

DETAILED DESCRIPTION OF THE PREFERRED EMBODIMENT

Preferred embodiments of the present invention include a method and apparatus for performing mitral annuloplasty and remodeling of the left ventricle using a device that may be introduced percutaneously, and placed within the coronary venous system of the heart. The device exerts compressive force on the mitral annulus and left ventricle, reducing the severity of mitral regurgitation and the size of the left ventricular cavity. The device thus enables reduction of the mitral annulus and constraint of the diastolic expansion of the left ventricle yet without the morbidity and other risks associated with open chest surgery. Additional details are disclosed in the parent application Ser. No. 10/066,302, filed on Jan. 30, 2002, the disclosure of which is incorporated in its entirety herein by reference.

The present inventors have determined that the coronary sinus and veins provide an ideal conduit for the positioning of an intravascular prosthesis, or implant, for remodeling the mitral annulus, since they are positioned adjacent the mitral annulus and interventricular septum. As used herein, the term "implant" is a broad term, and should not be limited to a permanently introduced structure or device, but could additionally be a temporarily introduced device. The coronary sinus is contained within the atrioventricular groove, and is in close proximity to the posterior, lateral and anterior aspects of the mitral annulus. The coronary sinus and coronary veins are cannulated currently during any of a variety of percutaneous transvenous diagnostic and therapeutic procedures. Permanent placement of pacemaker and defibrillator leads within the coronary sinus and veins is both safe and well tolerated.

The annuloplasty system consists of several components. Desirably, there is a delivery system intended to be introduced percutaneously into a central vein such as the internal jugular, subclavian or femoral veins and to cannulate the coronary sinus. The implant of the present invention is deployed from the delivery system, preferably a delivery catheter, into the coronary venous system or into a position within or adjacent the myocardium, to influence the annulus of the mitral valve. Additional tools may be placed through or along the delivery catheter to position the device, apply elements in place, and to control and/or cut tensioning elements (if provided) from the delivery system, as will be discussed in detail below.

Figure 1:
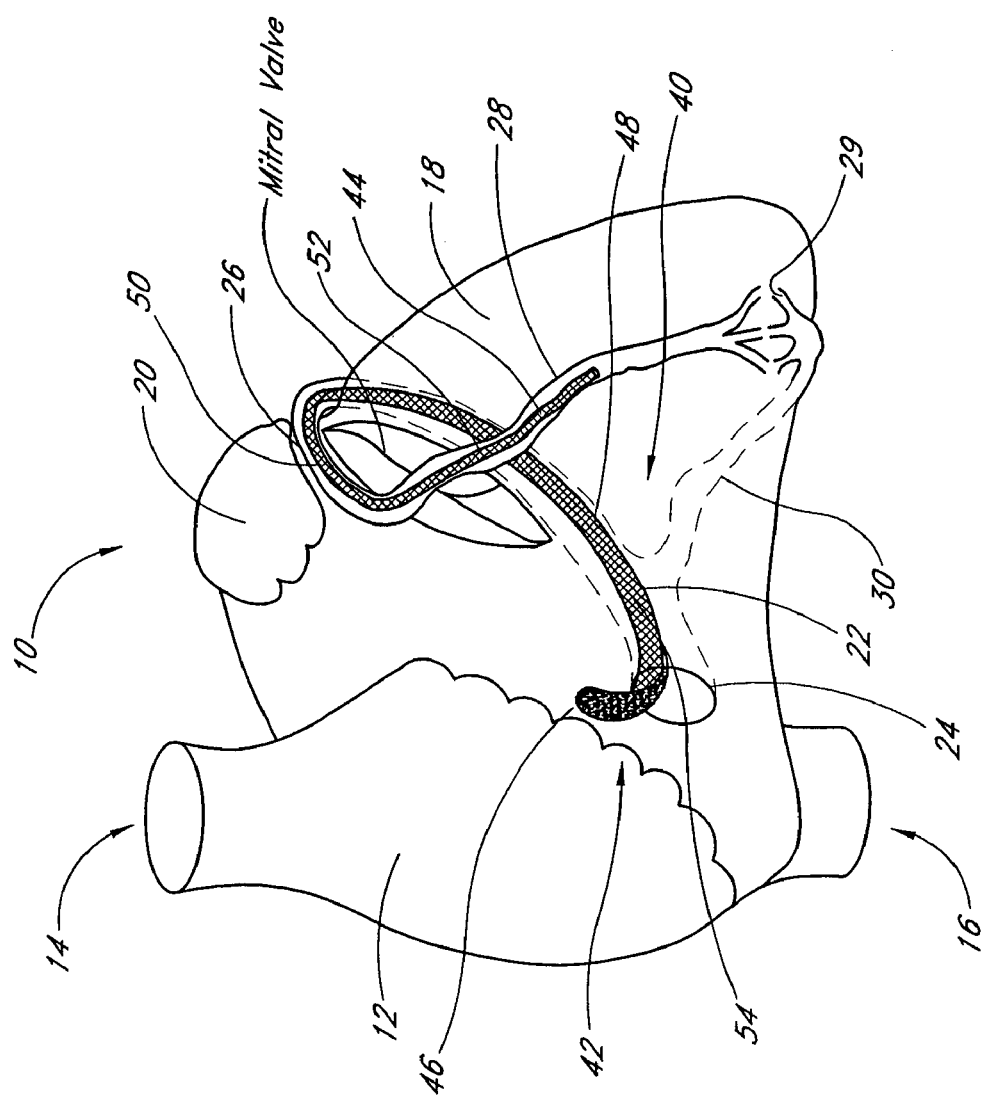
FIG. 1 is a schematic illustration of the heart, showing one embodiment of the mitral annuloplasty device of the present invention deployed within the coronary venous system.

Referring to FIG. 1, there is illustrated a schematic view of the heart 10, having a preferred embodiment of a mitral annuloplasty and cardiac reinforcement device 40 positioned therein. The heart 10 generally comprises a right atrium 12, in communication with the superior vena cava 14 and inferior vena cava 16. The left ventricle 18 is positioned below the left atrial appendage 20. Relevant portions of the coronary vasculature include the coronary sinus 22, which extends from the ostium 24 to the junction 26 of the coronary sinus and the great cardiac vein 28. There may be anastomotic connections 29 between the great cardiac vein 28 and the middle cardiac vein 30, as is well understood in the art.

One embodiment of a mitral annuloplasty and cardiac reinforcement device 40 is illustrated generally in the coronary sinus 22. In particular, the device 40 extends from a proximal end 42 to a distal end 44. The proximal end 42 lies against the posterior aspect of the interatrial septum 46. The midportion 48 of the device 40 is positioned within the coronary sinus 22. The transitional section 50 of the device 40 lies at the junction 26 of the coronary sinus 22 and the great cardiac vein 28. The distal end 44 of the device 40 is lodged in the great cardiac vein 28.

The transitional region 50 is designed to reside in the proximal portion of the great cardiac vein 28. By deflecting out of a plane defined by the coronary sinus 22, it serves as an anchor 52 and prevents the device 40 from slipping out of the coronary sinus 22 when tension is applied. This embodiment of an anchor 52 is, preferably, very flaccid and flexible, thereby minimizing the risk of erosion of the device 40 through the wall of the great cardiac vein or other aspect of the coronary venous system. The proximal end 42 of the device 40 lies outside the ostium 24 of the coronary sinus 22 and is desirably curved upward so as to anchor against the posterior aspect of the interatrial septum 46. Advantageously, the proximal end 42 of the illustrated device 40 is semicircular in shape and elliptical in profile so that no edges will promote erosion of adjacent tissue.

As an alternative anchor 52 to the distal extension of the device 40, any of a variety of structures may be provided. In general, the deployed device 40 will contact the wall of the coronary sinus 22 along the inside radius of its arcuate path. Thus, a tissue contacting surface 54 on the concave side of the deployed device 40 may be provided with any of a variety of friction enhancing surface structures, such as a plurality of transverse ridges, teeth or other projections, or modified surface textures to enhance friction. Alternatively, tissue engaging or piercing structures such as barbs may be provided on the surface 54 to engage the wall of the coronary sinus 22 to resist movement of the device 40, as will be discussed.

While use of such structures as anchors may provide some benefit in certain applications, embodiments herein shown and described are believed to be particularly useful in one aspect specifically because they operate without the need for such aggressive tissue engagement. It will be apparent to one of ordinary skill based upon this disclosure that the present embodiments provide independent device manipulation and shape control that allow for sufficient forces to be applied to the mitral valve without requiring the possibly harmful effects of puncturing and grabbing tissue within the sinus for the remodeling process. In one regard, the independent action of a barbless design allows for adjustment in both the tightening and loosening directions with reduced risk of significant tissue damage or erosion. In another regard, devices 40 according to at least certain embodiments beneficially maintains its length throughout its modified range of shapes while the sinus and adjacent valve annulus reduce their dimensions under the force of remodeling. In still a further regard, the independent action and lack of tissue piercing and grabbing anchors allow for the device to be removed from the patient after initial implantation within the sinus, such as for example in the event of complications or in applications intended to be temporary remedial measures, such as for bridging a patient to surgery. Further to this regard, various shapes and sizes of devices may be required in a given patient before the appropriate one is found according to the observed in vivo response to implantation.

The specific dimensions, construction details and materials for the mitral annuloplasty and cardiac reinforcement device 40 can be varied widely, as will be appreciated by those of skill in the art in view of the disclosure herein. For example, dimensional adjustments may be made to accommodate different anatomical sizes and configurations. Materials and construction details can be varied to accommodate different tensioning mechanisms and other considerations.

In general, the device 40 defines an overall length from proximal end 42 to distal end 44. Preferably, the length is within the range of from about 2 cm to about 10 cm in an embodiment such as that illustrated in FIG. 2 in which the anchor 52 comprises a distal extension of the body 66 for lodging within the great cardiac vein 28. One embodiment of the device 40 includes an elongate flexible body 66 about eight centimeters in length. In such an embodiment, the body 66 may be elliptical in cross section so that it will bend in a single plane when force is applied to the tensioning element within it, as will be discussed below. Distally the device 40 tapers and transitions to a round cross-section.

Figure 2A:
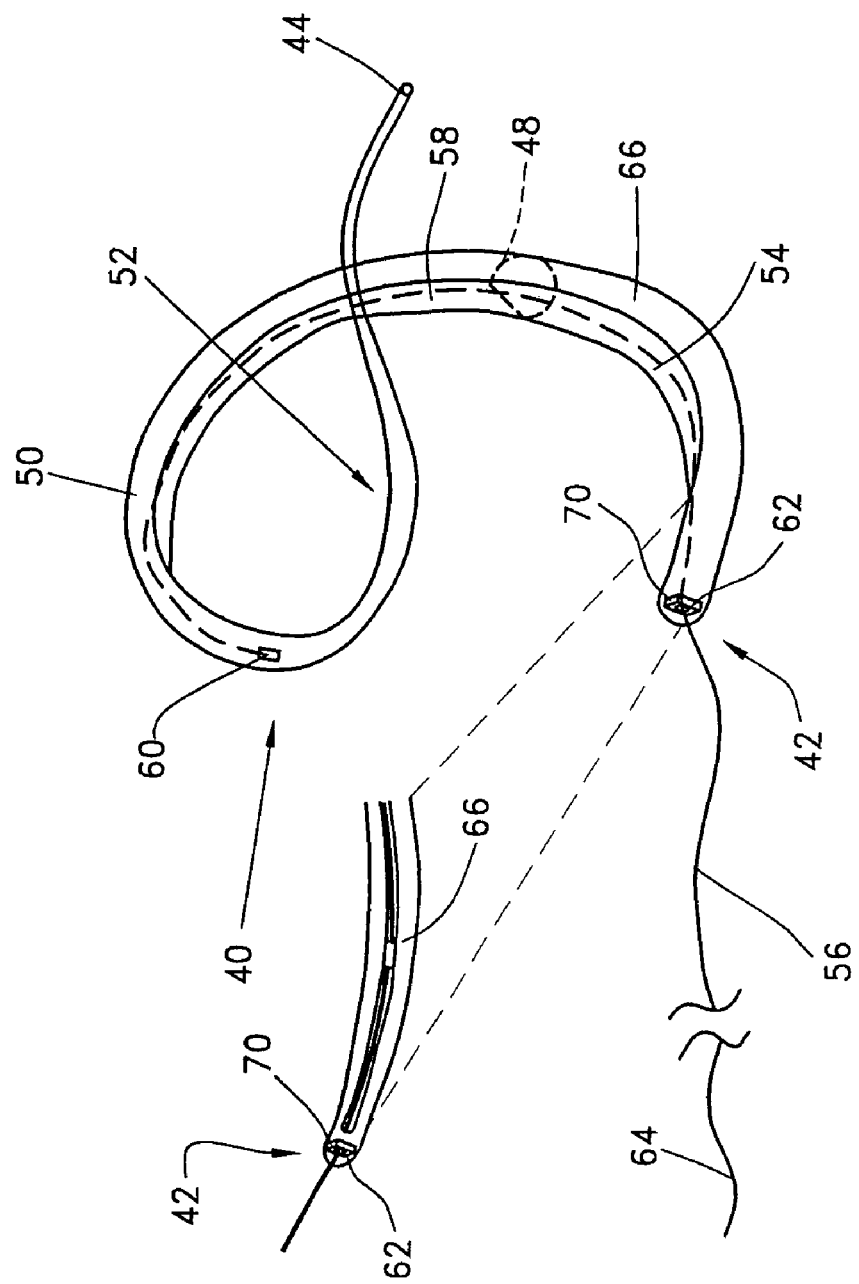
FIGS. 2A and 2B are schematic illustrations of the mitral annuloplasty device shown in FIG. 1, in second and first configurations.
Figure 2B:
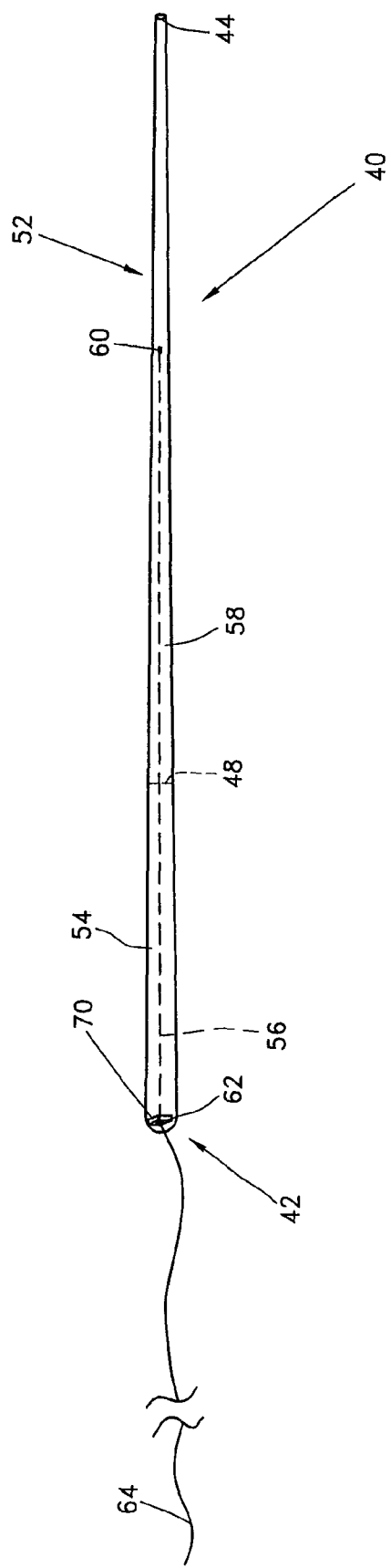

Referring to FIGS. 2A–B, there is illustrated an embodiment of the device 40 having a forming element 56, such as a wire, therein. Manipulation of the forming element 56 allows the device to be moved from a flexible orientation to enable percutaneous insertion into the vascular system and navigation into the coronary sinus (FIG. 2B), to an arcuate configuration for compressing at least a portion of the mitral annulus (FIG. 2A). The device 40 may be advanced from the first, flexible configuration to the second, arcuate configuration by either axial proximal retraction or distal advancement of the forming element 56 with respect to the body 66, depending upon the particular design.

In general, the device 40 comprises an elongate flexible support 58, extending from a proximal end 42 at least as far as a point of attachment 60. The support 58 may be a portion of the body 66 or may be a distinct component as will be discussed. The support 58 has a fixed length, and is substantially axially non-compressible and non-expandable. Thus, proximal axial retraction of the forming element 56 relative to the proximal end of the support 58 will desirably cause the support 58 to deflect in a first direction, tending to bend the body 66 about an axis transverse to the longitudinal axis of the body 66. Distal axial advancement of the forming element 56 with respect to the support 58 will cause lateral deflection of the support 58 in a second direction, tending to permit the body 66 to straighten due to the inherent resiliency of the support 58. This basic steering configuration can be embodied in many forms, which can be optimized by those of skill in the art to suit a particular construction for the body 66 depending upon the desired dimensions and clinical performance.

The forming element 56 extends from the proximal end 42 through the device 40 to the point of attachment 60. At the point of attachment 60, the forming element 56 is mechanically coupled, and preferably, directly coupled to the support 58. Alternatively, other suitable methods of attachment may be used. A proximal extension 64 of the forming element 56 extends from the proximal end 42 of the device 40, such as through an aperture 62. Proximal retraction of the forming element 56 through the aperture 62 causes the device 40 to bend from an implantation, or delivery orientation, for navigating the coronary vasculature during implantation, to a formed, or remodeling orientation for compression and constraint of the coronary sinus 22 and adjacent structures.

In the formed, remodeling orientation, the device 40 preferably provides a compressive force against the mitral annulus as has been discussed. This is desirably accomplished by forming the device into an arcuate configuration. Generally, the best fit curve of constant radius to which the formed device conforms has a radius within the range of from about 1.0 cm to about 2.0 cm. The forming element may comprise any of a variety of materials and constructions, such as a polymeric or metal wire or strand, a multi-filament braided or woven line, a metal or polymeric ribbon, or other structure capable of retaining the device 40 under tension in the coronary sinus 22.

The device 40 further comprises a support 58, which may be the body 66 of the device 40 or a separate element positioned therein. In an embodiment in which the support 58 is a separate element contained within the device 40, support 58 may comprise any of a variety of generally axially non-compressible elements such as a metal or polymeric wire or column, ribbon, or "bottomed out" (e.g., fully compressed) spring which facilitates lateral bending but inhibits axial compression upon proximal retraction of forming element 56. A metal ribbon comprising stainless steel, nitinol, or other known materials may be desired in certain embodiments, due to its ability to influence the plane of curvature of the device 40 when in the formed orientation.

In the presently illustrated embodiment, the proximal extension 64 of the forming element 56 extends proximally throughout the length of a deployment catheter, to a control or free end which remains outside of the patient during the deployment procedure. Following placement of the device 40 in the coronary sinus, proximal traction on the proximal extension 64 will reconfigure the device 40 into the formed orientation within the coronary sinus, as will be discussed in connection with the method of use of preferred embodiments. After a sufficient tension has been placed on the coronary sinus 22, the forming element 56 is preferably locked in a fixed axial position with respect to the device 40, to resist distal movement of the forming element 56 through aperture 62. Any of a variety of suitable lock arrangements may be provided. Preferably, the lock 70 is provided on or near the proximal end 42, and, in particular, at or about the aperture 62. The lock may comprise any of a variety of structures, such as a suture knot, locking clamp or ring, an interference fit, ratchet and pawl structures, threaded engagement, an adhesive bond, or a compression fit, as will be apparent to those of skill in the art in view of the disclosure herein.

The lock 70 (on any of the embodiments herein) may be initially disengaged, so that the forming element 56 may be retracted or advanced freely through the aperture 62 while the physician adjusts the tension on the device 40. After the desired tension is achieved, the lock 70 is activated to engage the forming element in a manner which will depend upon the lock design. Alternatively, the lock 70 may be biased into an engaged configuration, such as with ratchet or cam structures, so that the forming element can only be retracted proximally. Preferably, however, the lock will allow the forming element to be released so that the physician can release tension on the device 40 in the event of momentary over tightening.

The forming element 56 and support 58, with or without the tubular body discussed below, may be surrounded by a tubular jacket of ePTFE or a polyester fabric such as DACRON, or other material which is wrapped or stitched onto the forming element 56 to produce the final device 40. As a further alternative, the subassembly which includes the forming element 56, and, if present, support 58 may be positioned within a suitable length of tubing formed such as by extrusion. The tubing may be drawn down to a reduced diameter at the distal end 44. Additional post extrusion steps may be used to produce the desired cross-sectional configuration. Manufacturing techniques for the present invention will be apparent to those of skill in the art in view of the disclosure herein.

Any of a variety of additional features may be added to the device 40, depending upon the desired clinical performance. For example, the outside surface of the body 66 may be provided with any of a variety of coatings, such as poly-paraxylene, sold under the trademark PARALENE, PTFE or others to improve lubricity; heparin or other antithrombogenic agents; elastomers such as silicone, neoprene, latex or others to soften the surface and reduce the risk of trauma to the vascular intima, and the like. Adhesion enhancing surfaces may be provided, such as ePTFE patches or jackets, to promote cellular ingrowth for long term anchoring. In addition, depending upon the deployment system design, the body 66 may be provided with a guidewire lumen extending axially therethrough, to allow the body 66 to be advanced distally over a guidewire during placement at the treatment site.

The device 40 may be implanted within the coronary sinus 22 either through direct surgical (e.g., thoracotomy, with or without sternotomy) access, such as in combination with another surgical procedure, via port access, or remotely by way of a percutaneous or surgical cut down access to the venous system. Preferably, the device 40 is implanted in a transluminal procedure, such as by way of a percutaneous access at one of the internal jugular, subclavian, or femoral veins.

Figure 3:
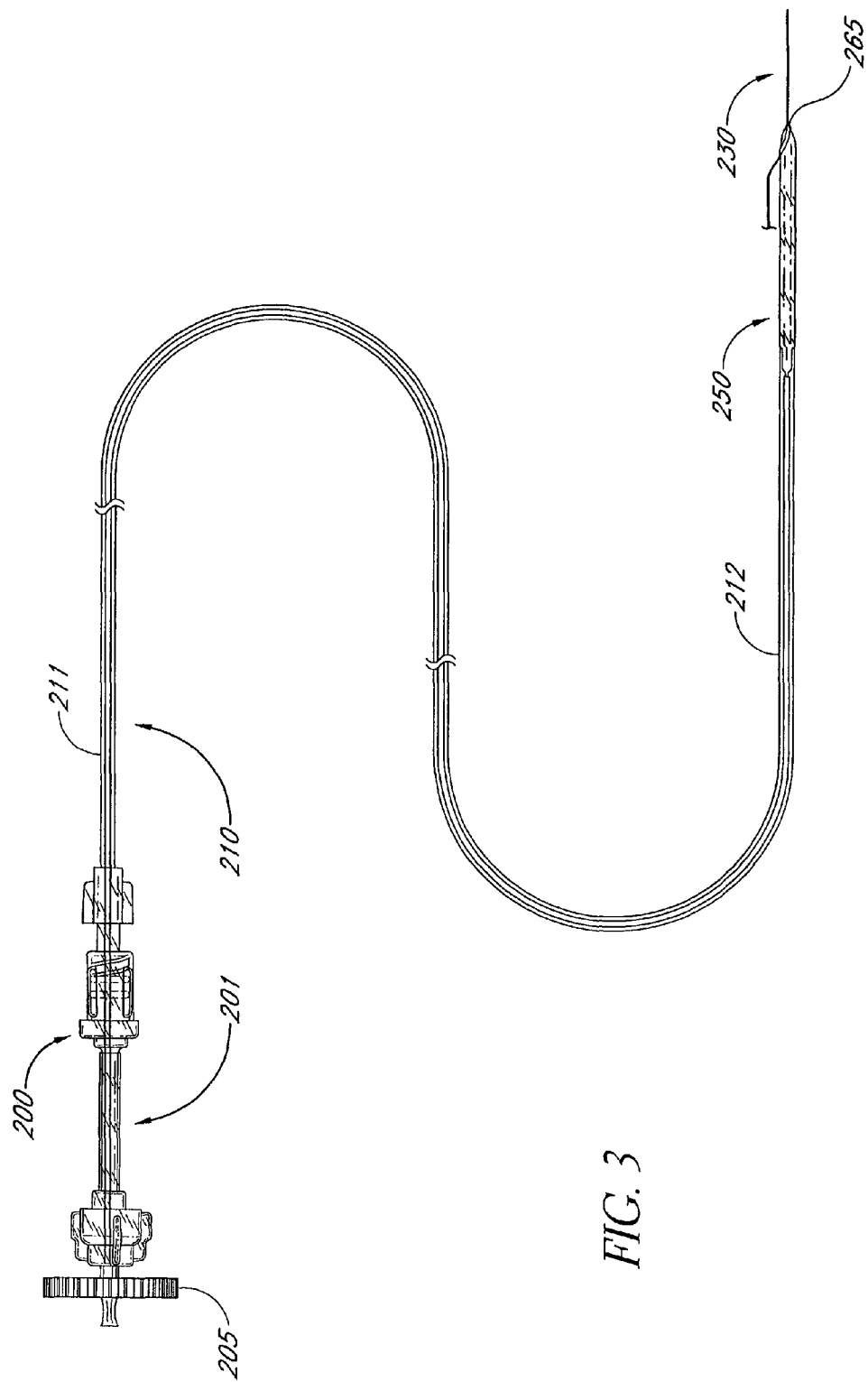
FIG. 3 is a side elevational view of an implant and deployment catheter according to the invention.

FIGS. 3–8B illustrate an exemplary device assembly 200. In general, FIG. 3 is an overall view of assembly 200 that includes a delivery assembly 210 engaged to a prosthesis, or implant 250. According to similar overall delivery systems and methods elsewhere herein described, prosthesis 250 is adapted to be delivered in a first condition and shape into a vessel at least in part by manipulation of delivery assembly 210. Once in the desired region of the target vessel, prosthesis 250 is adapted to be adjusted to a second condition and shape within the vessel in order to influence an adjacent tissue structure. As also elsewhere herein described, a particularly beneficial mode of such operation places the prosthesis 250 within a coronary sinus for the purpose of influencing a mitral valve annulus, more specifically in order to influence the shape of the annulus in order to reduce mitral valve regurgitation.

FIGS. 4–7 show the proximal aspects of device assembly 200, and in particular various details for delivery assembly 210 that includes an outer member 215 that is preferably tubular with an inner lumen 216 that is preferably sized to house an inner member 225. Inner member 225 in the variation shown is generally tubular and is substantially free to rotate within lumen 216, preferably by providing rotational force to inner member 225 proximally outside of the patient's body. According to the example shown, this rotational force is applied to inner member 225 via a thumbwheel 205 that is provided on proximal hub assembly 201 coupled to proximal end portion 211 of delivery assembly 210. Thumbwheel 205 is rotationally coupled to inner member 225 within hub assembly 201, which rotational coupling may be achieved according to a number of adaptations as would be apparent to one of ordinary skill.

Rotation of inner member 225 is transmitted into rotation of a rotational coupler 280 that is engaged within a proximal end portion 252 of prosthesis 250 as follows. Inner member 225 has an aperture 228 on its distal end portion that provides a female counterpart of a mated key interface between the inner member 225 and a male counterpart, desirably provided by a shaped proximal end 281 of a rotational coupler 280 that is also rotationally engaged within a proximal end portion 252 of prosthesis 250. The keyed fitting between inner member 225 and rotational coupler 280 allows for transmission of rotational forces to rotational coupler 280. In order to maintain releasable axial engagement of this keyed coupling, a flexible member such as a filament 240 is looped through an aperture 283 through proximal end 281 of rotational coupler 280 with both filament ends 242 and 244 extending proximally through inner member 225 to a location in the proximal end of the catheter. The filament 240 is generally held in sufficient tension to keep the distal keyed fitting engaged, though it is further contemplated that the mere presence of the filament may provide an interference against uncoupling if there is a sufficiently tight tolerance in the male/female interface of the keyed fitting.

Rotational coupler 280 is rotationally engaged within proximal end portion 252 of prosthesis 250 through a proximal port, or aperture 251, such that the rotational coupler 280 is adapted to rotate within and relative to the prosthesis 250. This relative rotation is converted to force a deflection of prosthesis 250 into the desired shape of the second configuration in situ as follows.

According to one aspect of the rotational coupling, the prosthesis 250 is preferably held to resist rotation while rotational coupler 280 is rotated within the prosthesis 250. This may be achieved simply by frictional forces of surrounding tissue after the prosthesis 250 has been delivered into the desired vessel such as the coronary sinus. According to another example, this may be achieved by providing a releasable interface such as a friction fit between outer member 215 and proximal end portion 252 of prosthesis 250 wherein the frictional engagement of outer member 215 and prosthesis 250 are held in a relatively fixed position while inner member 225 and rotational coupler 280 are rotated. This embodiment is shown in FIG. 4. In addition, or in the alternative to the friction fit interface, a keyed interface may be employed as shown in FIGS. 6–7. According to this mode, a shaped proximal fitting 253 on the proximal end 252 of prosthesis 250 is adapted to mate as a male counterpart into a shaped aperture or fitting on the distal end 212 of outer member 215. This keyed interface allows for rotational coupling between the members in a similar manner as just described for the inner member 225 and rotational coupler 280, and may allow for a more releasable coupling with reduced friction upon axial detachment of the members.

Figure 8A:
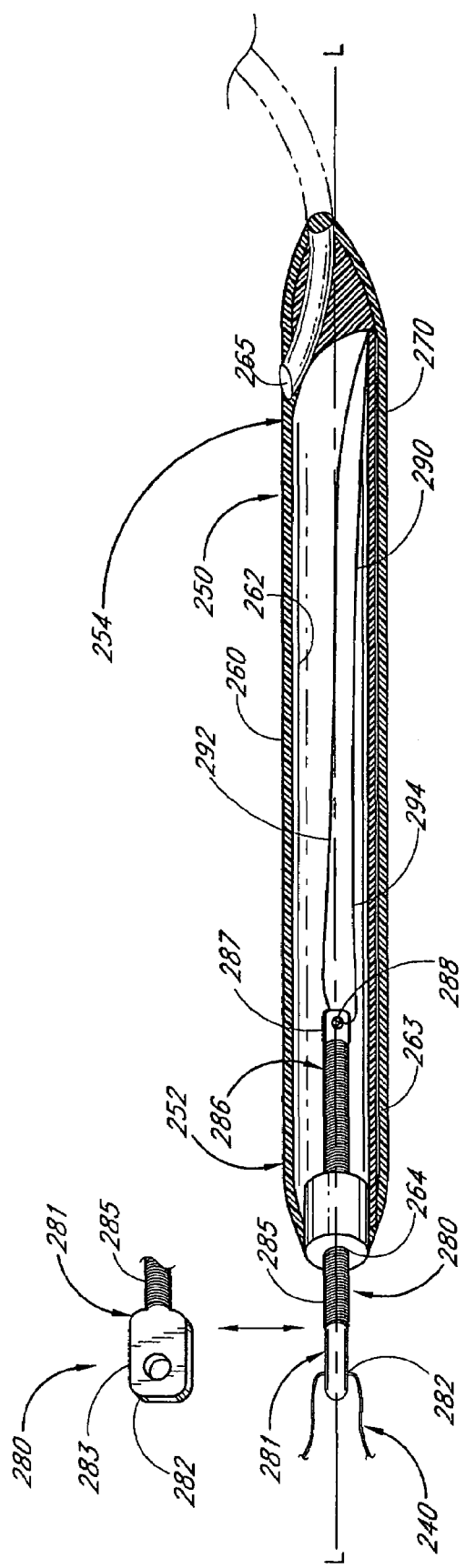
FIG. 8A shows a partially cross-sectioned side view of an implant, in a first configuration during a first mode of use.
Figure 8B:
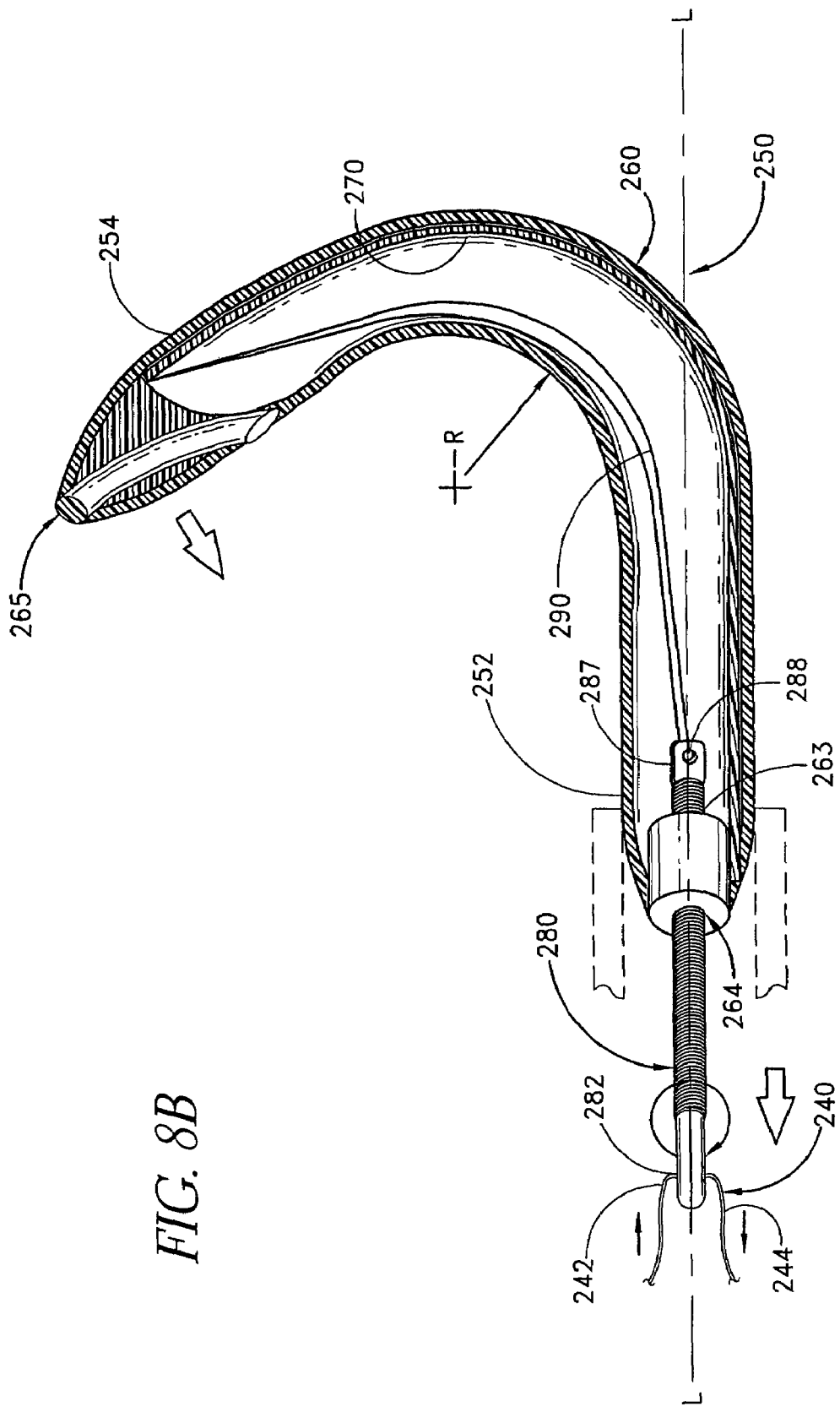
FIG. 8B shows a similar view as that shown in FIG. 8A, with the implant in a second configuration during a second mode of use.

The rotational forces from rotational coupler 280 may be converted to deflection forces on the prosthesis 250 according to one example as illustrated in FIGS. 8A–B. Prosthesis 250 includes a generally tubular wall or body 260 that has an inner lumen 262 and extends from the proximal end portion 252 to the distal end portion 254 of prosthesis 250. Secured along proximal end portion 252 is a nut fitting 263 that has a grooved inner bore 264 which communicates with inner lumen 262. Further to this specific embodiment, rotational coupler 280 is a screw member with outer helical threads 285 engaged within the mating threads of an inner surface (not shown) of a bore lumen such that a distal portion of screw threads 285 extends distally within lumen 262 and terminates at a second key fitting 287 similar to the shaped proximal end portion 282 and also having an aperture 288. Similar to the proximal end of rotational coupler 280, another flexible member or filament 290 is looped through aperture 288 such that two arms 292, 294 extend distally therefrom to an attachment point along distal end portion 254 of prosthesis 250. Because nut fitting 263 is fixed in relation to outer tubular body 260, and because that tubular body is held in a relatively fixed position as provided above, rotation of rotational coupler 280 moves coupler 280 proximally relative to body 260. This proximal axial translation of rotational coupler 280 puts tension on filament 290, which puts tension on the body 260 due to the distal attachment. This tension on outer body 260 forces a deflection of the body 260. Therefore, rotational force is converted into a tensile force which, in turn, causes radial deflection of the body 260 relative to the longitudinal axis L of the device 250. In other words, the body 260 is deflected about an axis that is transverse to the longitudinal axis L. See FIG. 8B.

The forced deflection described immediately above may be controlled in a particular plane by providing a composite structure within prosthesis 250 that is engineered to respond, e.g., yield, to these forces in a prescribed way. In the specific embodiment shown, a relatively noncompressible column support or spine member 270 is provided within lumen 262 of outer tubular body 260. This spine member 270 is more rigid and more resistant to axial forces, especially tensile forces, than the material of outer tubular body 260 alone. Therefore, providing spine member 270 along only one radial position along the circumference of the prosthesis 250 creates a bias on the device 250 to deflect away from the spine 270 toward a more compressive region of the device 250. Such composite design may further include a laminate structure, a composite structure—such as an imbedded wire reinforced wall structure, or may be achieved by engineering material variations in the device, such as for example by thinning, thickening, hardening, or softening the material at one location along the outer tubular body 260 relative to another region to urge the body 260 to deflect at a desired location.

As may be achieved by other controllable embodiments elsewhere herein described, deflection according to the present embodiment may be adjusted according to a healthcare provider's desires, and is adjustable in either direction—by either tightening the radius of curvature R or opening it. See FIG. 8B. According to this specific embodiment however, the adjustability of and choice between tightening and loosening of the deflection depends upon the direction and extent of rotation placed upon the rotational force transmission system.

Once the desired deflection is achieved and desired therapeutic results are observed, the prosthesis 250 may be detached from the delivery assembly 210 by severing the torque or rotational force transmission system at the keyed fitting between the inner member 225 and the rotational coupler 280. This is accomplished by first releasing at least one arm 242, 244 of the proximal filament 240 while withdrawing the other arm, thereby threading the filament 240 through aperture 283 (as shown in bold arrows in FIG. 8B) until it is unthreaded completely from the aperture 283. This allows inner member 225 to be withdrawn proximally from rotational coupler 280 to detach and thereby implant the prosthesis 250.

Alternatively, as with other adjustable deflection systems herein described, the prosthesis may be held in its therapeutic condition for a temporary period of time (which may nevertheless be prolonged during a hospital stay), during which time mitral valve regurgitation may be minimized, such as for example for the purpose of bridging the patient in a temporarily improved condition until other treatments may be performed, e.g. annuloplasty, valve surgery, heart transplant, etc. In this alternative temporary setting, at the appropriate time the deflected, contracted prosthesis may be adjusted back open from its cinched position around the valve, and then withdrawn without implantation by withdrawing the entire system, delivery assembly still engaged to the prosthesis. Moreover, it is further contemplated that such a temporary prosthesis may be modified to remove the detachment mechanisms herein described, which may provide for a simpler and lower cost device.

Device assembly 200 is also shown in FIGS. 3 and 8A–B to include a distal guidewire tracking member with a guidewire lumen 265 which is adapted to slideably engage a guidewire 230 in order to be placed in a percutaneous transluminal procedure into the desired vessel location, such as within the coronary sinus 22. The particular guidewire lumen shown is integral within the distal aspects of prosthesis 250 as a "rapid exchange" or "monorail" design that allows for relatively independent movement of the guidewire and catheter in vivo. Moreover, this design removes the need for the guidewire to ride coaxial through the entire device assembly 200, as would be the case for example in an "over the wire" type system. The type shown beneficially allows for detachable engagement of prosthesis 250, which is preferably achieved after withdrawing the optional guidewire 230 from the distal lumen 265.

In each of the foregoing implantation methods, the physician preferably monitors the degree of regurgitation during the step of tightening the implant. Although any reduction in mitral regurgitation may be desirable, regurgitation is preferably reduced to something less than moderate (less than 2+). In any event, at least a one grade reduction is preferably achieved. On the other hand, reconfiguration of the implant 250 is desirably not accomplished to an extent sufficient to produce mitral stenosis, or any flow limitation of hemodynamic significance.

Thus, the method of implantation preferably further comprises the steps of monitoring the degree of mitral regurgitation during, and preferably also before and following the implantation and/or reconfiguration steps. The degree of mitral regurgitation may be monitored such as by transesophageal echo cardiography, intracardiac echo cardiography, fluoroscopy using radiocontrast in the left ventricle (LVgram), or left atrial or pulmonary capillary wedge pressure tracings, as are understood in the art, during the incremental restriction of the mitral annulus and/or left ventricle step. Once a sufficient reduction in regurgitation has been achieved for a particular patient in the physician's judgement, the device 250 may be locked and the delivery assembly 210 detached from the device 250 and removed from the patient.

The method may additionally comprise the step of measuring the coronary sinus 22 and/or other coronary vein, and selecting an appropriately sized implant 250 from an array of implants of varying sizes. Such parameters may include diameter, length, or radius of curvature of the arc of the sinus. The appropriately sized implant 250 is thereafter positioned within the target vein. The implant 250 is thus preferably provided in a graduated array of sizes, so that the optimal size can be selected for each patient. The size of the coronary sinus 22 or other vein can be measured using any of a variety of techniques, such as echo cardiogram, MRI, CT Scan, or angiography as is understood in the art. Moreover, as is apparent to one of ordinary skill, measuring a parameter of the coronary sinus 22 generally provides indicia of certain parameters of the mitral valve and its annulus, such as for example mitral valve diameter, in which case either the coronary sinus parameter or the mitral valve parameter may provide the requisite information for choosing an appropriately dimensioned device 250 from the kit.

It follows that such mitral valve parameters may further be measured directly, such as by various of the methods just described, in order to generate the values used for choosing the appropriate device 250. Once a parameter for an anatomical feature is measured as herein described, its value is generally estimated according to the accuracy of the respective measuring tool—it is contemplated that persons without specialized medical skills or training can choose the appropriate medical device 250 from the kit once armed with this estimated value. For example, packaging for each device 250 of the kit may indicate the respective dimensions that are unique to that device 250 with respect to other devices of the kit, and the estimated value of the measured anatomical parameter may simply be compared.

It is contemplated and apparent that various of the embodiments herein described are adapted to accomplish manipulation of the coronary sinus 22 for mitral annulus reduction without substantially altering the length of the device 250 within the sinus 22. This may provide a benefit by increasing the useful purchase of the device 250 along the coronary sinus 22 and circumferentially around the mitral annulus as the sinus length and/or annulus diameter may be reduced during remodeling from the radial deflection of the prosthetic device 250. This may also mean that the dimension of the device 250 in a kit of devices may not directly correspond to the estimated value of the anatomical parameter that is measured. For example, the compared value of the measured device parameter may be shorter than an estimated coronary sinus 22 length due to a possible shortening of the sinus 22 during device 250 treatment. Or, the anatomical parameter may be estimated from an initial value based upon an anticipated or desired final result from treatment and such procedurally related value be used for choosing the appropriate device (e.g. comparing an estimated final length of the sinus or mitral valve diameter with a known dimension of the device in the remodeling configuration when used in situ).

As a further aspect to the present invention, the implant 250 is preferably combined with an appropriate drug therapy for treating congestive heart failure. Residual regurgitation and other hemodynamic functions are preferably measured following implantation of the implant of the present invention. Heart medications are preferably adjusted to take into account the reduction in regurgitation and/or reduction in left ventricle volume in formulating an ongoing drug therapy for the patient.

Still further, the present invention contemplates temporary use in the sinus 22 for mitral valve remodeling as a bridging regime in combination with other permanent treatments such as more conventional annuloplasty or valve replacement via surgery. Such combined systems of devices 250 and respective methods of use, which may further be combined with the pharmaceutical drug regimes, provide an overall treatment regime that can provide a highly beneficial result for management of patients with harmful mitral valve regurgitation.

Any of the embodiments discussed herein may additionally be provided with one or more externally facing electrically conductive axially extending strips or annular bands, to enable the device 40 to function additionally as a cardiac pacing or other diagnostic or therapeutic cardiac electrode. The electrically conductive band or bands are placed in electrical communication with a pacing source or diagnostic instrument by way of one or more electrical conductors extending away from the device 40. The conductors may be electrically connected to any of a wide variety of electronic cardiac rhythm management devices, which are well known in the art.

As shown in one embodiment in FIGS. 9A and 9B, once in the coronary sinus the elongate body 320 is adapted to be adjusted from the first implantation (flexible) configuration to a second (relatively rigid) remodeling configuration that has a shape that is adapted to remodel the mitral valve annulus. According to the embodiment shown in FIG. 9B, this shape is generally adapted to provide an external force onto the annulus in order to reduce its diameter along at least one transverse axis, such as according to the arcuate shape shown that at least in part grips down onto a portion of the circumference of the valve to provide a diameter reducing force. As is also shown in phantom, the arcuate shape may take different forms in terms of degree, and in a further highly beneficial application is controllable and selectable between various or through a continuous range of degrees. Such controllability according to the embodiment shown is also selective between intermediate deflectable portions 360, 370, 380, as is shown in FIG. 9B and will be further developed below.

Elongate body 320 is constructed from tubular wall 325 that extends continuously along the length of the deflectable portions 360,370,380 of the elongate body 320. An array or plurality of distinct, discontinuous slots or voids 330 are formed within the wall 325, each void 330 having an elongated shape that is transverse to the longitudinal axis. Voids 330 permit axial shortening of one side of the tubular wall 325, enabling the curvature illustrated in FIG. 9B.

By further reference to the specific embodiment of FIGS. 9A–F, transverse voids 330 have a central groove-shaped region with two adjoining portions 332, 334 that converge at an apex 333 along the longitudinal axis. Such a shaped void 330 is defined at least in part by two opposing complementary shaped surfaces of two adjacent, longitudinally opposing portions 340, 350 of the wall of the elongate body 320. One of these portions 340 desirably assumes a convex shape in an axial, distal direction, and the other portion 350 is desirably concave in an axial, proximal direction around the apex 333. These shaped surfaces 340, 350 are preferably in a nested configuration with the convex portion 340 positioned within the concave portion 350. In this arrangement, lateral (rotational) movement of one of the adjacent wall portions 340, 350 relative to the other portion 340, 350 is substantially prevented by a mechanical interference with the other adjacent portion 340, 350. The relative nesting of adjacent portions 340, 350 of the elongate body 320 provides a mechanical interference to radial deflection along a first plane and substantially isolates deflection of the elongate body 320 along a second plane upon application of axial bending forces.

FIG. 9D shows grooved voids 330 in plan view for the purpose of simplifying the illustration for better understanding. However, as depicted in FIG. 9C and by reference to FIG. 9E, these transverse voids 330 (and the generally the entire V-shaped portion herein described in detail) span across at least about 180 degrees of the circumference of the elongate body 320. Preferably, the transverse voids 330 span across more than about 300 degrees of the circumference of the elongate body 320, and still more preferably the voids span across between about 300 degrees and about 315 degrees of the circumference. By arranging such grooved voids in a similar alignment around the circumference of the wall 325, an integral and continuous backbone or spine 327 is formed along wall 325 that runs axially along the length of the elongate body 320. This overall arrangement of voids 330 and spine 327 has been observed to provide a desirable combination of bendability, due to the voided pattern, and axial integrity, due to the remaining wall structure.

The elongate body 320 of the implant 300 shown in FIGS. 9A–F generally has three deflectable portions 360, 370, 380, and one non-deflectable portion 310 along the longitudinal axis. Each deflectable portion 360, 370, 380 has a group of voids 330 as just described in order to be individually deflectable between the first and second configurations with an applied force from outside of the patient's body while the elongate body 320 is positioned within the coronary sinus. More specifically, three forming elements 365, 375, 385 may be coupled to the three deflectable portions 360, 370, 380, respectively, in order to apply a deflection force to that portion to reshape that portion between the first and second configurations. Each forming element 365, 375, 385 is preferably adapted to extend externally from the patient's body when the elongate body 320 is positioned within the coronary sinus in order to be manually manipulated to apply the deflection force to the respectively coupled deflectable portion 360, 370, 380. Deflection of each of these portions combined provides for the overall shape for the elongate body 320 in the second configuration.

Forming elements 365, 375, 385 are attached to elongate body 320 at unique, longitudinally spaced points of attachment 361, 371, 381, respectively, that are each at or distal to the distal end of each respectively coupled deflectable portion 360, 370, 380. One beneficial application is shown for the attachment of the forming members 365, 375, 385 to the body 320, wherein each point of attachment 361, 371, 381 has two axially spaced apertures, which are shown as proximal and distal apertures 362, 363 for point of attachment 361, proximal and distal apertures 372, 373 for attachment point 371, and proximal and distal apertures 382, 383 for point of attachment 381. As illustrated for point of attachment 371 in FIG. 9F, a shaped distal end 377 for forming element 375 is sized to be seated within distal aperture 373 where it is secured by a securing agent 374 which may be an adhesive, melt bond, or solder, for example. Any or all of the respective forming elements 365, 375, 385 may also be welded through the apertures to the wall. Forming element 375 extends proximally from distal aperture 373 and is further secured to wall 325 by additional securing agent 374 introduced through proximal aperture 372. The securing agent 374 may be applied in one operation from outside in through both apertures 372, 373. In addition, distal end 377 may also be shaped to provide a mechanical securement means for attachment during proximal axial forces, such as is shown in phantom in FIG. 9F.

According to one specific embodiment that has been observed to be useful, the apertures for this attachment embodiment are generally between about 0.020 inches and about 0.022 inches in diameter with similar longitudinal spacing, and the distal end for the seated forming elements are between about 0.012 and about 0.014 inches in diameter. Further to that embodiment, wall 325 is generally constructed from a tubular, stainless steel wall or hypotube with a plurality of grooved voids 330 formed therein according to a pattern similar to that shown and described by reference to FIG. 9D or elsewhere herein. The respective forming elements are soldered to the respective attachment points using gold/tin solder. Further to this embodiment, grooves such as shown and described by reference to FIG. 9D were formed in the underlying stainless tube by laser cutting, though other well known techniques such as hand grinding, mechanical cutting, photo-lithography, etc. may alternatively be used.

As previously described herein, the applied force from the forming elements 365, 375, 385 are generally an axial force between the attachment points 361, 371, 381 to the elongate body 320 and a proximal location (not shown) along the elongate body 320 that is proximal to that deflectable portion. According to the specific embodiments shown this force is generally between the attachment points 361, 371, 381 and the proximal end portion of the elongate body 320. The elongate body 320 may generally be held during forced deflection by means of a holding device (not shown) in order to substantially fix the proximal end portion of the elongate body 320 relative to the deflectable portion so that the axial force may be applied between those portions in situ. While the proximal manipulation of the forming elements 320 in order to apply the deflection force to the deflectable portions 360, 370, 380 may be axial as just described, it may in another regard be rotational.

Each deflectable portion 360, 370, 380 is substantially axially rigid and non-compressible relative to the longitudinal axis L, and therefore the overall axial length of elongate body 320 remains substantially constant between the first and second configurations. However, each deflectable portion is relatively flexible along a radial axis transverse to the longitudinal axis such that the deflectable portion is adapted to bend radially upon application of an axial force between a distal location on the elongate body at or distal to a distal end of the deflectable portion and a proximal location along the elongate body 320 proximal to that deflectable portion. In one regard, the elongate body 320 may be generally axially non-compressible or non-expandable between each deflectable portion 360, 370, 380 and the proximal end portion of the elongate body 320, such that each deflectable portion 360, 370, 380 is adapted to bend radially upon application of a compressive or tensile axial force, respectively, on the elongate body 320 between the distal location and a proximal location that is at the proximal end portion of the elongate body 320.

In still a further regard, other constructions for elongate body 320 may also provide for the combination of an integral and continuous wall 325 from the proximal end portion to the distal end portion of the body and a controlled radial bending response to axially compressive or tensile forces. In addition or in the alternative to the continuous integral wall incorporating the formed voids 330, the wall 325 may also include an engineered composite support structure with engineered support elements that are arranged to control the spatial strain response to the stress of the applied forces. Other suitable shapes for voids 330 may also be acceptable.

One particular variation of the patterned voids according to the nested V-pattern (or U-pattern) embodiment shown in FIGS. 9A–F is shown in FIG. 9G, wherein the nested adjoining portions 340, 350 include interfacing surfaces 342, 352 that have interlocking teeth 344, 354 which are adapted to be locked in a radially deflected pattern in the second configuration. More specifically, the interfacing pattern of teeth 344, 354 are adapted to perform like a ratchet mechanism. By positioning this region along an inner radius of curvature during the bending of forced deflection, compressive forces bring the convexly shaped tooth region 340 deeper into the fitted well formed by the concave receiving region 350. This motion provides an interference between teeth 344, 354 that deflects portion 340 until further motion toward portion 350 clears tooth 354 and recovery locks tooth 344 behind 354. This interactive motion of adjacent portions in voided regions is further represented by bold arrows in FIG. 9G.

Figure 10:
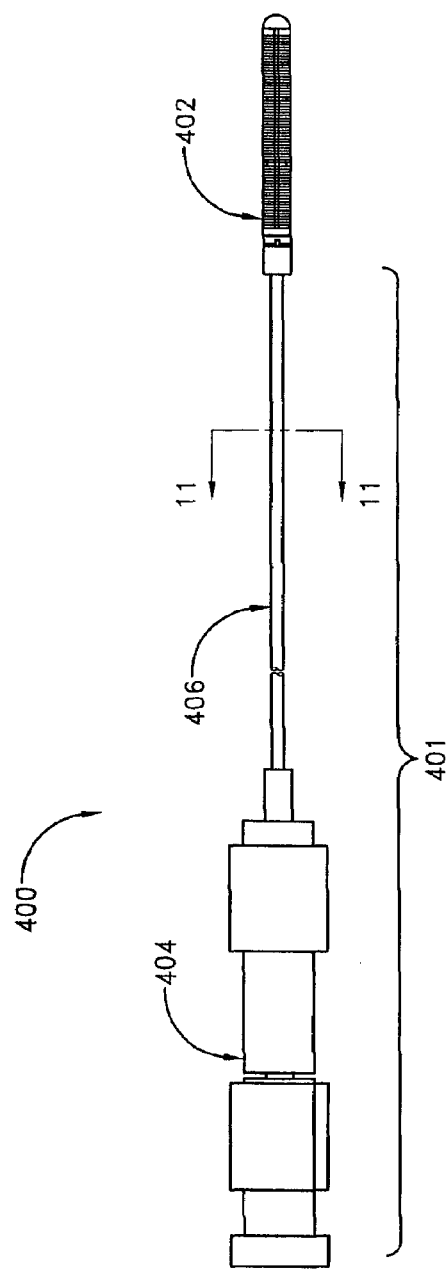
FIG. 10 is a bottom plan view of an alternative medical device including a delivery assembly, comprising a handle assembly and a shaft, and an implant configured for remodeling a mitral valve.

FIG. 10 illustrates an additional construction of a medical device 400 adapted to position an implant 402, or prosthesis, into the coronary sinus or other treatment site. Similar to the embodiments described above, medial device 400 includes a handle assembly 404 at a proximal end, while the implant 402 is located at a distal end. The handle assembly 404 and implant 402 are connected by an elongate, flexible catheter body 406. Desirably, the body 406 is or includes an extrusion of a material having sufficient column strength, that is, it resists compression in an axial direction, while permitting the body 406 to bend in a radial direction. Any of a variety of polymers well known in the transluminal catheter arts, such as HDPE or PEBAX, is used to form the body 406. However, other suitable materials may also be used. In one embodiment, the body 406 has an outside diameter of approximately 0.094 inches.

Figure 11:
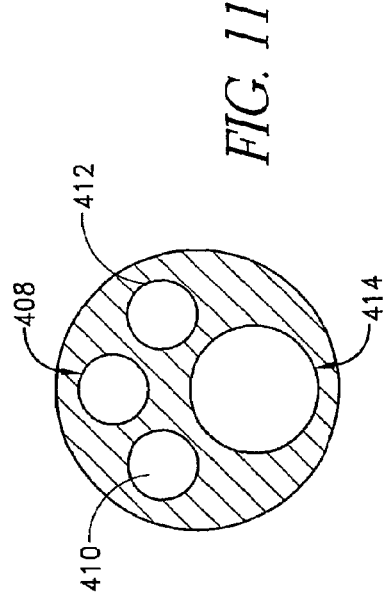
FIG. 11 is a cross section of the shaft of the medical device of FIG. 10 taken along the view line 11—11 of FIG. 10.

With reference to FIG. 11, a plurality of lumens or passages extend in an axial direction along the length of the catheter body 406. The illustrated extrusion includes three small lumen 408, 410, 412 and one larger lumen 414. The small lumen 408, 410, 412 may be disposed substantially within one half of the circular cross section of the body 406 and each has an inside diameter of approximately 0.024 inches. The larger lumen 414 is desirably positioned substantially within a half of the circular cross section of the body 406 opposite the small lumen 408, 410, 412 and may have a diameter of approximately 0.044 inches. Collectively, the lumen 408, 410 and 412 allow control components 400 (e.g., forming elements 365, 375, 385 of FIGS. 9A and 9B) of the medical device 400 to extend from the handle assembly 404 to the implant 402 while being protected within the shaft 406. Alternatively, only a single pull wire lumen or two pull wire lumen may be provided as needed, depending upon the desired number of pull wires. As will be described in detail below, the control components 404 convert operational movements of the handle assembly 404 into desired resultant movement of the implant 402. The larger lumen 414 may be used to rotatably receive a driver 436 as will be discussed. Additionally, one or more of the lumen may be used to permit irrigation to the coronary sinus, infusion of drugs or contrast media, or other desired purposes.

With reference to FIGS. 12 and 13, the implant 402 is shown in greater detail. FIG. 13 is an enlarged view of a portion of FIG. 12 illustrating the releasable connection between the delivery assembly 401 and the implant 402. As described above, the implant 402 is removably connected to the delivery assembly 401 such that the delivery assembly 401 and implant 402 may be disconnected once the implant 402 has been properly positioned and tensioned within the coronary sinus or other body lumen or hollow organ.

The implant 402 defines a body portion 416, which is preferably tubular in shape with at least one central lumen extending therethrough. The overall length of the implant 402 can be varied, depending upon the intended treatment site and desired clinical performance. In one application, in which the device is intended to be positioned within the coronary sinus to reduce the diameter of the mitral valve annulus across a predetermined plane, the implant 402 is generally within the range of from about 5 cm to about 15 cm in length. For most adult patients, axial lengths within the range of from about 6 cm to about 12 cm may be used. In one embodiment, the implant 402 is approximately 9 centimeters long, and may have a cross-sectional area of no more than approximately 15 mm$^2$. Preferably, the implant 402 has a cross-sectional area of no more than about 10 mm$^2$.

The implant may be constructed from a similar material as those embodiments described above, such as a variety of stainless steels, Nitinol or other known materials suitable for implantation. An atraumatic distal tip 418 is provided on the distal end of the body portion 416. A leading end of the tip 418 may be rounded such that the atraumatic tip 418 will not cause significant tissue damage as it is advanced through the vasculature of the patient.

A nut 422 or other structure having a threaded aperture therein is provided at the proximal end of the body portion 416. Desirably, the nut 422 is axially and rotationally fixed relative to the body portion 416. For example, in the illustrated embodiment the outer edge of the nut 422 is circular with flat 464 on one side to provide keyway 481 for pullwire 458 and is sized to fit within the body portion 416. Nut 422 is thermally welded to body portion 416 and is provided with keyway 481. Of course, other suitable arrangements for preventing relative rotation between the nut 422 and body 416 may be used, such as other mechanical interference arrangements, fasteners, solder or adhesives, for example.

The implant 402 additionally includes a screw 428 having a shaft portion 430 and a head portion 432. The shaft portion 430 includes external threads which mate with internal threads on the nut 422. Thus, rotation of the screw 428 relative to the body portion 416 results in the screw 428 translating axially with respect the body portion 416. This relative movement may be utilized to move the body portion 416 of the implant 402 from an implantation configuration to a remodeling configuration through any suitable construction, such as through the use of a pull wire or other forming element as is described above, for example.

The head portion 432 of the screw 428 includes a rotational coupling such as a cavity 434 extending axially from a proximal end of head portion 432. Desirably, the cavity 434 is shaped to receive a control component of the medical device 400 such as driver 436. In the illustrated embodiment, the cavity 434 is hex shaped and sized to receive a hex-shaped distal end portion 438 of the driver 436 (FIG. 14).

A male connector 440 contains the head portion 432 of the screw 428. The male connector 440 includes a shaft portion 442 and a head portion 444. The head portion 444 of the male connector 440 has a larger diameter than the shaft portion 442. A passage 446 desirably extends axially through the male connector 440 and defines a first portion 448 and a second portion 450. The first portion 448 of the passage 446 is located proximate the head portion 444 of the male connector 440 and has a larger diameter than that of the second portion 450, which is located proximate the shaft portion 442 of the male connector 440. A transition between the first portion 448 and the second portion 450 defines a shoulder surface 452 which extends generally transverse to the longitudinal axis of the male connector 440. The first portion 448 of the passage 446 is preferably sized and shaped to receive the head portion 432 of the screw 428. Desirably, the head portion 432 of the screw 428 abuts the shoulder 452 of the passage 446.

An annular collar 454 secures the head portion 432 of the screw 428 within the passage 446. Desirably, the outer diameter of the collar 454 is approximately the same as the outer diameter of the head portion 444 of the male connector 440. The collar 454 includes an inner flange portion 456 which is sized and shaped to fit within the first portion 448 of the passage 446 of the male connector 440 in a press fit configuration.

In a similar manner to the embodiments described above, the implant 402 desirably includes a wire 458 which is operational for moving the implant 402 from a first, delivery configuration to a second, remodeling configuration. The wire 458 is desirably anchored to a distal end of the implant 402 by thermal welding or any of the methods described above, or any other suitable method as may be determined by one of skill in the art. Desirably, the proximal end of the wire 458 is anchored to the male connector 440 and collar 454 and, preferably, is thermally welded or otherwise bonded to the male connector 440 and collar 454. However, other suitable methods of attachment may also be used, such as an adhesive or mechanical fastener, for instance. Preferably, the male connector 440, and collar 454 have slots 460 and 462 to fit the proximal end of pull wire 458 to allow the wire 458 to lay flat and not increase the outside diameter of collar 454 or connector 440. Nut 422 includes flat 464 on one side which is sized and shaped to permit clearance for the wire to pass therethrough.

As described above, the delivery assembly 401 is preferably capable of being releasably coupled to the implant 402. For this purpose, a female connector 466 is desirably coupled, such as by thermal welding, to the connector wire 487 at the distal end of the shaft 406. The female connector 466 is preferably hollow and substantially cylindrical in shape. The distal end of the female connector 466 includes a plurality of prongs, or finger portions 468, which are able to flex radially outward to permit the female connector 466 to engage the shaft portion 442 of the male connector 440. Desirably, the resiliency of the material from which the female connector 466 is constructed enables the female connector 466 to firmly grip the male connector 440. Desirably, an inner surface of the finger portions 468 defines an annular projection 470 which corresponds with an annular groove 472 of the male connector 440. When the female connector 466 is engaged with the male connector 440, the annular projection 470 desirably rests in the annular groove 472 to assist and inhibiting undesired relative axial movement between the delivery assembly 401 and the implant 402.

The delivery assembly 401 additionally includes a cover 474 that is coupled at the distal end of the shaft 406. The cover 474 is axially movable from a first position in which the finger portions 468 of the female connector 466 are uncovered to a second position where the cover 474 overlaps at least a substantial portion of the finger portions 468. In its second position, the cover 474 inhibits undesired flexing of the finger portions 468 to assist in maintaining a connection between the female connector 466 and the male connector 440.

To prevent rotational movement between the delivery system (including shaft 406 and female connector 466) and implant body portion 416, one of finger portions 468 is removed or omitted from female connector 466 to create space or keyway 483 that fits into key 485 that is thermally welded to shaft portion 442 of male connector 440.

FIG. 14 is an enlarged view of the driver 436 apart from the medical device 400. The driver 436 is desirably an elongate shaft and extends from a proximal end 480 to a distal end 482. The driver 436 may be constructed from a NiTi material, however, other suitable materials may also be used. The proximal end 480 of the driver 436 is desirably coupled for rotation with respect to the handle assembly 404, which will be described in greater detail below. The distal end 482 is preferably non circular such as hex-shaped in cross-section and is sized to engage the corresponding hex-shaped cavity 434 of the screw 428. Thus, rotation of the driver 436 results in corresponding rotation of the screw 428. Other suitable arrangements to permit rotational coupling of the driver 436 and screw 428 may also be used, such as using complementary polygonal or other non round-cross-sectional shapes for the mating components.

The driver 436 may include a shoulder 484 disposed on a proximal side of the hex-shaped distal end 482. Preferably, the diameter of the shoulder 484 is larger than a width W (FIG. 15) of the hex-shaped distal end 482. In one preferred embodiment, the diameter of the shoulder 484 is approximately 0.032–0.040 inches and the width W is approximately 0.027 inches. Thus, the shoulder 484 effectively functions as a stop when the hex-shaped distal end 482 of the driver is inserted into the cavity 434 of the screw 428. As illustrated, the shoulder 484 and the cavity 434 desirably include complementary chamfers 486, 488, respectively, to permit easier entry of the hex-shaped distal end 482 into the cavity 434.

The illustrated driver 436 may include one or more reduced-diameter portions 490 on a proximal side of the shoulder 484. The diameter of portion 490 may be smaller than both the width of the shoulder 484 and a diameter of a main portion 492 of the driver 436, which desirably extends from the proximal end of distal portion 490 to the proximal end 480. Preferably, the main portion 492 of the driver 436 has a diameter of approximately 0.04 inches. The reduced-diameter portion 490 may have a length of approximately 0.5 inches or more and a diameter of approximately 0.027 inches. However, other suitable dimensions may also be employed. Desirably, each of the transition between the reduced-diameter portion 490 and the main portion 492 of the driver 436 and the transition between the reduced-diameter portion 490 and the shoulder 484 define a chamfer 494, 495, respectively to advantageously reduce stress concentrations.

Figure 16:
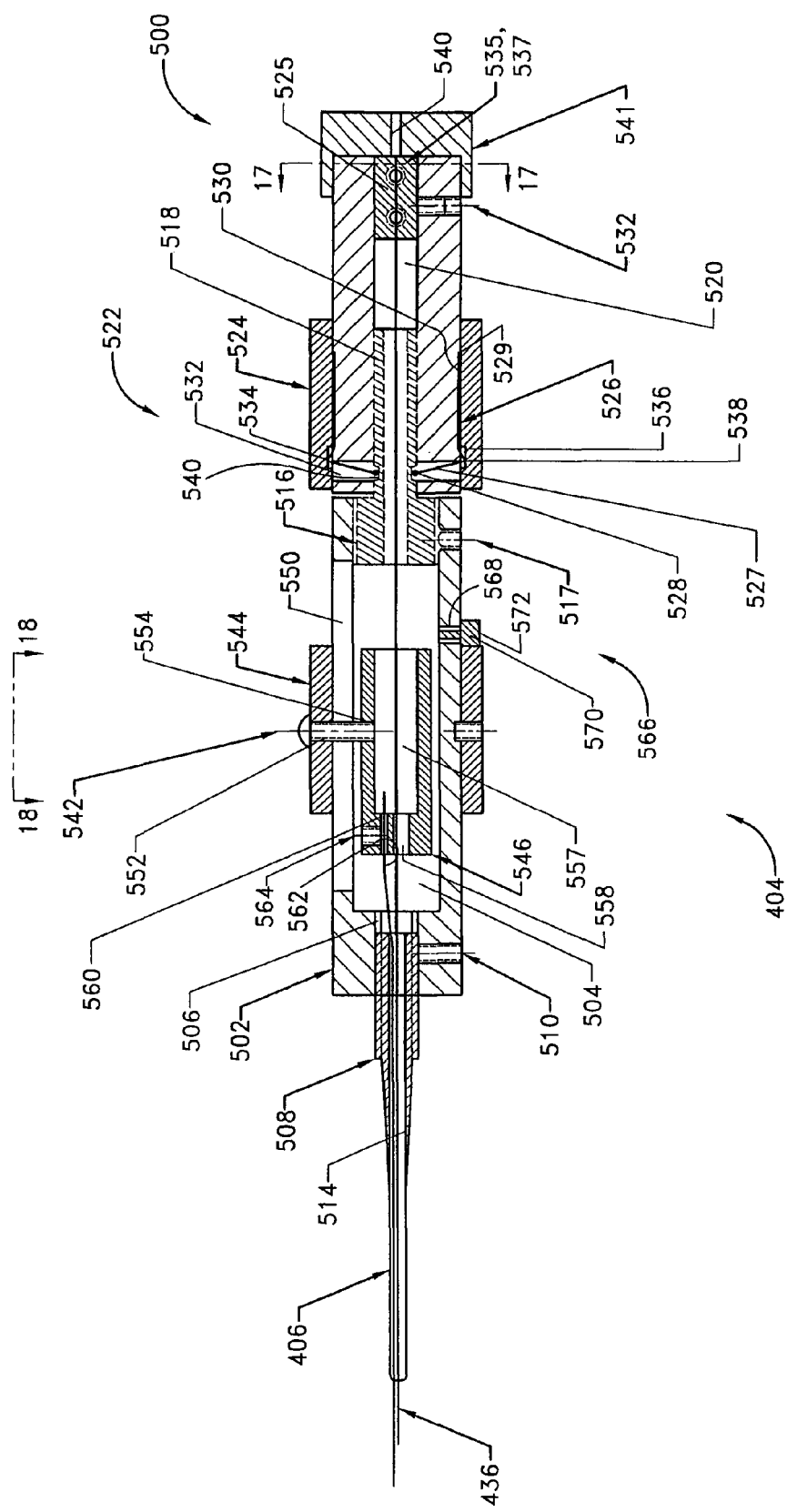
FIG. 16 is a cross section view of a handle assembly of the medical device of FIG. 10.

FIG. 16 is an enlarged cross-section of the handle assembly 404, which is primarily comprised of a proximal handle 500 and a distal handle 502. The distal handle 502 is configured to be held stationary during use of the medical device 400 and the proximal handle 500 is configured to be rotatable with respect to the distal handle 502, thus rotating the driver 436 to selectively move the implant 402 between a delivery position and a remodeling position.

The distal handle 502 is generally cylindrical in shape and defines an internal cavity 504. A threaded aperture 506 extends from the cavity 504 through the distal end of the distal handle 502 and is substantially concentric with a longitudinal axis of the handle assembly 404. A proximal connector 508 is desirably retained by a threaded connection with the threaded aperture 506 and extends axially from a distal end of the distal handle 502. Desirably, the distal handle 502 additionally includes a threaded aperture 510 situated substantially transverse to the longitudinal axis and intersecting the threaded aperture 506. A set screw is advantageously in threaded connection with the threaded aperture 506 and may be tightened against the proximal connector 508 to inhibit undesired axial movement of the proximal connector 508 with respect to the distal handle 502.

The proximal connector 508 includes a central aperture 514 passing axially therethrough. The central aperture 514 is desirably substantially concentric with the longitudinal axis of the handle assembly 404 and receives the catheter shaft 406 in a fixed axial position with respect to the distal handle 502. The shaft 406 may be fixed to the proximal connector 508 in any suitable manner, such as by adhesives or thermal welding, for example.

In the illustrated embodiment, the cavity 504 opens through the proximal end of the distal handle 502 to receive a handle connector 516, preferably through a threaded connection therebetween. In addition, a set screw arrangement 517, similar to that described above in relation to the proximal connector 508, is desirably provided to inhibit undesired movement of the handle connector 516. The handle connector 516 is configured to connect the proximal handle 500 and the distal handle 502, while allowing relative rotation therebetween. The handle connector 516 desirably includes a shaft portion 518 extending proximally away from the distal handle 502. A cylindrical passage 520 extends axially through the proximal handle 500 and is sized to be rotatably mounted on the shaft portion 518 of the handle connector 516.

Preferably, the proximal handle 500 includes a handle release assembly 522 that permits releasable engagement to the distal handle 502. The release assembly desirably comprises an annular release collar 524 surrounding the proximal handle 500. The release collar 524 is sized to allow axial movement with respect to the proximal handle 500. A plurality of wire retainers 526 (two shown) releasably engage the shaft portion 518 of the handle connector 516 to selectively secure the proximal handle 500 in a fixed axial position with respect to the distal handle 502. Each of the wire retainers 526 include a short leg 527, which is circular in cross-section and terminates in a ball end 528, and a long leg 529, which is preferably rectangular in cross-section. Desirably, the short leg 527 and the long leg 529 define an angle of approximately 75° between them when the wire retainer 526 is in a relaxed position. Preferably, each wire retainer 526 is constructed from a variety of stainless steel and a total of two, or four, or more wire retainers 526 are employed.

In the illustrated embodiment, the long leg 529 of the retainer 526 is held between an outer surface of the proximal handle 500 and an inner surface of the release collar 524 and, preferably, within a groove 530 defined by the proximal handle 500. A plurality of apertures 532 extend radially through the proximal handle 500 near its proximal end. The outer surface of the proximal handle 500 defines a shoulder 534 between the grooves 530 and the apertures 532. The shoulder 534 mechanically deflects the wire retainer 526, when secured by the release collar 524, such that the angle between the short leg 527 and long leg 529 is increased from the relaxed position of the wire retainer 526. The inner surface of the release collar 524 defines an annular groove 536, which desirably straddles the shoulder 534, at least when the release collar 524 is in a relaxed position. The short leg 527 of the wire retainer 526 extends through the aperture 532. The groove 536 preferably engages a bend 538 defined by the transition between the short leg 527 and the long leg 529 of the wire retainer 526 to hold the ball end 528 within an annular groove 540 defined by the shaft portion 518 of the handle connector 516.

In FIG. 16, the release collar 524 is in a first, or engaged position such that the ball end 528 is held within the annular groove 540 to inhibit removal of the proximal handle 500 from the distal handle 502. The release collar 524 is movable toward the proximal end of the proximal handle 500 into a second, or release position to selectively permit the proximal handle 500 to be removed from the distal handle 502. When the release collar 524 is moved toward the release position, an edge of the groove 536 engages the wire retainer 526 to deflect the short leg 527 and move the ball end 528 out of the groove 540 of the handle connector 516, thereby releasing the proximal handle 500 from the distal handle 502.

Figure 17:
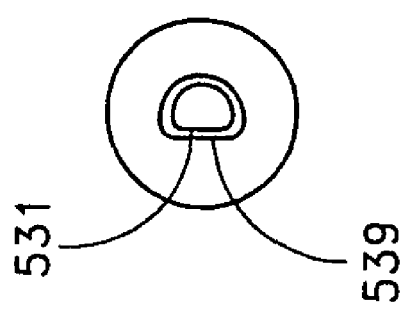
FIG. 17 is a cross sectional view taken along the view line 17—17 of FIG. 16.

A driver holder 525 is positioned within the proximal end of the passage 520 to fix the driver 436 for rotation with the proximal handle 500. Thus, the driver holder 525 is fixed for rotation with the proximal handle 500, preferably by having a flat 531 which is engaged by a flat portion 539 of the proximal end of the passage 520 (FIG. 17). A set screw arrangement, similar to those described above, may be used to secure the driver holder 525 axially with respect to the proximal handle 500. A pair of set screws 535, 537 secure the driver 436 axially and rotationally with respect to the proximal handle 500. Thus, rotation of the proximal handle 500 results in rotation of the driver 436. Desirably, an end cap 541 is press fit over the proximal end of the proximal handle 500 to further secure the driver holder 525. The end cap 541 may include an aperture 540 extending axially therethrough. Desirably, the aperture 540 is substantially aligned with the driver 436.

Figure 18:
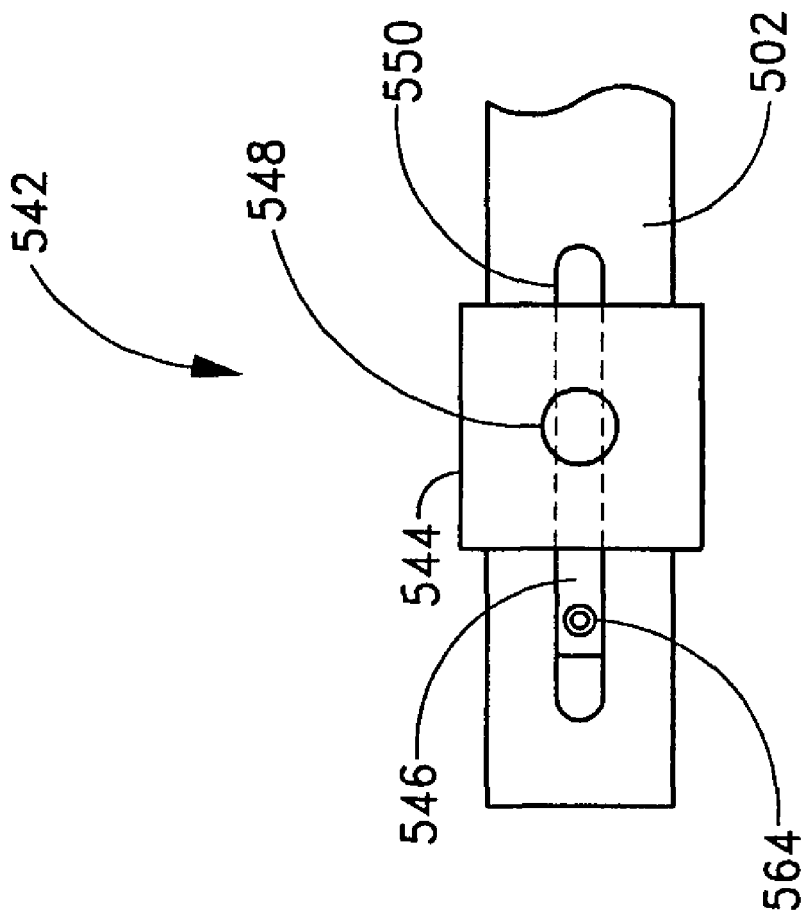
FIG. 18 is a plan view of a portion of the handle assembly of FIG. 16 taken along the line 18—18 of FIG. 16.

With reference to FIGS. 16 and 18, the distal handle 502 includes a detach arrangement 542 which allows the delivery assembly 401 to be detached from the implant 402 once it has been properly positioned and moved from its delivery position into its remodeling position. The detach arrangement 542 includes an annular detach collar 544 surrounding the distal handle 502. The detach collar 544 is desirably concentric with the distal handle 502 and capable of sliding axially thereon. A handle pin 546 is positioned concentrically within the cavity 504 of the distal handle 502. A fastener, such as a screw 548, passes through a slot 550 in the distal handle 502 to connect the handle pin 546 to the detach collar 544. Preferably, external threads of the fastener 548 mate with internal threads of apertures 552, 554 of the detach collar 544 and handle pin 546, respectively, to provide a secure connection therebetween.

The handle pin 546 is desirably substantially cylindrical in shape and defines an internal cavity 557 extending from an open proximal end to a closed distal end of the handle pin 546. The closed distal end of the handle pin 546 includes a pair of apertures 558, 560 extending axially therethrough, opening into the cavity 557. The aperture 558 is sized and positioned to permit the driver 436 to pass there through. The aperture 560 is sized to receive a proximal end of a detach wire 562. The detach wire 562 extends from the handle pin 546 to the cover 474 (FIG. 13) through one of the apertures 408, 410, 412 of the shaft 406. The detach wire 562 is secured to the cover 474 by any suitable method, such as thermal welding, adhesives, or mechanical fasteners, for example. A set screw arrangement 564, similar to those described above, is utilized to secure the detach wire 562 within the aperture 560 for axial movement with the handle pin 546. Thus, when the detach collar 544 is moved toward the proximal end of the handle assembly 404, the detach wire 562 pulls the cover 474 to uncover the finger portions 468 of the female connector 466. When the cover 474 is in this position, the female connector 466 is able to be disconnected from the male connector 440 and, thus, the delivery assembly 401 is able to be disconnected from the implant 402, as described above.

The handle assembly 404 also desirably includes a detach collar lock arrangement 566 to substantially prevent undesired movement of the detach collar 544. The lock arrangement 566 preferably includes a threaded aperture 568 passing radially through the distal handle 502. A lock screw 570 is provided for threaded engagement with the threaded aperture 568. The lock screw 570 includes a head portion 572, which interferes with movement of the detach collar 544 toward a proximal end of the handle assembly 404 when the lock screw 570 is screwed substantially fully into the aperture 568. The lock screw 570 may be backed partially, or fully, out of the aperture 568 to permit desired movement of the detach collar 544 toward the proximal end of the handle assembly 404.

Operation of the medical device 400 is substantially similar to the embodiments described above. Preferably, before the procedure is initiated, the lock screw 570 is positioned to prevent undesired movement of the detach collar 544, which could result in premature detachment of the delivery assembly 401 from the implant 402. Once the implant 402 has been desirably positioned within the coronary sinus by a suitable method, such as described above, the proximal handle 500 is rotated with respect to the distal handle 502 to cause rotation of the driver 436. Rotation of the driver 436 results in corresponding rotation of the screw 426 which, in turn, causes the implant 402 to move from a delivery configuration to a remodeling configuration, as described in detail above. The direction of rotation of the proximal handle 500 will vary depending on the orientation of the threaded connection between the screw 428 and the nut 422. However, if a right hand thread orientation is used, the proximal handle 500 will be rotated counter-clockwise to move the implant 402 from a delivery configuration to a remodeling configuration.

When the implant 402 has achieved a desired remodeling configuration, the lock screw 570 is backed off from its locked position to permit movement of the detach collar 544. The detach collar 544 may then be moved toward the proximal end of the handle assembly 404, thereby retracting the cover 474 and exposing the finger portions 468 of the female connector 466. The handle assembly 404 may then be pulled with a sufficient force to cause the finger portions 468 of the female connector 466 to deflect radially outwardly such that the female connector 466 may be disconnected from the male connector 440, thus disconnecting the delivery assembly 401 from the implant 402. The delivery assembly 401 is then removed from the patient, leaving the implant 402 in place.

Although a specific proximal hand piece has been disclosed in detail herein, any of a variety of alternative hand pieces can be readily designed and constructed, as will be apparent of those of skill in the art, to enable practicing the present invention. In general, the proximal hand piece is provided with a tensioning control, for tightening and untightening the implant, and a release actuator for deploying the implant from the deployment catheter. The tensioning control may take any of a variety of forms, such as rotatable knobs or wheels, slidable levers, switches, buttons, knobs or other electrical control for controlling a motor drive on the rotatable driver, or others as will be apparent in view of the disclosure herein. Similarly, the release actuator may take any of a variety of forms, depending upon the construction of the release mechanism. In general, any of a variety of axially movable sliders, switches, levers, or rotatable collars, wheels or knobs may be utilized to control the release actuator. As a safety feature, any of a variety of locks may be provided, to prevent premature release of the implant.

In addition, the proximal control may be provided with any of a variety of auxiliary ports, such as a proximal guide wire port in an over the wire construction, and infusion ports for the infusion of medications, contrast media or other materials depending upon the intended functionality of the device.

FIGS. 19 and 20 illustrate the slot pattern on an alternative implant 600, similar to those described above, incorporating a plurality of voids 602 to influence the movement of the implant 600 from a delivery configuration to a remodeling configuration. FIG. 19 illustrates a plan view of a preferred void 602 arrangement, wherein 57 individual voids 602 are provided. In general, a first side of the implant is generally non-compressible, such as is achieved by the use of a tubular wall. The first side of the implant is radially opposite a second side of the implant, which is provided with the plurality of voids 602. The voids permit the second side of the implant to be axially expanded or contracted, thereby curving the implant as will be apparent to those of skill in the art. The number and configuration of the voids 602 will influence the bending characteristics of the implant. In general, voids which are transverse to the longitudinal axis of the implant can assist in plane bending of the implant. For most implants intended for positioning within the coronary sinus, and therefore having an axial length of within the range of from about 5 to about 16 cm, at least about 10 and often at least about 20 voids are provided. Thirty or forty or more voids may also be provided, depending upon the desired finished curvature of the implanted device as well as the dimensions of the voids and intervening solid wall material.

FIG. 20 is an enlarged view of a series of adjacent voids 602. As in the embodiments described above, a plurality of voids 602 are arranged axially along the implant 600 and are positioned substantially transverse to the longitudinal axis of the implant 600. Desirably, the voids 602 extend around at least about 180° of the circumference of the implant 600 and, preferably, around at least approximately 300° of the circumference. In some embodiments, the voids 602 extend around between approximately 300° and 315° of the circumference of the implant 600. Alternatively, the tubular body of the implant may comprise a spring coil in which adjacent windings are slightly spaced apart. Axial column strength on the first side of the implant is provided by an axially extending support such as a flexible ribbon or core wire which may be soldered or otherwise attached to the spring coil to inhibit axial compression along the side which carries the support. The opposing side of the coil may be compressed or expanded, to impart a curve. The coil may be provided with an outer polymeric sleeve.

Desirably, both ends of each void 602 terminate in a curved void portion such as circular void end portion 603. Advantageously, the end portions 603 of the void 602 reduce stress concentrations at the ends of the voids 602 that result from bending of the implant 600 from a delivery configuration to a remodeling configuration. In one implementation, the end portions 603 have a diameter of approximately 0.018 inches and a circumferential distance between the centers of the two opposing circular portions 603 of a single void 602 is approximately 0.068 inches. This feature decreases the likelihood of cracks originating in the material of the implant 600 at the ends of the voids 602.

Each void 602 is defined as a space between two opposing edge surfaces 604, 606 of the body of the implant 600. Surface 604 includes an axially extending projection such as substantially "U-shaped" projection 608 positioned within a complementary, substantially "U-shaped" recess 610 of surface 606. Alternative complementary configurations such as a chevron may also be used. An axis $A_V$ of both the projection 608 and the complementary recess 610 is substantially parallel to the longitudinal axis of the implant 402.

An axial distance between the substantially transverse edges 604, 606 defines a width $W_V$ of the void 602. The $W_V$ of the void 602 may be varied, depending upon the desired performance. In general, widths within the range of from about 0.010 to about 0.040 inches are often used. In the illustrated embodiment, the width $W_V$ is approximately 0.012 inches. Desirably, a distance between at least a portion of both sides of the projection 608 and recess 610 is less than the void width $W_V$ and defines a pair of interference portions 612 between the surface 604 and the surface 606.

The interference portions 612 inhibit the implant 600 from moving out of a plane defined by the longitudinal axis of the implant 600 as it moves from a delivery configuration to a remodeling configuration. Advantageously, the surfaces 604, 606 contact one another in the interference portions 612 of the void 602 in response to a force urging the implant 600 to curve out of plane. Thus, with the illustrated arrangement, the implant 600 is maintained within the desired plane while moving from a delivery configuration to a remodeling configuration. Alternatively, the void 602 may be configured to permit a predetermined out of plane movement of the implant 600 if such is desirable, as will be appreciated by one of skill in the art. For example, only one interference portion 612 may be provided to impart a controlled rotational bend, or the distance between the surfaces 604, 606 may be increased or decreased in the interference portion 612.

Any of a variety of alternative implant body structures may be utilized, as will be apparent to those of skill in the art in view of the disclosure herein. In general, the body is transformable from a flexible, implantation orientation to a curved, implanted orientation. The specific void pattern or other structure for facilitating curvature may be varied, depending upon the desired manufacturing techniques and clinical performance. In addition, any of a variety of alignment structures may be utilized, to influence the shape of the implant in the implanted orientation. Although slot patterns have been described above which facilitate in plane bending of the implant, the same structures may be repositioned along the length of the implant in a manner that produces compound curvatures or other out-of-plane bending as the implant is changed to the implanted orientation.

Figure 21:
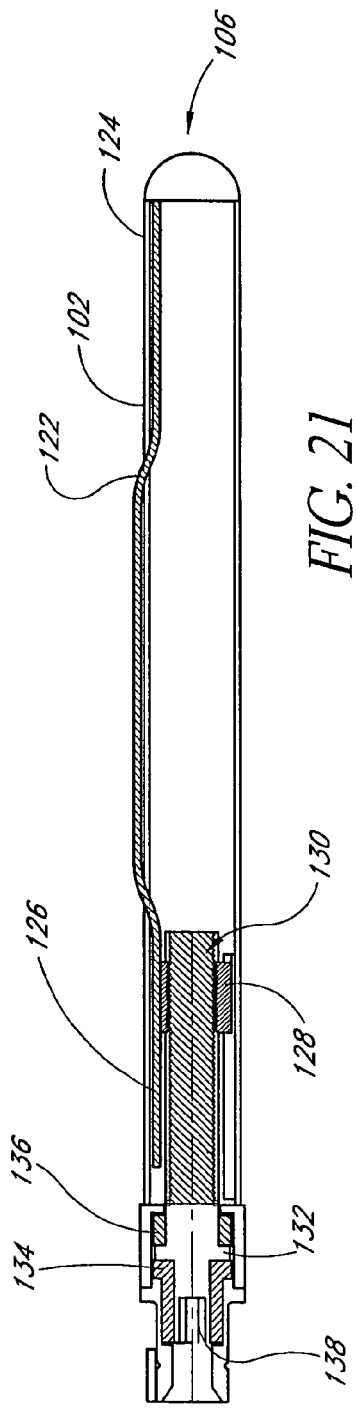
FIG. 21 is a cross sectional view of another implant in accordance with the present invention.
Figure 22:
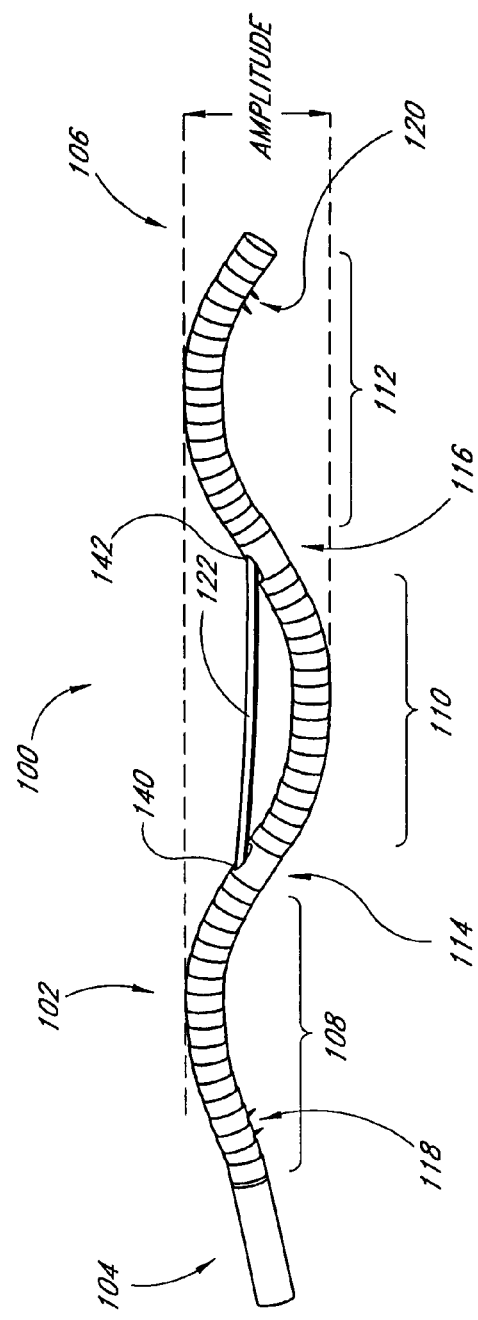
FIG. 22 is a side elevational view of the device of FIG. 21, in an actuated orientation.

Referring to FIGS. 21 and 22, there is illustrated an implant 100 in accordance with another aspect of the present invention. The implant 100 is adapted for positioning within or adjacent the coronary sinus, and for maintaining a compressive force on an aspect of the mitral valve annulus. The implant 100 comprises an elongate flexible body 102 having a proximal end 104 and a distal end 106. The body 102 may be constructed in any of a variety of manners, utilizing structures, materials and dimensions previously disclosed herein. In general, the body 102 is flexible such that it may be transluminally navigated to a deployment site such as within the coronary sinus. Alternatively, the implant may be advanced through tissue to a position outside of the coronary sinus such as within the wall of the heart or adjacent an exterior surface of the heart. The body 102 may thereafter be manipulated such that it imparts a compressive force on at least a portion of the mitral valve annulus, and the body 102 may be locked or restrained in the second configuration.

As illustrated in FIG. 22, the body 102 may be considered to comprise a proximal segment 108, a central segment 110 and a distal segment 112. In the implanted orientation, as illustrated, the proximal segment 108 and the distal segment 112 are concave in a first direction, and the central segment 110 is concave in a second direction. This configuration additionally comprises at least a first transition 114 between the proximal segment 108 and central segment 110, and a second transition 116 in between the central segment 110 and the distal segment 112.

In the illustrated embodiment, the curvature of the proximal segment, central segment and distal segment reside in a single plane. However, the central segment 110 may reside in a plane which is rotationally offset from the plane which contains the proximal segment 108 and distal segment 112, depending upon the desired clinical performance and deployment site.

The implant 100 preferably additionally comprises one or more anchors, for retaining the body 102 at a deployment site. In the illustrated embodiment, at least one and, in some embodiments two or four or more proximal anchors 118 are carried by the proximal segment 108. In addition, at least one, and, in certain embodiments at least two or four or more distal anchors 120 are carried by the distal segment 112. In the illustrated embodiment, first and second proximal anchors 118 and first and second distal anchors 120 are provided.

The proximal anchors 118 and distal anchors 120 are provided on a first side of the body 102, which is the same side as the convex side of the central segment 110 when in the implanted orientation. In this orientation, the first side of the implant 100 is configured to reside against the wall of the inside radius of curvature of the coronary sinus. The proximal anchor 118 and distal anchor 120 engage the vessel wall on the mitral valve side of the coronary sinus, allowing advancement of the central segment 110 from the first side laterally to apply a compressive force to at least a portion of the mitral valve annulus.

Any of a variety of engagement structures such as proximal anchor 118 and distal anchor 120 may be utilized to retain the implant 100 against the wall of the coronary sinus. Alternatively, the implant 100 may be configured to "push off" of the opposing wall of the coronary sinus, to support advancement of central segment 110 in the direction of the mitral valve. For example, the proximal segment 108 and distal segment 112 may be configured to extend all the way across the diameter of the coronary sinus, to contact the opposing wall. This may be accomplished by remodeling the device such that the amplitude equals or exceeds the diameter of the coronary sinus. Alternatively, the proximal and distal anchors 118, 120 may take the form of a tubular structure such as a self-expanding stent, or a stent which is expanded by a dilatation balloon or other expansion structure. The tubular anchor will then restrain the implant 100 in a desired orientation within the coronary sinus. As a further alternative, the proximal and distal ends of the implant may be extended through the wall of the coronary sinus, or stitched to or otherwise adhered to the wall of the coronary sinus, to permit the remodeling described herein. Additional alternative anchor configurations will be disclosed below.

Figure 23:
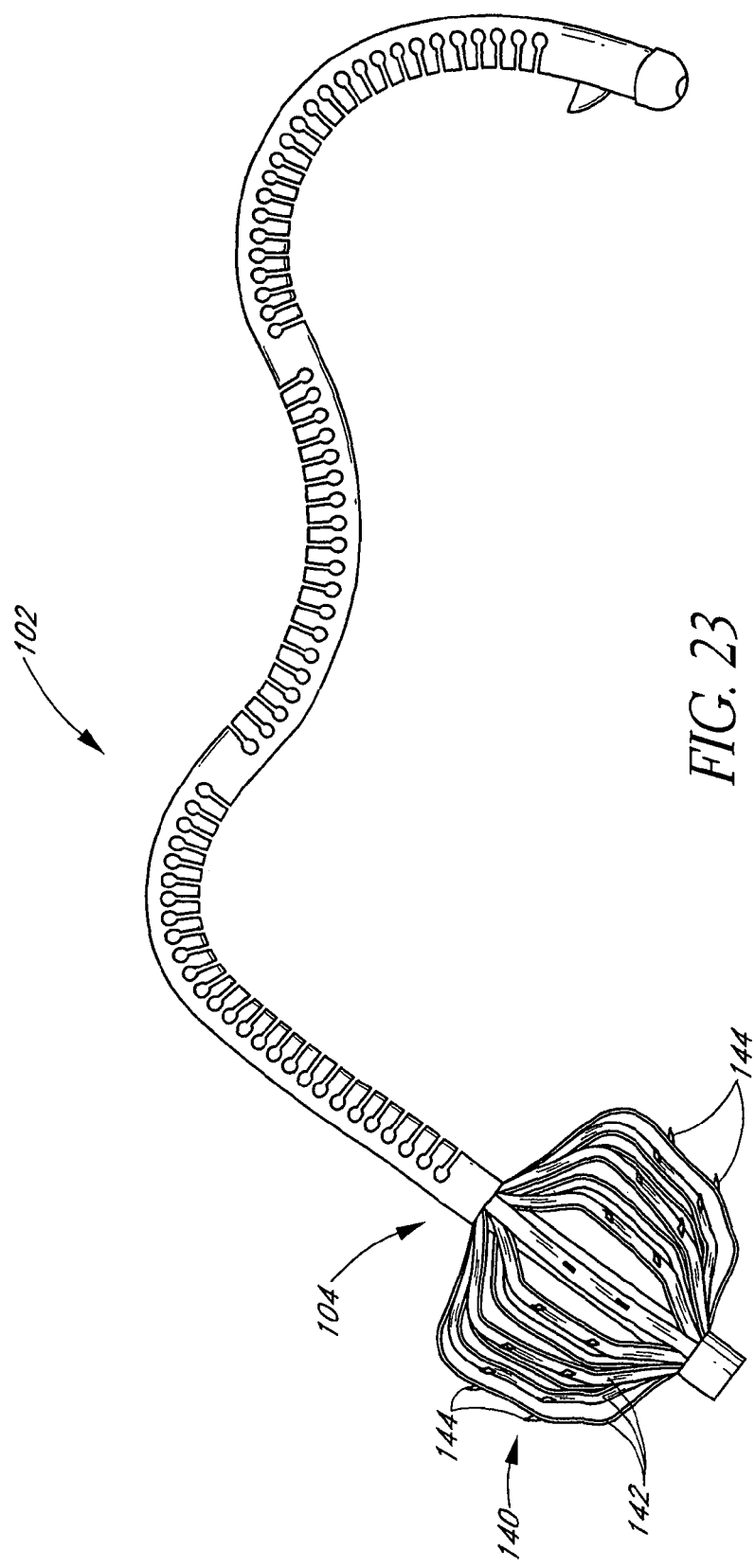
FIG. 23 is a side elevational view of an implant similar to that shown in FIG. 22, in the implanted configuration, having an expandable basket thereon for securement in a vessel.

Any of a variety of self expanding or mechanically expandable structures may be provided on the tubular body 102, to assist in anchoring and positioning the implant. For example, referring to FIG. 23, the proximal end 104 of the tubular body 102 is provided with a radially expandable support 140. In general, support 140 comprises a plurality of axially extending ribs or elements 142, each of which may be additionally provided with one or more barbs 144. Additional structural details of suitable support structures may be found by reference to U.S. patent application Ser. No. 10/033,371 filed on Oct. 19, 2001 and entitled "Adjustable Left Atrial Appendage Occlusion Device," published on Aug. 15, 2002 as Publication No. US 2002/0111647A1, the disclosure of which is incorporated in its entirety herein by reference.

Referring to FIGS. 21 and 22, the implant 100 comprises an elongate forming element 122 which has been described in various forms previously. The forming element 122 extends between a distal point of attachment 124 to the body 102 and a proximal point of attachment 126 to a threaded collar or other axially moveable structure. Proximal movement of the proximal point of attachment 126 with respect to the body 102 induces a curvature in the implant 100 as has been discussed.

In the illustrated configuration, the forming element 122 is attached at the proximal point of attachment to a threaded structure such as a nut 128. Alternatively, threads may be provided directly on a proximal portion of the forming element. Nut 128 is axially movably carried by a rotatable screw 130, using well understood complementary threaded engagement surfaces. Rotation of the screw 130 will cause relative axial movement of the nut 128 as will be understood by those of skill in the art.

The screw 130 is provided with one or more axial retention structures to permit rotation but inhibit axial movement thereof. In the illustrated embodiment, the screw 130 is provided with one or more radially outwardly extending projections such as flange 132, which is captured between a first bushing 134 and a second bushing 136 to prevent axial movement. Screw 130 may be retained against axial motion while permitting rotation using any of a variety of alternative structures, such as radially inwardly extending tabs or flanges from the inside surface of the body 102, which are slidably received by one or more radially inwardly extending annular grooves in the screw 130.

The proximal end of the screw 130 is provided with a rotational coupling 138. Coupling 138 is adapted to removably receive a rotatable driver carried by the deployment catheter such that rotation of the driver within the deployment catheter will produce axial movement of the nut 128. In one implementation, the coupling 138 comprises a recess having a non-round cross-sectional configuration, such as a hexagonal wall. This cooperates with the hexagonal distal end on the driver (disclosed previously herein) to produce a removable rotational coupling.

In the embodiment illustrated by FIG. 22, the forming element 122 extends through the inside of the body 102 in each of the proximal segment 108 and distal segment 112, and extends along the outside of the body 102 along the central segment 110. See also FIG. 21. This configuration, in which the forming element 122 extends through a first aperture 140 in or near the proximal transition 114, and a second aperture 142 in or near the distal transition 116, has been found to be convenient in an implant adapted to assume a "w" implanted configuration as shown in FIG. 21. Alternatively, the forming element 122 may extend along the inside of the body 102 throughout its length. The forming element 122 may extend along the outside of the body 102 throughout its length, or extend partially inside and partially outside of the body 102 depending upon the desired performance characteristics of the implant.

In connection with any of the preceding embodiments, it may be desirable for the implant to change in axial length as it is advanced from the first, flexible configuration for transluminal delivery, to the second configuration for remodeling the mitral valve annulus. This may be accomplished in a variety of ways, such as configuring two or more sections of the tubular body in a telescoping fashion, such that a first portion of the body is axially moveably positioned within a second portion of the body. This enables the axial length of the body to be controllably altered, during or apart from the transformation of the device to its implanted configuration. In certain applications, it may be desirable for the axial length of the implant to shorten as the implant is converted to its implanted orientation. Foreshortening of the implant by a distance within the range of from about 10% to about 95% of the maximum implant axial length is presently contemplated.

Figure 24:
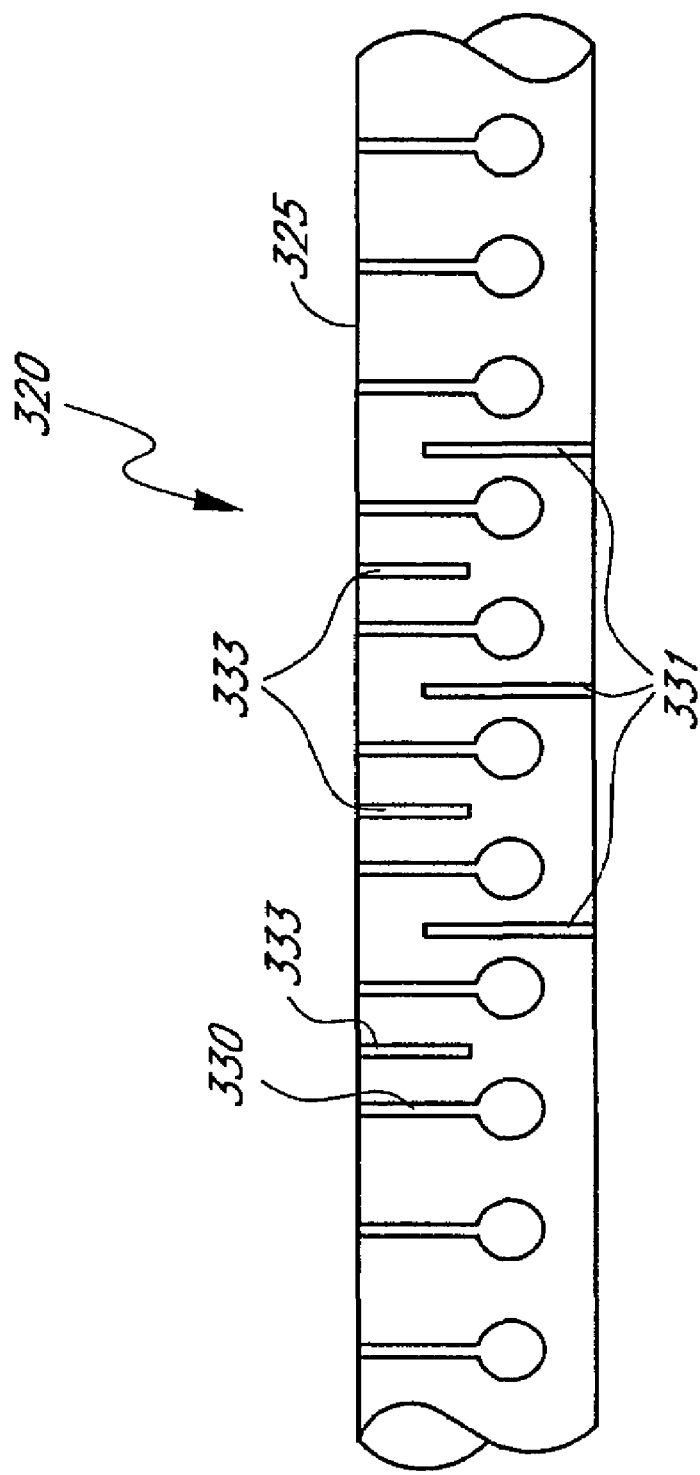
FIG. 24 is a side elevational fragmentary view of an implant, illustrating a plurality of axial foreshortening voids.

In one embodiment, controlled foreshortening may be accomplished by providing a plurality of foreshortening slots or chevrons in the outer wall of the tubular body. Referring to FIG. 24, there is illustrated a fragmentary view of a portion of an elongate body 320. The configuration of FIG. 24 can be applied to any of the previously disclosed embodiments, as will be apparent to those of skill in the art in view of the disclosure herein.

The elongate body 320 includes a plurality of transverse voids 330 as has been discussed. Axial compression of the elongate body 320 causes the voids 330 to axially close, thereby deflecting the elongate body 320 out of plane. In some of the previously disclosed devices, the voids 330 are aligned on a first side of the elongate body 320, and they oppose a second side of the elongate body 320 which is comparatively non collapsible and thereby acts as a spine for the device.

In accordance with the present, foreshortening feature, a first plurality of foreshortening voids 331 is provided on the elongate body 320. The foreshortening voids 331 are positioned on the elongate body 320 such that they permit axial compression of the body, upon application of the axially compressive force utilized to deflect the body out of plane. In the illustrated embodiment, the first plurality of foreshortening void 331 is axially aligned along the "backbone" or support side of the device, opposite to the voids 330.

A second plurality of foreshortening voids 333 may also be provided, spaced circumferentially apart from the first plurality of foreshortening voids 331. In the illustrated embodiment, the first and second foreshortening voids 331 and 333 are aligned along first and second longitudinal axes, which are spaced approximately 180° apart from each other around the circumference of the elongate body 320.

In general, foreshortening within the range of from about 1% to about 20% of the maximum length of the device is presently contemplated. The specific number and dimensions of the foreshortening voids may be optimized by those of skill in the art in view of the disclosure herein, taking into account the desired clinical performance.

Figure 25:
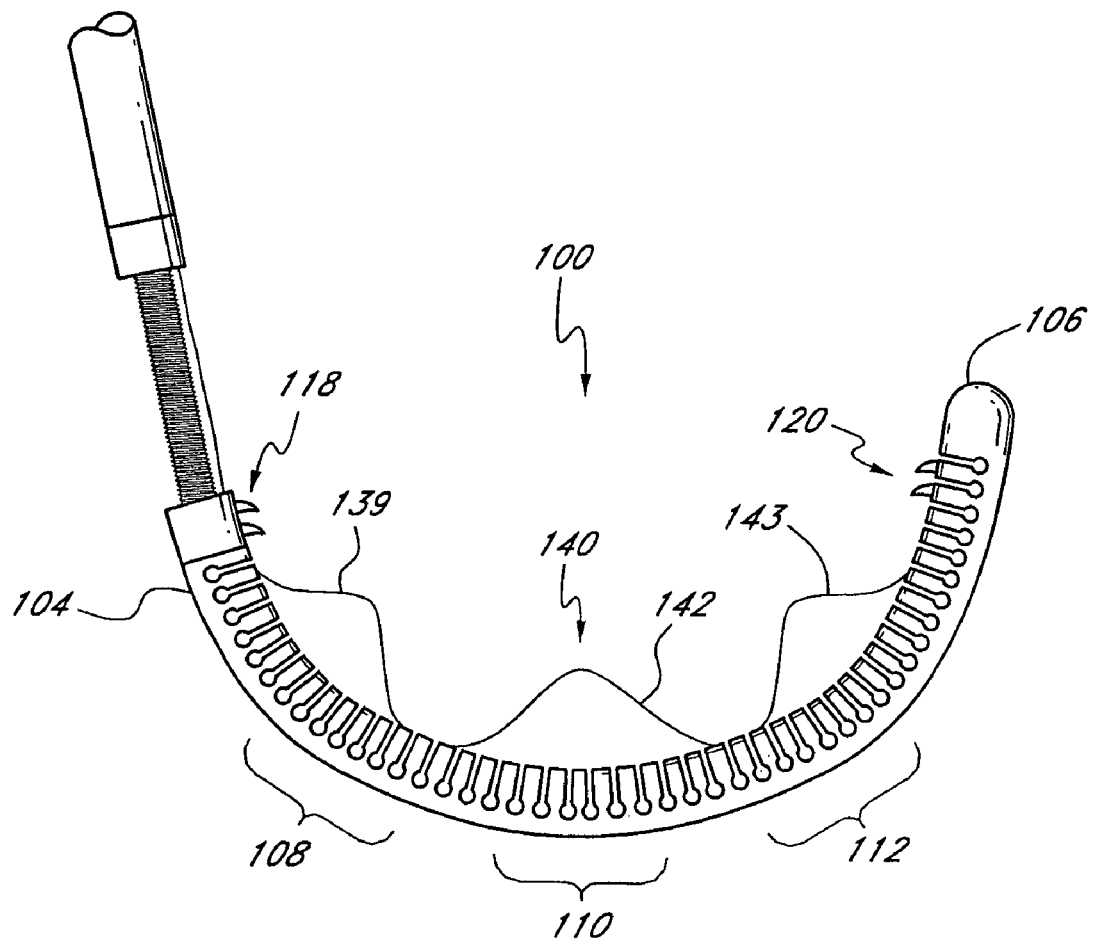
FIG. 25 is a side elevational view of an implant in accordance with the present invention, having a plurality of compression elements and/or securement members thereon.

Referring to FIG. 25, there is illustrated an alternate construction of the implant 100 in accordance with the present invention, for accomplishing the radial inward compression previously discussed in connection with FIG. 22. The implant 100 extends between a proximal end 104 and a distal end 106. The implant may be considered to be divided into two or more distinct zones, such as a central segment 110 and proximal and distal segments 108 and 112. At least one segment on the implant 100 includes a compression element 140, configured to generate radial compression such as against the posterior leaflet of the mitral valve. In the illustrated design, the compression element 140 comprises a flexible ribbon 142. The flexible ribbon 142 is configured to project radially inwardly from the concave side of the implanted device 100, as the device 100 is transformed from its implantation configuration to its implanted configuration. In one embodiment, the ribbon 142 comprises a flat wire having a cross section of about 0.005 inches by about 0.020 inches, and having an axial length of from about 3 to about 4 cm.

Ribbon 142 may be configured to provide a radially outwardly directed compressive force using any of a variety of mechanisms. In one implementation, the ribbon 142 has a fixed length and is attached at first and second points spaced apart along the length of the implant 100. As the concave side of the implant 100 axially shortens, the fixed axial length of the ribbon 142 causes a preset bend to progress laterally outwardly in response to the bending of the implant. Alternatively, the compression element 140 may be activated in response to an active control, such as rotation of a threaded screw or movement of an axially moveable control.

In addition to a central compression element 140, additional compression elements may be provided. In the embodiment illustrated in FIG. 25, a proximal compression element 139 and a distal compression element 143 are also provided. The desirability of two or three or more compression elements 140 spaced axially apart along the implant depends upon the desired clinical performance of the device.

In addition to the compression element 140, the implant 100 illustrated in FIG. 25 additionally carries one or two or more proximal tissue anchors 118 and distal tissue anchors 120. Preferably, the proximal anchors 118 and the distal anchors 120 are positioned fully within the tubular body of the implant 100 during transluminal navigation. The proximal anchors 118 and distal anchors 120 are extended radially outwardly from the implant 100 in an inclined orientation to engage tissue at the time of deployment, such as simultaneously with the transformation of the implant 100 from the implantation orientation to the implanted orientation. Additional details of particular anchor configurations and deployment sequences will be discussed below.

Figure 26:
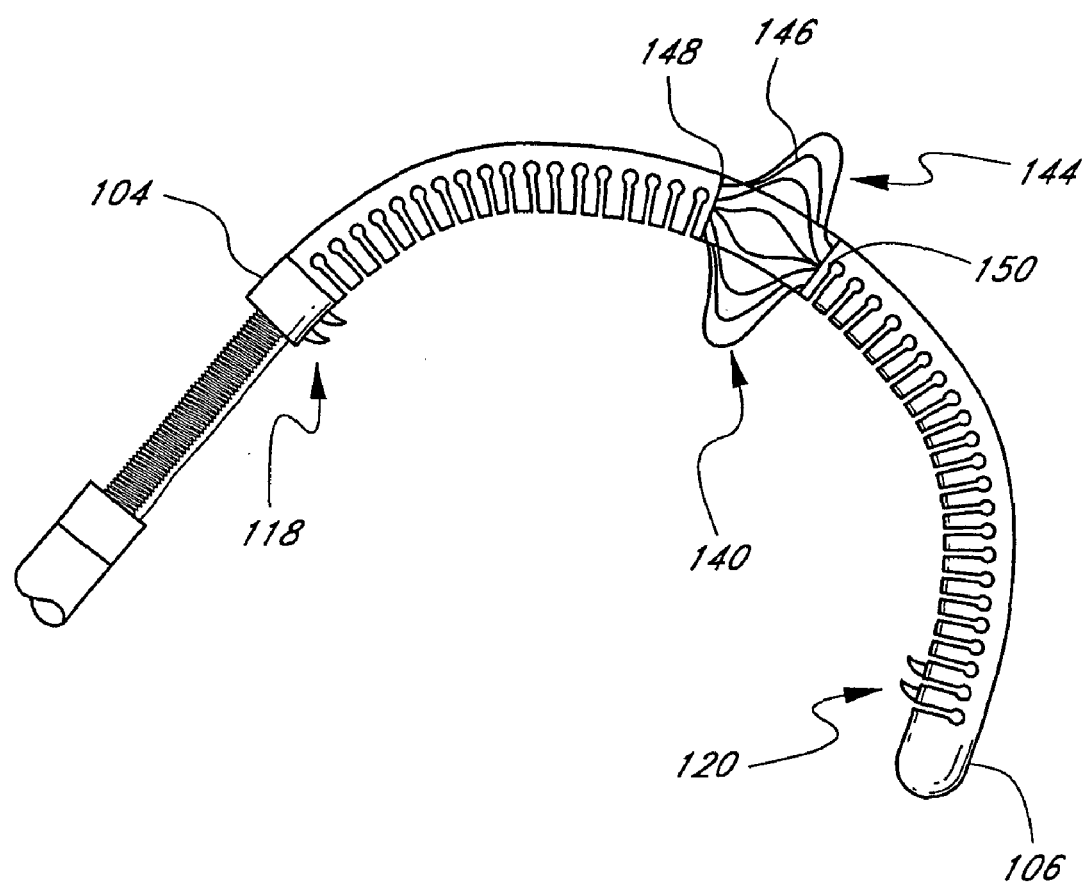
FIG. 26 is a side elevational view of an implant in accordance with the present invention, having an alternate compression element thereon.

Referring to FIG. 26, there is illustrated an alternate construction for the compression element 140. In this construction, the compression element 140 comprises a basket or other structure which extends radially outwardly in response to axially compressive movement. The basket 144 comprises a plurality of axially extending ribs 146 connected to the implant at a proximal hub 148 and distal hub 150. During tightening of the implant to compress the mitral valve annulus, the distal hub 150 and the proximal hub 148 are advanced towards each other, thereby axially shortening and radially expanding the wire basket 144. The basket may comprises two or three or more, and, preferably, at least about 6 axial ribbons 146. In one embodiment, the basket 144 is formed by providing a plurality of axially extending slots around the circumference of a metal tube. Any of a variety of medically compatible metals may be used, such as stainless steel, or nickel titanium alloys such as nitinol. The radially expandable support structure illustrated in FIG. 23 may also be positioned on the implant in a central segment, to function as a compression element 140.

Figure 27:
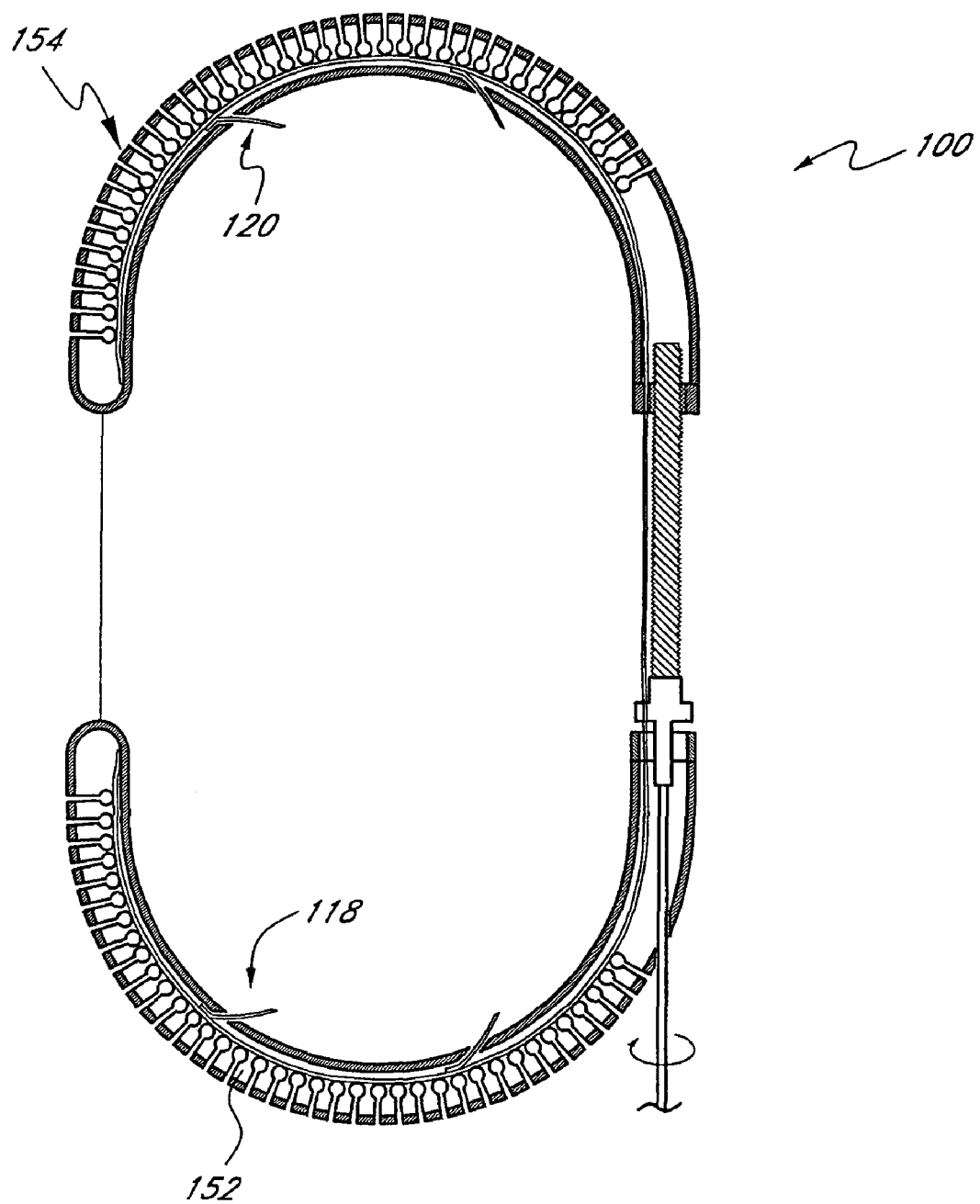
FIG. 27 is a side elevational view of an alternative implant in accordance with the present invention.
Figure 28:
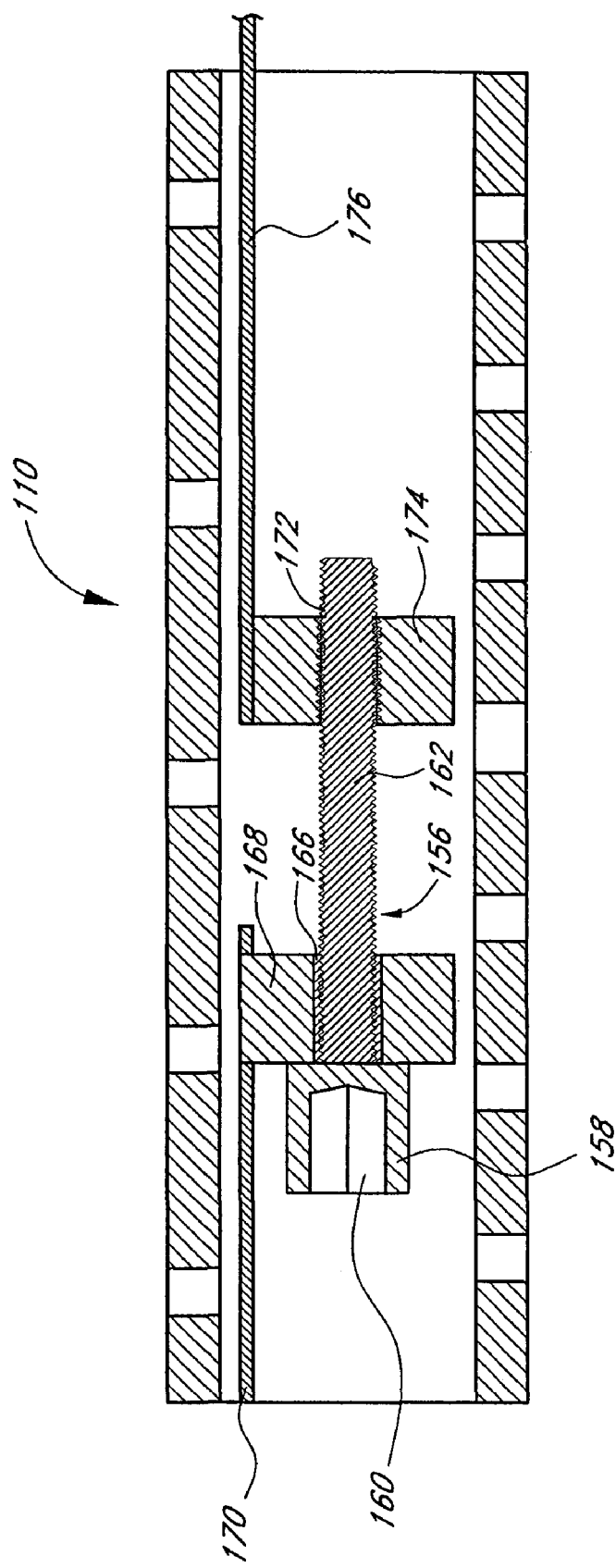
FIG. 28 is an enlarged fragmentary cross sectional view of a portion of the implant illustrated in FIG. 27.

Referring to FIGS. 27 and 28, there is illustrated a further variation of the present invention. In this construction, the implant 100 comprises a proximal section 152 and a distal section 154. The bending mechanism has been relocated to the center of the device, and is illustrated as including a rotatable screw 156. The screw is rotated in response to rotation of a component 157 on a deployment device which is removably connectable to the rotatable screw. The component 157 on the deployment device is coupled to a rotatable driver positioned within the implant 100 and further rotatably coupled to the screw 156. Thus, a rotational force on the component 157 is translated to the rotatable driver 159 within the deployment device which causes the rotatable screw 156 to advance the proximal section 152 and the distal section 154 into the implanted configuration, as illustrated in FIG. 27. As the implant 100 is advanced toward the implanted configuration, one or more proximal anchors 118 and one or more distal anchors 120 are also deployed from the device 100, to engage tissue as has been discussed elsewhere herein.

An alternate tensioning assembly which may be used in a device like that illustrated in FIG. 27 is shown in an enlarged fragmentary view in FIG. 28. In general, the device 110 includes a rotatable screw 156. The rotatable screw 156 includes a proximal coupling 158, having a recess 160 or other releasable connector as has been discussed elsewhere herein. In one convenient construction, the recess 160 is provided with a polygonal cross section, such as to accommodate a hex coupling on the distal end of the deployment device (not shown). Any of a variety of complementary surface structures between the proximal coupling 158 and the deployment device may be utilized as has been discussed.

The proximal coupling 158 is connected to the threaded shaft 162. Threaded shaft 162 extends through an aperture 166 in a proximal block 168. Block 168 is attached to a proximal pull wire 170.

The threaded shaft 162 is threadably engaged within a threaded aperture 172 in a nut 174. The nut 174 is connected to a distal pull wire 176, which extends through the distal section of the implant 100. The proximal pull wire 170 extends proximally though the device to a point of attachment with respect to the tubular body, and the distal pull wire 176 extends distally to a point of attachment with respect to the tubular body.

As will be appreciated in view of the previous disclosure herein, rotation of the proximal coupling 158 will cause the threaded shaft 162 to rotate freely with respect to the aperture 166 in the proximal block 168, and to axially advance the nut 174 within the implant 110. Preferably, the aperture 166 in the proximal block 168 and the inner threads of the nut 174 are oppositely threaded with respect to one another such that the effect of rotation of the proximal coupling 158 in a first direction is to decrease the distance between the proximal block 168 and the nut 174. Of course, the threaded shaft 162 is appropriately configured with cooperating threads as will be apparent to one of ordinary skill in the art. This will have the effect of bending both the proximal section 152 and distal section 154 into the curved orientation illustrated in FIG. 27. In the illustrated construction, axial advancement of the proximal block 168 and the nut 174 towards each other will also deploy the proximal tissue anchors 118 and distal anchors 120. Preferably, the length of the threaded shaft 162 is configured such that a previously selected maximum number of rotations in a first direction cause the proximal block 168 and nut 174 to contact each other and interfere with further rotation of the screw 156. Thus, the maximum displacement of the proximal pull wire 170 and distal pull wire 176 can be selectively controlled thereby limiting the deflection of the proximal section 152 and the distal section 154 to a final desired shape.

Rotation of the proximal coupling 158 in a second, opposite direction will allow the implant to straighten out and become flexible again, such as to permit repositioning, retensioning, or removal. The rotational limit of the screw 156 in a second direction can be controlled by the interference of the proximal block 168 against the proximal coupling 158. As the screw 156 is rotated in a second direction and reaches its maximum rotation, the proximal block 168 contacts the proximal coupling and thereby inhibits any further screw rotation in the second direction.

The operation of the tissue anchors may be accomplished in any of a variety of ways, as will be apparent to those of skill in the art in view of the disclosure herein. One construction may be understood by reference to FIG. 29. In this construction, the distal anchors 120 are automatically deployed in response to proximal retraction of the distal pull wire 176.

Figure 29:
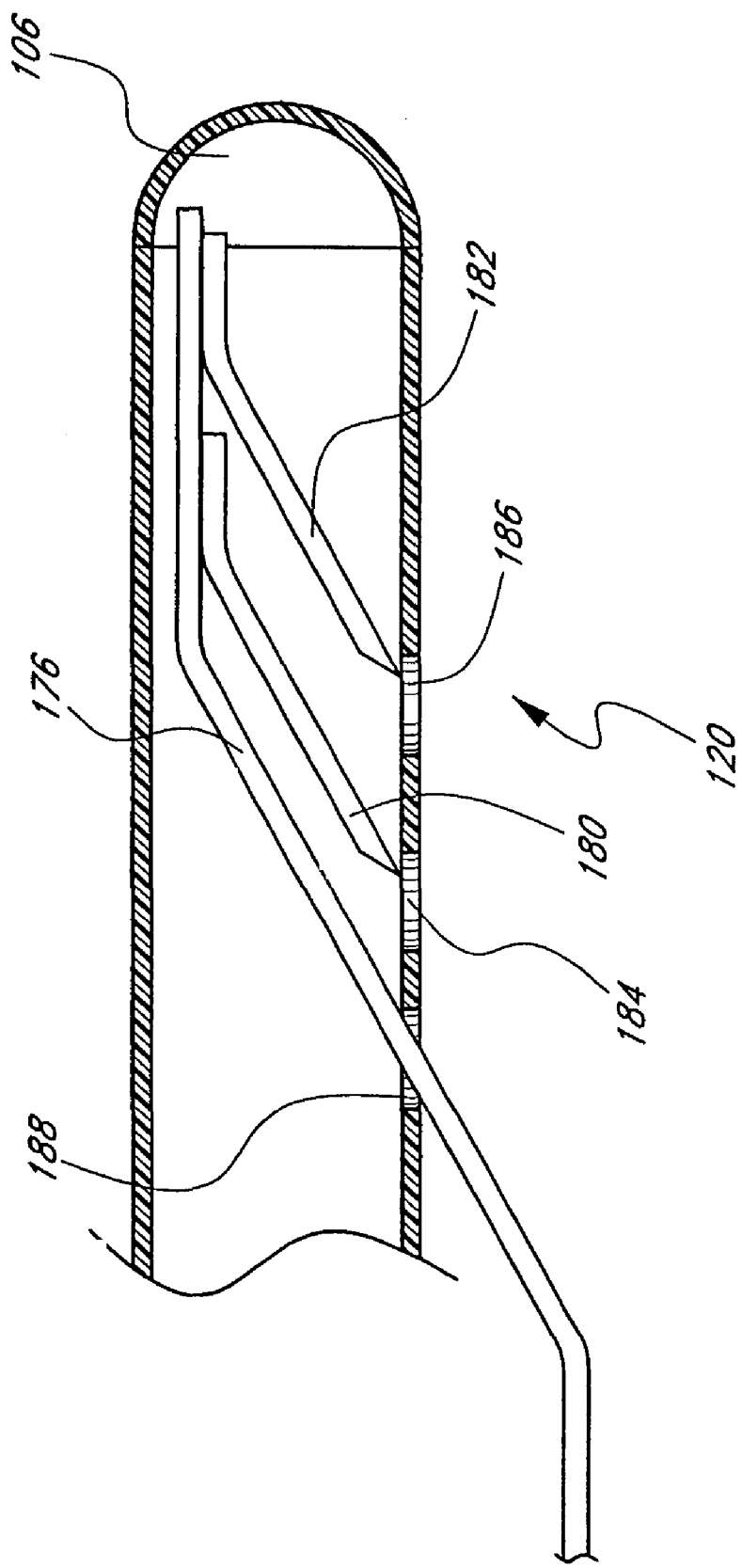
FIG. 29 is a cross sectional fragmentary view of a distal anchor assembly in accordance with the present invention.

Referring the FIG. 29, the distal pull wire 176 is provided with at least a first tissue barb 180 and optimally a second tissue barb 182. Additional barbs may be provided as desired. Tissue barbs 180 and 182 are inclined laterally in the proximal direction, and are aligned with openings 184 and 186, respectively, in the side wall of the implant 100. Proximal retraction of the distal pull wire 176 causes the tissue barbs 180 and 182 to advance laterally through the openings 184 and 186, at an angle which is inclined in the proximal direction, to engage tissue. Each of the tissue barbs 180 and 182 may be provided with a sharpened distal end, to facilitate penetrating tissue.

The distal pull wire 176 may extend proximally to the nut 174 as discussed in connection with FIG. 28. Alternatively, the distal pull wire 176 may extend all the way to the proximal end of the implant 110, depending upon the design of the tightening mechanism.

In the embodiment illustrated in FIG. 29, the distal pull wire 176 exits the tubular body at an aperture 188, and extends along the outside surface of the implant 100 on the concave side of the device when in the implanted orientation. Alternatively, the distal pull wire 176 may extend within the implant 100 throughout the length of the distal pull wire 176. The proximal anchor 118 may be constructed in a similar manner, as will be apparent to those of skill in the art.

When fully deployed, each of the tissue barbs 180 and 182 extend outwardly from the side of the implant for a distance within the range of from about 1 mm to about 5 mm. By adjusting the angle between the longitudinal axis of the barb 180 and the longitudinal axis of the implant, the length of the barb 180 can be adjusted while maintaining the lateral distance that the barb 180 may travel within the desired range.

In certain applications of the invention, it may be desirable to control the sequence by which the distal anchors and/or proximal anchors deploy, relative to the transformation of the implant from the implantation orientation to the implanted orientation. For example, it may be desirable for the distal anchors 120 to deploy into the wall of the coronary sinus prior to the implant placing any substantial compressive pressure on the mitral valve annulus. Following compression of the annulus, the proximal anchors may desirably be deployed. Alternatively, it may be desirable to deploy both the proximal and distal anchors at the beginning of the compression cycle, to be followed by the application of pressure by the implant on the mitral valve annulus. Additionally, the proximal and/or distal anchors can be deployed before compression of the annulus. This sequence can be controlled in any of a variety of ways, such as by providing a mismatch between the angle of the barbs 180 and 182 within the implant, and the apertures 184 and 186 through which the barbs will travel. Providing friction to the deployment of the barbs will tend to delay deployment of the barbs until a sufficient tension force has been applied to the distal pull wire 176. Alternatively, by configuring the pull wire 176 and barbs 180 and 182 for minimal deployment friction, the barbs will tend to deploy prior to the application of significant compressive force on the mitral valve annulus. The sequence may be optimized by those of skill in the art in view of the desired clinical performance.

Although the foregoing embodiments have been described primarily in terms of a structure having a tubular housing with various components therein, the invention may be accomplished using a nontubular structure such as a pair of adjacent axial elements. In general, the lateral bending and compression functions of the invention can be accomplished as long as a first elongate flexible structure provides column strength, and a second forming element is attached near a distal end of the column strength element. Proximal axial retraction of the forming element will cause a lateral deflection of the column strength element, provided proximal movement of the column strength element is inhibited. Similarly, axial distal advancement of the forming element, if it is selected such that it has a sufficient column strength, will cause a lateral deflection of the column strength element in an opposite direction. The column strength element may be in the form of a ribbon, wire, bottomed out spring, or other element which will resist collapse under tension. In the foregoing embodiments, one side wall of the tubular body provides column strength, and the forming element operates as a pull wire such that proximal retraction of the pull wire causes a lateral deflection of the column strength element.

Figure 30B:
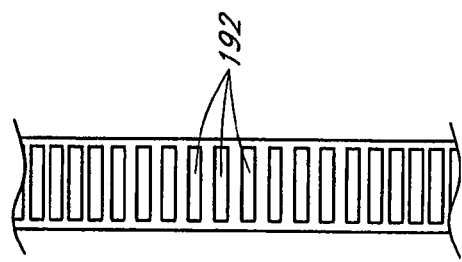
FIGS. 30A and 30B are schematic views of an alternate implant in accordance with the present invention.
Figure 30A:
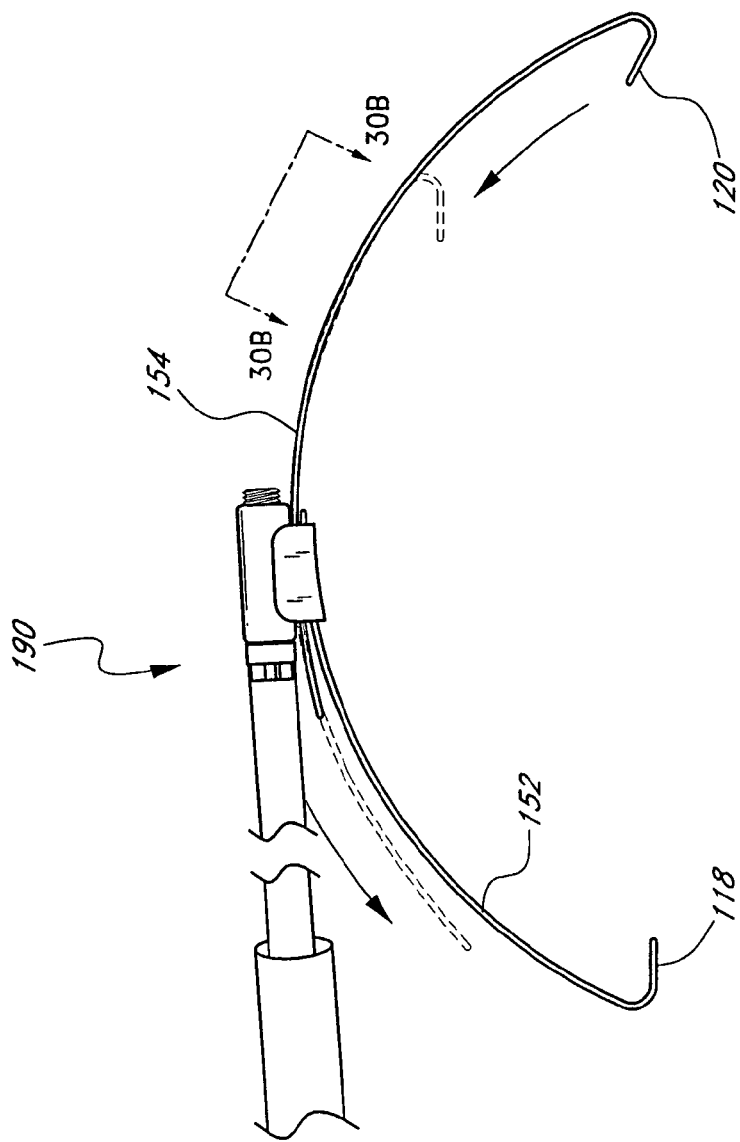

A further implementation of the invention may be understood by reference to FIGS. 30A and 30B. In this construction, a distal section 154 has one or more tissue anchors 120, and a proximal section 152 has one or more proximal tissue anchors 118. The distal tissue anchor 120 and/or the proximal tissue anchors 118 may either be passive (as illustrated) or active, such that the anchors are pivotably or angularly adjustably carried by the implant. Active tissue anchors may either incline in response to positioning or tightening of the device, or be controlled by a separate rotatable or axially moveable control element. The proximal tissue anchors 118 and distal tissue anchors 120 need not both be active or passive. For example, the distal tissue anchor may be actively engageable with the adjacent tissue such as by manipulation of a tissue engagement control. The proximal tissue anchor may be passively engageable with the adjacent tissue. The reverse may also be accomplished, where the distal tissue anchor is passively engageable with adjacent tissue and the proximal tissue anchor is controllably engageable utilizing a control on the deployment catheter. The foregoing discussion concerning the active or passive tissue anchors applies to all of the embodiments herein, as will be apparent to those of skill in the art in view of the disclosure herein.

A tensioning element 190 is provided at about a junction between the distal segment 154 and the proximal segment 152. The tensioning element 190 is adapted to apply tension between the proximal anchors 118 and the distal anchors 120.

In one construction, at least one of the proximal section 152 and distal section 154 comprises a plurality of transverse engagement structures such as slots. See FIG. 30B. The tensioning element 190 includes a rotatable threaded shaft (not shown), oriented such that the threads engage the transverse slots on the proximal or distal section. Rotation of the threaded shaft using any of a variety of rotatable engagement configurations disclosed elsewhere herein will cause axial movement of the corresponding proximal or distal section 152, 154, as will be understood by those of skill in the art.

In one particular embodiment, the proximal section 152 is secured to the tensioning element 190. The distal section 154 is axially moveably engaged with the tensioning structure 190 by engagement of one or more rotatable threads within the tensioning structure 190, in a plurality of transverse slots on the distal section 154. Rotation of a rotatable driver in a first direction will draw the distal anchor 120 in a proximal direction, thereby decreasing the distance between the proximal anchor 118 and the distal anchor 120. Alternatively, the distal section 154 may be fixed with respect to the tensioning element 190, and the proximal section 152 may be axially advanced or retracted based upon the rotation of a rotatable driver. In a further alternative, each of the proximal section 152 and the distal section 154 may engage a threaded shaft in the tensioning element 190, to enable the axial distance between the proximal anchor 118 and the distal anchor 120 to be adjusted.

Each of the proximal anchors 118 and distal anchors 120 may be either actively deployed such as has been described previously herein, or may be fixed with respect to their corresponding section 152, 154. In an embodiment in which the anchor is fixed with respect to its corresponding support section, the anchors are retracted within a deployment sleeve for transluminal navigation. The deployment sleeve is advanced distally through the coronary sinus to the distal point of attachment of distal anchor 120. Proximal retraction of the outer sleeve with respect to the implant will release the distal anchor 120, which may incline radially outwardly in the proximal direction due to its own internal bias. Proximal traction on the distal anchor 120 will cause the distal anchor to engage tissue at the distal attachment site. The outer tubular sleeve may be further proximally retracted to release the proximal anchor 118. Rotation of the rotatable driver following engagement of the anchors will apply compressive force to the mitral valve annulus. Any of a variety of lateral engagement structures, such as have been previously disclosed herein, may be adapted for use with the present embodiment, to focus pressure on a specific anatomical site such as the posterior leaflet of the mitral valve. See, for example, the compression element 140 illustrated in FIG. 25, and corresponding text.

For example, a compression element 140 may be formed from an elongate flexible ribbon extending along the concave side of at least one of the distal section 154 and proximal section 152. A proximal end of the compression element 140 may be secured with respect to the proximal section 152, and a distal end of the compression element 140 may be secured with respect to the distal section 154. Upon manipulation of the tensioning element 190 to reduce the axial length of the implant, the compression element 140 will extend radially inwardly from the concave side of the device.

In the foregoing embodiment, deployment of the compression element is responsive to shortening or tensioning of the device. In an alternate implementation of the invention, the lateral advance of the compression element 140 may be controlled independently of tensioning the tensioning element 190. In this embodiment, the tensioning element 190 may be adjusted to seat the proximal anchors 118 and distal anchors 120, and to apply a degree of tension on the mitral valve annulus. During or following the tensioning step, the compression element 140 may be laterally deployed. Lateral deployment may be accomplished by rotating a rotatable driver or axially moving an axial driver within the deployment catheter, inflating a laterally expandable balloon by way of an inflation lumen in the deployment catheter, or through any of a variety of structures which will become apparent to those of skill in the art in view of the disclosure herein.

There is provided in FIGS. 31A–C a partially cross-sectioned side elevational view of an alternate construction of an implant 900, similar to that illustrated in FIG. 30A. The implant 900 includes a proximal section 152, a distal section 154, and a tensioning element 190. The tensioning element 190 couples the proximal section 152 to the distal section 154, and is used to apply and release tension therebetween.

As illustrated in FIG. 31A, the proximal section 152 includes a proximal tissue anchor 118, and a proximal ribbon 902. The proximal tissue anchor 118 may be laser cut from stainless steel tube, and has an arcuate cross-sectional shape (not shown). Alternatively, any of a variety of tissue anchor designs and materials may be employed, as have been described in greater detail above, and as are known to those of skill in the art. In one embodiment, the proximal tissue anchor 118 includes a penetrating point 904, and two barbs 906 to hold the proximal tissue anchor 118 securely in place once deployed. A variety of penetrating points 904 and barbs 906 may be used to achieve desired clinical results, and the particular proximal tissue anchor 118 design may vary depending upon the particular clinical requirements.

The proximal tissue anchor 118 preferably includes two holes 908 that are used to partially rotatably couple the proximal tissue anchor 118 with a pivot 910 that is coupled to the proximal ribbon 902. One embodiment of such pivot 910 is shown in greater detail on FIG. 31C. The pivot 910 may be integral to the material of the proximal ribbon 902, or may include a pin, or other device coupled to the proximal ribbon 902. The proximal section 152 also includes a spring 912, used to bias the proximal tissue anchor 118 so that its penetrating point 904 rotates away from the proximal ribbon 902 and towards tissue when deployed. In one embodiment, the spring 912 is cut from the same tubing used to form the proximal tissue anchor 118, and is integral thereto. In another embodiment, the spring 912 has a torsional design, as is well known to those of skill in the art.

The overall length of the proximal tissue anchor 118 preferably is about 6 mm, although the actual length will be selected based upon the particular requirements of the clinical setting. In one embodiment, the length of the proximal tissue anchor 118 will be selected such that it does not penetrate all the way through the wall of the coronary sinus when deployed. In general, the length of the proximal tissue anchor 118 is in the range between about 1 mm and about 15 mm.

Distal section 154 preferably includes a distal tissue anchor 120, a distal ribbon 914, and a spring 912, as shown in FIG. 31A. Distal tissue anchor 120 is similar to proximal tissue anchor 118, and has similar characteristics and dimensions as described in greater detail above. Distal ribbon 914 preferably includes multiple slots 916 to interface with the tensioning element 190, as described in greater detail below. The slot 916 pitch, or center-to-center spacing of the slots 916, partially defines the resolution of the adjustability of the tension applicable between the proximal and distal tissue anchors 118, 120. In one embodiment, the slot pitch is about 1 mm. Alternatively, the slot pitch is between 0.1 mm and 3 mm. In another embodiment, the slot pitch is not constant along the length of the distal ribbon 914. The distal ribbon 914 may be designed to have a greater pitch, or slot width towards the proximal end of the distal ribbon 914, and a smaller pitch or slot width towards the distal end of the distal ribbon 914. Alternatively, the distal ribbon 914 may have no slots such that continuous instead of stepped movement of the distal ribbon 914 is used to apply tension between the proximal and distal tissue anchors 118, 120. The method of applying tension between the proximal and distal tissue anchors 118, 120 is described in greater detail below. The distal ribbon 914 also preferably includes a pull-wire disconnect 918 for removable coupling to a tab pull-wire 944, as described in greater detail below with reference to FIGS. 31E–F.

As shown in FIGS. 31A and 31B, the implant 900 also includes a tensioning element 190. In one embodiment, the tensioning element 190 includes a housing 920, latch 922, spacer 924, and insert 926. In one embodiment, the housing 920 is made from a section of stainless steel tubing, although housings 920 of other shapes and materials may be used. In one embodiment, the housing 920 is made from nickel titanium tubing. The proximal ribbon 902 preferably is attached to the inside lumen of the housing 920 using any of a variety of methods, including welding, bonding, or by using any of a variety of fasteners, as is well known to those of skill in the art. In one embodiment, the proximal ribbon 902 is attached to the housing 920 such that the axial position of the proximal tissue anchor 118 is fixed with respect to the housing 920.

The housing 920 also includes a latch 922 that preferably is attached to a spacer 924 at the latch's 922 distal end. The latch 922 includes a tang 928 that bends towards the distal ribbon 914 at an angle relative to the distal ribbon 914. The tang 928 is designed to travel through an opening 930 in the spacer 924, and engage a slot 916 in the distal ribbon 914. By engaging the slot 916 in the distal ribbon 914, the latch 922 prevents axial movement of the distal ribbon 914, and distal tissue anchor 120, in the distal direction. The opening 930 in the spacer 924 is of sufficient dimension to allow the tang 928 of the latch 922 to flex enough to disengage the slot 916 in the distal ribbon 914 when the distal ribbon 914 is moved in the proximal direction. The interface between the latch 922 of the tensioning element 190 and the slot 916 of the distal ribbon 914 functions as a ratcheting mechanism. The ratcheting mechanism allows stepped movement of the distal ribbon 914 as it is moved in the proximal direction (as described in greater detail below), yet prevents the distal ribbon 914 from moving in the distal direction. The amount of movement of each ratcheting step is related to the pitch between the distal ribbon 914 slots 916, as described above.

In another embodiment, as mentioned above, the distal ribbon 914 does not contain slots. In such embodiment, friction between the tang 928 of the latch 922 and the distal ribbon 914 is sufficient to allow continuous, e.g., non-stepped, or infinitely adjustable, movement of the distal ribbon 914 in the proximal direction, yet prevent movement of the distal ribbon 914 in the distal direction. In another embodiment, shallow depressions, ribs or other texture, or partial thickness slots are added to the surface of distal ribbon 914 to provide enhanced friction against tang 928. In one embodiment, movement of the distal ribbon 914 in the proximal direction may be achieved by releasing, or disengaging the tang 928 of the latch 922 from the distal ribbon 914.

In one embodiment, the housing 920 also includes a latch release ribbon 932 that preferably is disposed between the spacer 924 and the distal ribbon 914, as illustrated in FIG. 31A. The latch release ribbon 932 is also axially moveable with respect to the housing 920 and the distal ribbon 914. In one embodiment, as the latch release ribbon 932 is moved proximally, the tang 928 of the latch 922 is lifted such that it disengages the slot 916 of the distal ribbon 914. While disengaged from the latch 922, the distal ribbon 914 may be moved in the distal direction, thereby increasing the distance between the proximal and distal anchors 118, 120.

In one embodiment, portions of the lumen of the housing 920 may be filled with an insert 926, as illustrated in FIG. 31B. As shown, insert 926 fills the spaces between the spacer 924 and the housing 920 of the tensioning element 190. In one embodiment, the portion of the lumen between the distal ribbon 914 and the housing 920 does not contain an insert 926, although in other embodiments it does. In one embodiment, it is advantageous to omit an insert 926 between the distal ribbon 914 and the housing 920 so as to reduce friction on the distal ribbon 914 when moving the distal ribbon 914 with respect to the housing 920.

FIG. 31C illustrates one embodiment of the distal ribbon 914, as described in greater detail above. The illustrated distal ribbon 914 is about 9 cm long, although the length of the distal ribbon 914 may be selected for the clinical requirements of the particular treatment. In general, the length of the distal ribbon 914 is in the range between about 2 cm and about 20 cm. The length of the proximal ribbon 902 has similar dimensions, such that the overall length of the implant 900 is in the range between about 2 cm and about 20 cm, preferably in the range between about 5 cm and about 15 cm, and more preferably in the range between about 7 cm and about 10 cm. In one embodiment, the overall length of the implant 900 is about 9 cm.

In the illustrated construction, the crossing profile of the implant 900 is determined by the diameter of the housing 920, as illustrated in FIG. 31B. In one embodiment, the diameter of the housing 920 is selected so that the implant 900 may be delivered inside of a catheter having an lumen with a diameter in the range between 6 French (approximately 0.079 inches) and 20 French (approximately 0.262 inches). In one embodiment, the length of the housing 920, as shown in FIG. 31A is in the range between about 3 mm and about 10 mm, preferably in the range between about 5 mm and about 8 mm, and more preferably in the range between about 6 mm and about 7 mm.

Referring to FIG. 31D, there is illustrated a disconnect subassembly 936, in accordance with one embodiment of the present invention. The disconnect subassembly 936 illustrates one mechanism by which the implant 900 is decoupled from a delivery catheter and handpiece, as described in greater detail below. Disconnect subassembly 936 includes the distal ribbon 914, a cover 938, a cover pull-wire 940, a tab 942, and a tab pull-wire 944. The pull-wire disconnect 918 of the distal ribbon 914 is engaged by a flange 946 protruding from the tab 942, as shown in greater detail in FIG. 31E. A tab pull-wire 944 is coupled to the tab 942 such that proximal movement of the tab pull-wire 944 with respect to a catheter 948 (as shown in FIG. 31F and described in greater detail below) translates into proximal movement of the distal ribbon 914, and distal tissue anchor 120 with respect to the proximal tissue anchor 118.

A cover 938, may comprise a stainless steel tube, is slid over the tab pull-wire 944 and distal ribbon 914. The cover 938 keeps the flange 946 of the tab 942 engaged with the pull-wire disconnect 918 of the distal ribbon 914 as the tab pull-wire 944 is moved in the proximal direction. The cover 938 is coupled to a cover pull-wire 940 such that movement of the cover pull-wire 940 in the proximal direction moves the cover 938 proximally, thereby releasing the tab 942 from the pull-wire disconnect 918 of the distal ribbon 914. In one embodiment, the cover pull-wire 940 is a stainless steel hyptotube, and the tab pull-wire 944 is a stainless steel hypotube or wire of a smaller diameter than the lumen of the cover pull-wire 940. In one embodiment, the cover pull-wire 940 and tab pull-wire 944 are substantially concentrically aligned, such that the tab pull-wire 944 travels within the cover pull-wire 940 from the disconnect subassembly 936 to the handpiece 958 (as shown in FIG. 32A).

A catheter 948, as shown in FIG. 31F may be removably coupled to the housing 920 of the implant 900 with a catheter coupling 950. In one embodiment, the catheter coupling 950 includes a slot 952, and two fingers 954, which extend into the slot 952. The fingers 954 are attached to the catheter 948, such that axial and rotational movement of the catheter 948 translates into axial and rotational movement of the housing 920 and implant 900. The slot 952 may be located on the housing 920, and in one embodiment, is shaped so as to create a bayonet type coupling between the housing 920 and catheter 948, as is known to those of skill in the art. In other embodiments, more or less than two fingers 954 are used to removably couple the housing 920 to the catheter 948. In one embodiment, a circular ring, tabs, hooks or other devices well known to those of skill in the art, are used instead of fingers 954.

In one embodiment, the fingers 954 are coupled to a release wire 956 such that proximal movement of the release wire 956 causes the fingers 954 to flex inward, and disengage from the slot 952 of the housing 920. When disengaged, the catheter 948 may be rotated and moved proximally with respect to the housing 920 so as to decouple the catheter 948 from the implant 900. In one embodiment, the release wire 956 is also coupled to the latch release ribbon 932 (shown in FIG. 31A). In one embodiment, proximal movement of the release wire 956 over a release distance causes the latch release ribbon 932 to disengage the latch 922 from the distal ribbon 914. In addition, proximal movement of the release wire 956 over the release distance does not cause the fingers 954 to flex sufficiently to disengage from the slot 952 of the housing 920, as described above.

In one embodiment, the release wire 956 comprises a hypotube with a lumen of sufficient diameter to contain the cover pull-wire 940 and tab pull-wire 944. In one embodiment, the release wire 956, cover pull-wire 940 and tab pull-wire 944 are all substantially coaxially aligned, and arranged such that the cover pull-wire 940 is at least partially within the release wire 956, and the tab pull-wire 944 is at least partially within the cover pull-wire 940 as they travel proximally from the catheter coupling 950 and disconnect subassembly 936 to the handpiece, as described in greater detail below.

Referring now to FIG. 32A, there is illustrated a handpiece 958, in accordance with another aspect of the present invention. Handpiece 958 includes a strain relief 960, body 962, distal actuator 964, interlock 966, and proximal actuator 968. The release wire 956, cover pull-wire 940, and tab pull-wire 944 enter the handpiece 958 via a lumen of the strain relief 960. The release wire 956 is coupled to a distal slider 970, the cover pull-wire 940 is coupled to a center slider 972, and the tab pull-wire 944 is coupled to a proximal slider 974. The body 962 may be formed from two or more pieces that are, for example, machined from metal or plastic, and joined together. Alternatively, the body 962 may be formed from one piece of material, for example, plastic that is formed by injection molding.

In one embodiment, the distal actuator 964 is threadingly engaged with the body 962 such that rotation of the distal actuator 964 results in axial movement of the distal actuator 964 with respect to the body 962. The distal actuator 964 is coupled to the distal slider 970 by at least one pin 976 (as shown in FIG. 32B) that is free to travel within an axial slot 978 in the body 962. The distal slider 970 is coupled to the release wire 956 by welding, bonding, adhesion, crimping, or other method as is known to those of skill in the art. The catheter 948 extends from the handpiece 958 to the implant 900, and is coupled to the implant 900 as described above, thereby fixing the axial position of the handpiece 958 with respect to the implant 900. As a result of the multiple couplings as described, rotation of the distal actuator 964 is translated into axial movement of the release wire 956 with respect to the handpiece 958, catheter 948, and implant 900. Proximal movement of the distal actuator 964 over the release distance, therefore causes the latch release ribbon 932 to move proximally sufficient to decouple the latch 922 from the distal ribbon 914, as described in greater detail above. Furthermore, additional proximal movement of the distal actuator 964 causes the fingers 954 of the catheter coupling 950 to disengage from the slot 952 of the housing 920, as described in greater detail above and below.

In one embodiment, the proximal actuator 968 is coupled to a threaded rod 980 such that rotation of the proximal actuator 968 causes the threaded rod 980 to rotate in the same direction. The threads of the threaded rod 980 engage threads located on an inside lumen of the center slider 972, through which the threaded rod 980 extends. The inside lumen of the proximal slider 974, through which the threaded rod 980 also extends, does not contain threads. The interlock 966 includes two pins 976 which engage both the center slider 972 and the proximal slider 974, and is free to move axially within a second axial slot 982 in the body 962. The interlock 966 causes the center slider 972 and the proximal slider 974 to remain fixed with respect to one another. Therefore, as the center slider 972 is moved proximally with respect to the body 962 from rotation of the proximal actuator 968, the proximal slider 974 move proximally with respect to the body 962 as well.

The interlock 966 may be removed from the handpiece 958 such that the center slider 972 and proximal slider 974 are no longer axially coupled. By removing the interlock 966, the center slider 972 is able to be moved proximally with respect to the proximal slider 974. Such adjustability is advantageous when manipulating the implant 900, and catheter 948, and during decoupling of the implant 900 from the catheter 948, as described in greater detail below.

In one embodiment, the center slider 972 is coupled to the cover pull-wire 940, such that proximal movement of the center slider 972 with respect to the body 962 results in proximal movement of the cover pull-wire 940 with respect to the catheter 948. In one embodiment, the proximal slider 974 is coupled to the tab pull-wire 944, such that proximal movement of the proximal slider 974 with respect to the body 962 results in proximal movement of the tab pull-wire 944 with respect to the catheter 948.

In one embodiment, the implant 900 is transluminally delivered to and deployed inside of the coronary sinus of a medical patient according to the following procedure. An outer sheath (not shown) is transluminally delivered to a distal region of the coronary sinus by using methods well known to those of skill in the art. The exact location within the coronary sinus is determined by the medical practitioner according to the clinical requirements of the particular case. The outer sheath contains a lumen of sufficient diameter to receive the implant 900. The implant 900 is coupled to the catheter 948, which is coupled to the handpiece 958, as described in greater detail above.

The implant 900 is advance distally to the distal tip of the outer tube by moving the handpiece 958 in the distal direction. The position of the implant 900 with respect to the outer tube and coronary sinus may be determined using fluoroscopic techniques, as are well known to those of skill in the art. When the implant 900 is properly positioned within the outer tube, within the coronary sinus, the outer tube is moved proximally, thereby exposing the distal tissue anchor 120. As described above, the distal tissue anchor 120 is biased to rotate to engage the medial wall of the coronary sinus under the force of the distal tissue anchor 120 spring 912. The handpiece 958 is then moved proximally to force the penetrating point 904 of the distal tissue anchor 120 into the heart tissue of the coronary sinus.

Once the distal tissue anchor 120 has adequately engaged the inside wall of the coronary sinus, the outer sheath is moved proximally, thereby exposing the proximal tissue anchor 118. The shape of the proximal ribbon 902 allow proximal tissue anchor 118 to engage tissue.

The implant 900 is adjusted so that the distance between the proximal tissue anchor 118 and the distal tissue anchor 120 is reduced, and the shape of the mitral valve annulus is modified to improve clinical performance, as described in greater detail herein. The handpiece 958 is held and the proximal actuator 968 is rotated. Rotating the proximal actuator 968 causes the tab pull-wire 944 and cover pull-wire 940 to move proximally, as described above. Proximal movement of the tab pull-wire 944 and cover pull-wire 940 is translated into proximal movement of the distal ribbon 914, as described above. The housing 920 of the tensioning element 190 is coupled to the catheter 948 at the catheter coupling 950, and the catheter 948 is coupled to the handpiece 958. Therefore, proximal movement of the cover pull-wire 940 and tab pull-wire 944 with respect to the handpiece 958 causes the distal ribbon 914 and distal tissue anchor 120 to move proximally with respect to the housing 920 and proximal tissue anchor 118.

In one embodiment, the medical practitioner verifies the position and shape of the implant 900 and mitral valve annulus using visualization techniques as are well known to those of skill in the art, including fluoroscopy. If the medical practitioner determines that the distal tissue anchor 120 needs to be moved distally, in one embodiment, the following procedure is followed. The distal actuator 964 is rotated with respect to the handpiece 958 until the distal actuator 964 moves proximally a distance equal to the release distance, as described in greater detail above. By doing so, the release wire 956 is moved proximally a distance equal to the release distance, which causes the opening 930 in the latch release ribbon 932 to move proximally a distance equal to the release distance as well. Such movement lifts the tang 928 of the latch 922 out of the slot 916 of the distal ribbon 914, so that the distal ribbon 914 may thereafter be moved distally by rotating the proximal actuator 968 in the opposite direction as rotated above.

When the implant 900 is properly positioned, and the distance between the proximal tissue anchor 118 and the distal tissue anchor 120 has been adjusted to the appropriate dimension, the medical practitioner may then conclude the medical treatment by removing the catheter from the medical patient. To do so, in one embodiment, the catheter 948 is decoupled from the housing 920 of the implant 900, and the cover pull-wire 940 and tab pull-wire 944 are decoupled from the distal ribbon 914.

To decouple the cover pull-wire 940 and tab pull-wire 944 from the distal ribbon 914, the interlock 966 is removed from the handpiece 958, and the proximal actuator 968 is rotated with respect to the handpiece 958. As the proximal actuator 968 is rotated with the interlock 966 removed, the center slider 972 moves proximally with respect to the proximal slider 974, which causes the cover pull-wire 940 to move proximally with respect to the tab pull-wire 944. Proximal movement of the cover pull-wire 940 causes the cover 938 to move proximally with respect to the tab 942, thereby allowing the tab 942 to disengage from the pull-wire disconnect 918 of the distal ribbon 914. The tab 942 may disengage from the pull-wire disconnect 918 under its own bias, or may be removed therefrom by rotating the handpiece 958, as described below.

To decouple the catheter 948 from the housing 920 of the implant 900, the distal actuator 964 is rotated until it moves proximally with respect to the handpiece 958 over a distance sufficiently greater than the release distance. In one embodiment, the distal actuator 964 is rotated until its proximal movement is limited by interference between the pin 976 and the proximal edge of the axial slot 978. Such movement causes the fingers 954 attached to the distal end of the catheter 948 flex inward a distance sufficient to clear the slot 952 in the housing 920, and latch release ribbon 932 is fully withdrawn, as described above. The handpiece 958 is then rotated and moved proximally, which causes the fingers 954 of the catheter 948 to rotate and move out of the housing 920 slot 952. In one embodiment, the rotation and proximal movement of the handpiece 958 also causes the flange 946 of the tab 942 to disengage from the pull-wire disconnect 918 of the distal ribbon 914. The catheter 948 is then removed from the patient's body by pulling it proximally out of the outer tube.

Figure 33:
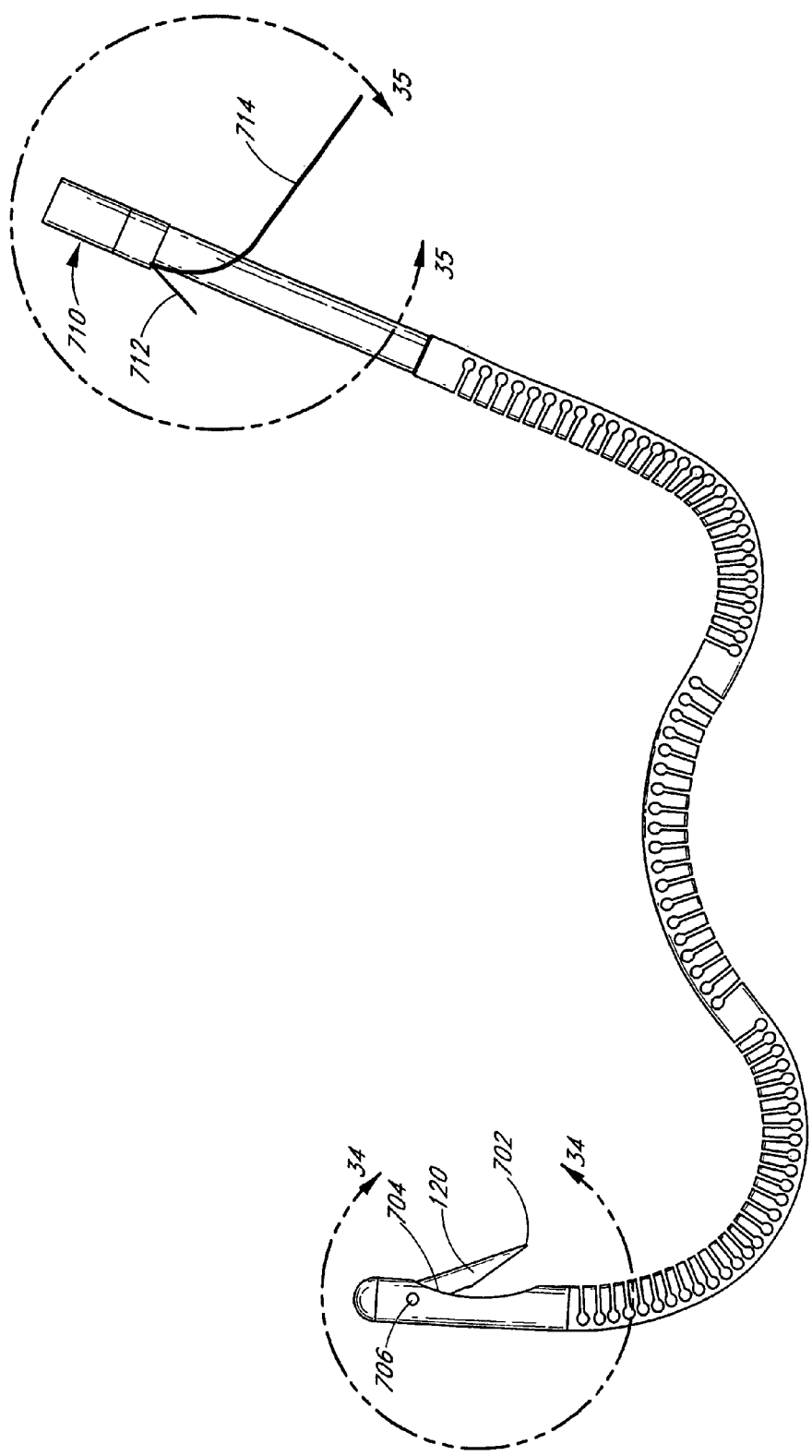
FIG. 33 is a side elevational view of an alternative implant in accordance with the present invention.
Figure 34:
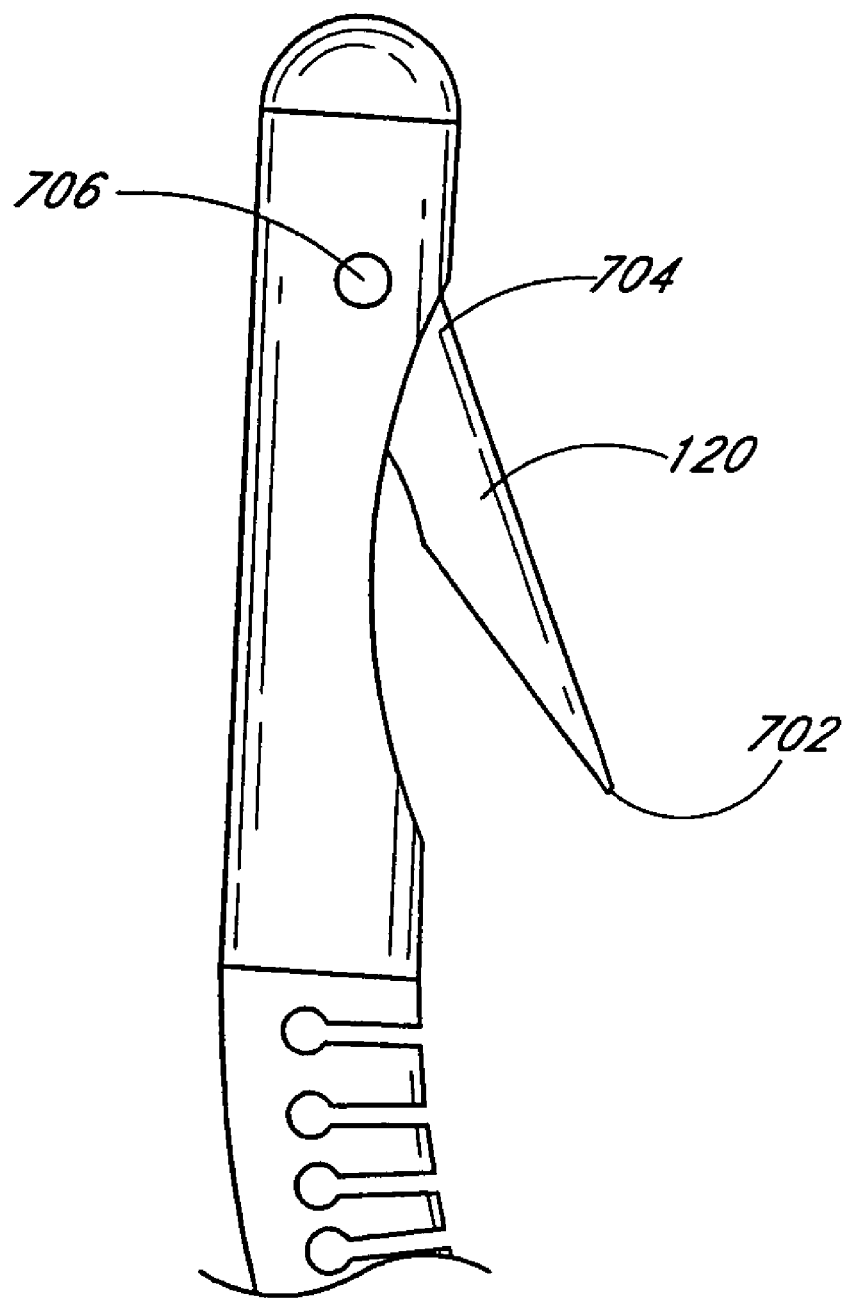
FIG. 34 is a side elevational close-up view of the distal end of the implant of FIG. 33.

Referring to FIG. 33, there is illustrated a side elevational view of an implant in accordance with the present invention. The implant includes a distal anchor, 120 which is shown in additional detail in FIG. 34. The distal anchor 120 comprises a sharpened proximal end 702 for penetrating tissue. The distal end 704 is pivotally attached to the implant wall, such as by one or more pins 706 rotatably received within an aperture in the tubular wall. The distal anchor is moveable between a first position in which it extends parallel to the longitudinal axis of the implant, to provide a low crossing profile, and a second position as illustrated in FIG. 34 when the tissue anchor is inclined radially outwardly from the longitudinal axis of the implant to engage tissue. Additional details of the distal anchor mechanism are illustrated in FIG. 36.

Figure 35:
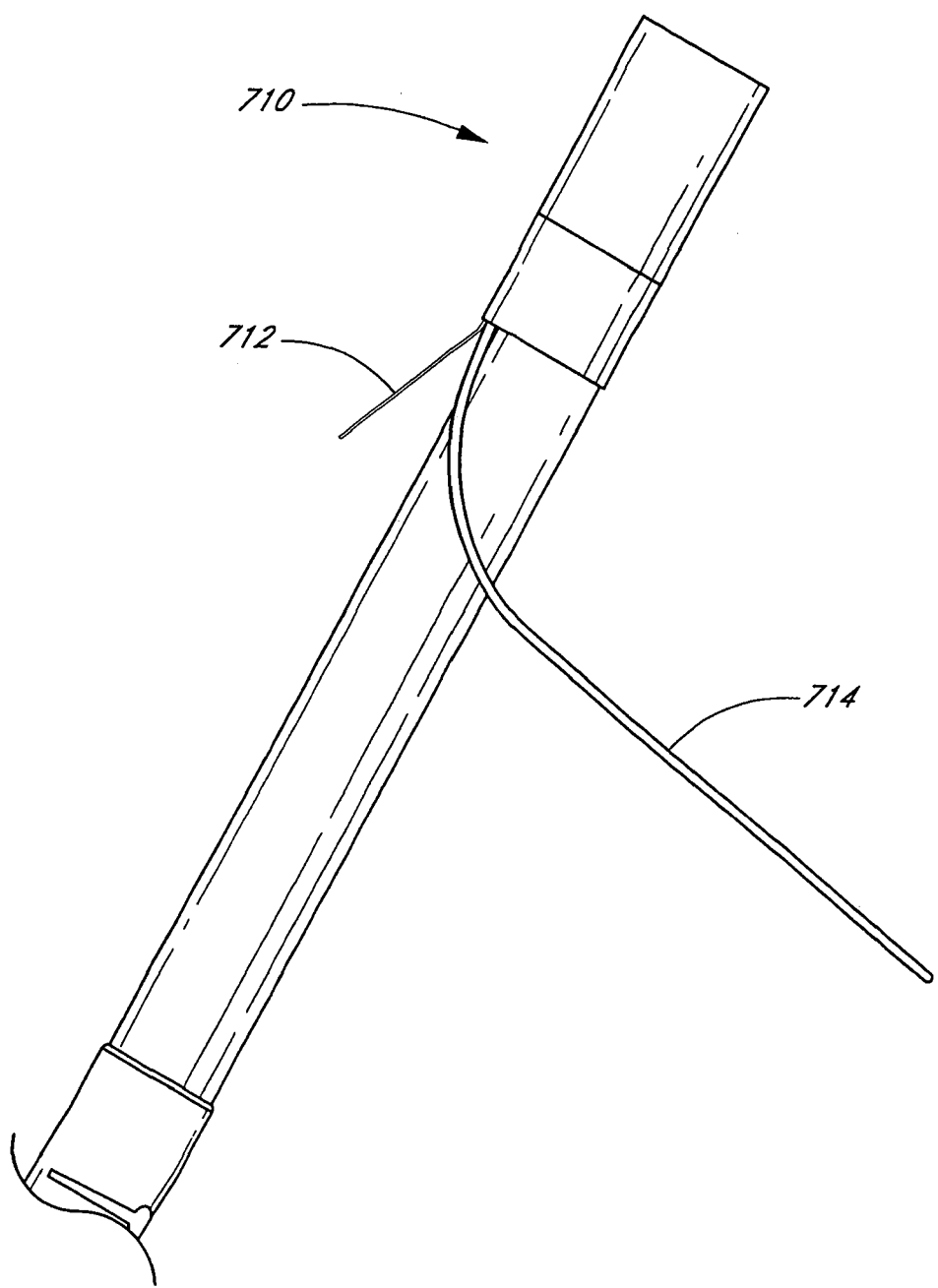
FIG. 35 is a side elevational close-up view of the proximal end of the implant of FIG. 33.

The proximal end of the implant 710 is illustrated in FIG. 35. The implant includes a proximal tissue anchor 712, which inclines radially outwardly away from the implant in the distal direction, on the mitral valve side of the device, for engaging the wall of the coronary sinus. Any of a variety of deployment mechanisms may be utilized for the proximal tissue anchor 712.

One or more of the proximal and distal anchors may be provided with a lateral alignment or biasing element for advancing the device laterally within the vessel so that the mitral valve side of the device is positioned against the coronary sinus wall. This will allow deployment of the proximal and distal anchors to fully engage the adjacent tissue. The lateral alignment structure illustrated in FIG. 35 is in the form of a flexible wire, strip, or loop 714 which, when released from the deployment catheter and/or advanced out of the implant, will reside within the coronary sinus and provide a lateral spring bias against the implant. In the illustrated embodiment, the loop 714 is in the form of a biased wire, such as nitinol. Any of a variety of structures may be utilized for maintaining the implant off center within the vessel, to optimize engagement of the tissue anchors with the vessel wall. For example, an inflatable side balloon on either the distal end of the deployment catheter or on the implant may be inflated during the tissue engaging step. Any of a variety of expandable wire cages may be mounted off center on either the implant or the distal end of the deployment catheter, for laterally moving the implant off center within the vessel.

Figure 36:
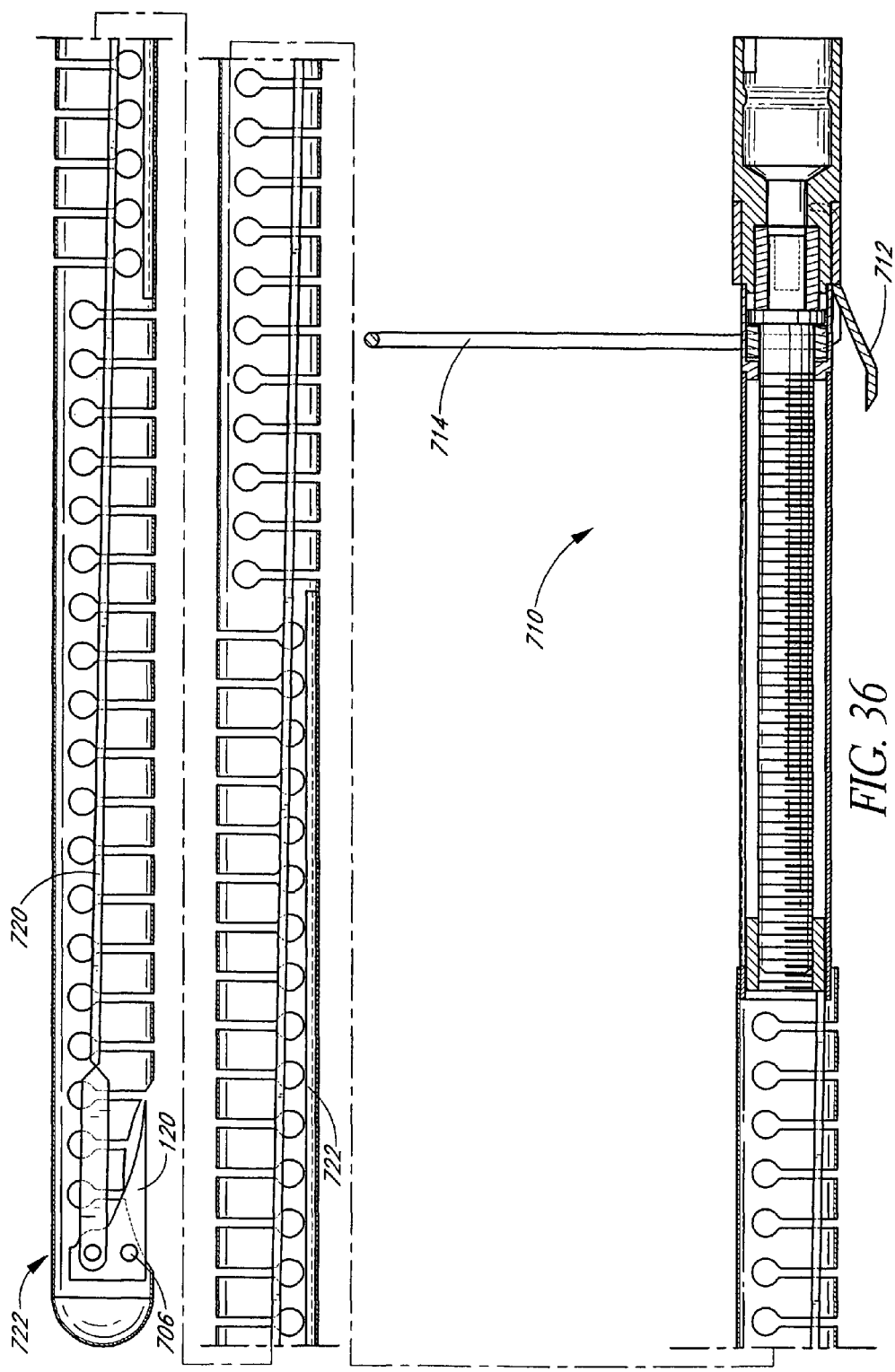
FIG. 36 is a side elevational cutaway view of an alternative implant in accordance with the present invention.

Referring to FIG. 36, there is illustrated a side elevational schematic view of the implant illustrated in FIGS. 33 through 35. As seen therein, the distal anchor 120 may be activated by axial proximal tension on the pull wire 720. The pull wire 720 is pivotally connected to the distal anchor 120, at a position which is offset laterally from an axis of rotation. The axis of rotation is concentric with one or more pins 706 which pivotally retain the distal anchor 120 in position at the distal end 722 of the implant. In the illustrated embodiment, proximal axial advancement of the pull wire 720 will cause the distal anchor 120 to incline radially outwardly with respect to the longitudinal axis of the implant.

A spine support 722 is illustrated at the central segment of the implant. Spine support 722 may comprise any of a variety of elements, such as a flexible ribbon of stainless steel, nitinol or other material, for enhancing the column strength of the implant in this region.

Figure 37:
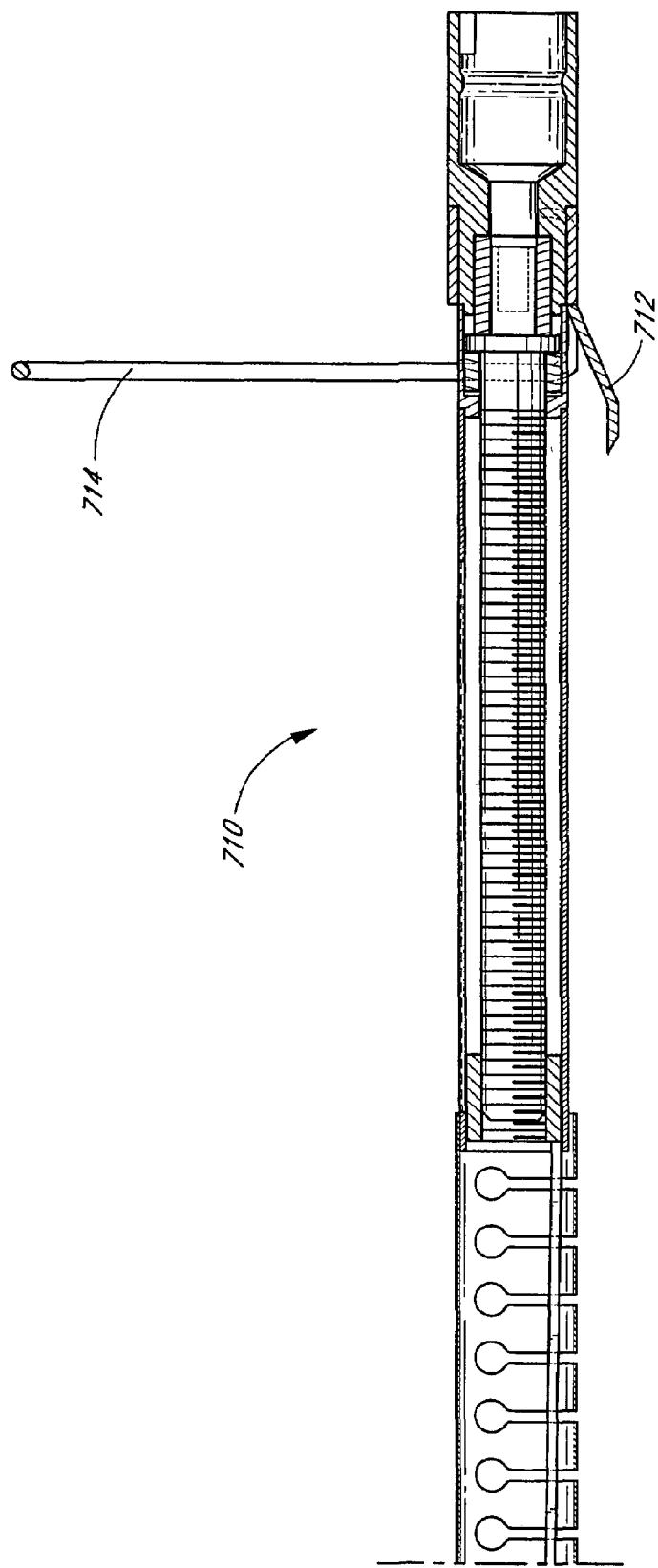
FIG. 37 is a close-up view of the proximal end of the implant of FIG. 36.

The proximal end 710 of the implant is illustrated in greater detail in FIG. 37. As seen therein, the anchor hoop 714 is schematically illustrated. Anchor hoop 714 may comprise any of a variety of structures, such as a loop as illustrated in FIG. 35 or other resilient element which may be biased radially outwardly from the longitudinal axis of the implant to contact the opposing side of the vessel wall and bias the proximal anchor hook 712 in the direction of the mitral valve side of the vessel wall.

In any of the embodiments disclosed herein, in which a tubular body is provided, the space within the tubular body may be utilized to carry any of a wide variety of drug delivery vehicles. For example, microporous beads, filaments or other structures may be carried within the tubular body. Any of a variety of dissolvable or absorbable gels or other carriers may be utilized, for carrying one or more active agents, for delivery from the implant into the vessel or vessel wall. The active agent may be released from the carrier using any of a variety of known drug delivery techniques, such as by erosion of the carrier, migration of the active agent through a microporous structure, or other as is known in the drug delivery arts.

The active agent carrier carried within the implant may be provided with any of a variety of active agents. These agents include anticoagulants, anti-inflammatory agents, drugs to inhibit smooth muscle cell proliferation or other responses to injury, antibiotics, drugs to enhance endothelial growth, or others known in the art.

In accordance with another aspect of the present invention, there is provided an electronically enabled implant. Any of the implants and associated methods previously disclosed herein can be modified to include the automation features described below, as will be apparent to those of skill in the art in view of the disclosure herein.

Although the implant will be described herein primarily in the context of a device for applying pressure to the posterior leaflet of the mitral valve, implants in accordance with the present invention may be utilized throughout a wide variety of other medical indications. For example, the implant may be modified for use in applying compressive force to other valves in the heart. Modified embodiments of the device may be placed adjacent or around the left ventricle of the heart, such as to assist CHF patients. The device may be positioned in the vicinity of any of a variety of natural sphincter muscles, such as the lower esophageal sphincter to treat gastroesophageal reflux disease. The implant may be positioned in the vicinity of the pylorus, or elsewhere on the stomach for use in the treatment of obesity. Modified versions of the implant disclosed herein may be positioned in the vicinity of a nerve, such that pressure may be selectively applied to the nerve to affect the transmission of pain or other signals.

In general, the implant may be configured for wireless communication with an external component. Alternatively, one or more electrical conductors may be provided for enabling direct electrical communication with the implant. Electrical conductors may be advanced through an artificial tissue tract, or may reside in the access lumen in the case of a transluminal implantation. The proximal end of electrical conductors may be positioned beneath the patient's skin, such as for subsequent access. Alternatively, the implant can have a remote receiving coil or antenna, typically implanted under the skin, connected to the implant by at least one conductor.

The electrical communication between the external component and internal component may enable the transmission of control signals to affect the internal component. In addition, diagnostic or status information may be read from or transmitted to the internal unit with the external component. Spatial relationship information about the position of the implant may also be transmitted to the external component. Force on the implant, or on a component of the implant, or relative position of implant components may be transmitted. Although the internal component will be described primarily herein in terms of a mechanical compression device for providing pressure against an extravascular tissue structure, any of a variety of onboard diagnostic sensors may additionally be provided, such as for determining physiological parameters such as blood flow, blood pressure, pH, $pO_2$, $pCO_2$, or a blood analyte of interest.

Although the present invention has been described in terms of certain preferred embodiments, it may be incorporated into other embodiments or performed through other steps by persons of skill in the art in view of the disclosure herein. In addition, features from any one of the embodiments disclosed herein may be incorporated into other embodiments as will be apparent to those of skill in the art. The scope of the invention is therefore not intended to be limited by the specific embodiments disclosed herein, but is intended to be defined by the full scope of the following claims.

What is claimed is:

1. A medical apparatus for remodeling a mitral valve annulus adjacent to the coronary sinus, comprising:
   an elongate body, having a proximal end and a distal end, the elongate body being movable from a first, flexible configuration for transluminal delivery to at least a portion of the coronary sinus to a second configuration for remodeling the mitral valve annulus; and
   a forming element attached to the elongate body for manipulating the elongate body from the first delivery configuration to the second remodeling configuration;
   wherein the elongate body in the remodeling configuration comprises proximal and distal segments which are each concave in a first direction and a central segment which is concave in a second direction and wherein at least in the remodeling configuration the forming element extends outside the body along the central segment.

2. A medical apparatus as in claim 1, wherein the elongate body comprises a tube having a plurality of transverse slots therein.

3. A medical apparatus as in claim 1, further comprising a lock for retaining the body in the remodeling configuration.

4. A medical apparatus as in claim 1, wherein the apparatus is movable from the delivery configuration to the remodeling configuration in response to proximal retraction of at least a portion of the forming element.

5. A medical apparatus as in claim 1, wherein the apparatus is movable from the delivery configuration to the remodeling configuration in response to distal advancement of at least a portion of the forming element.

6. A medical apparatus as in claim 1, further comprising at least one anchor for engaging a site within a vessel.

7. A medical apparatus as in claim 6, wherein the anchor comprises at least one barb for piercing the wall of the vessel.

8. A medical apparatus as in claim 6, comprising a first tissue anchor at the proximal end and a second tissue anchor at the distal end.

9. A medical apparatus as in claim 1, wherein the apparatus has an axial length of no more than about 10 cm.

10. A medical apparatus as in claim 9, wherein the maximum cross sectional dimension through the apparatus is no more than about 10 mm.

11. An implant for positioning within a patient, comprising:
    a deployment catheter;
    an elongate flexible body having a proximal section, a central section and a distal section;
    a forming element extending through at least the proximal and distal sections of the body; and
    a detachable coupling on the body, for removably attaching the body to the deployment catheter;
    wherein manipulation of the forming element deflects the central section laterally with respect to at least a portion of the proximal and distal sections to selectively apply a compressive force along a region of tissue.

12. An implant as in claim 11, wherein the body comprises a tubular wall.

13. An implant as in claim 12, wherein the tubular wall is substantially noncompressible along a first side of the central section.

14. An implant as in claim 13 comprising a plurality of voids in the wall along a second side of the central section, thereby permitting axial shortening or elongation of the second side.

15. An implant as in claim 14 wherein at least some of the voids comprise slots through the wall, extending generally transverse to a longitudinal axis.

16. An implant as in claim 15 comprising at least 10 transverse slots in the wall of the second side.

17. An implant as in claim 16 comprising at least 20 transverse slots in the wall of the second side.

18. An implant as in claim 11, wherein the forming element comprises an axially movable element.

19. An implant as in claim 18, wherein the forming element comprises a pull wire.

20. An implant as in claim 11, wherein manipulation of the forming element introduces a first curve in the central section of the body which is concave in a first direction, and at least a second curve in one of the proximal and distal sections of the body concave in a second direction.

21. An implant as in claim 20, wherein manipulation of the forming element reshapes the body into a "w" configuration.

22. An implant as in claim 11, wherein the detachable coupling comprises a rotatable coupling disposed along the proximal section of the flexible body for removable attachment to the deployment catheter.

23. An implant as in claim 22, wherein the deployment catheter further comprises a rotatable driver along a distal end for removable attachment to the rotatable coupling and wherein rotation of the rotatable driver produces axial movement of the forming element relative to the flexible body.

* * * * *